United States Patent
Lunyak et al.

(10) Patent No.: US 10,921,324 B2
(45) Date of Patent: Feb. 16, 2021

(54) COMPOSITIONS AND METHODS RELATED TO THE METHYLATION OF HISTONE H1.0 PROTEIN

(71) Applicant: Aelan Cell Technologies, Inc., San Francisco, CA (US)

(72) Inventors: Victoria Lunyak, San Anselmo, CA (US); James Robert Tollervey, San Rafael, CA (US)

(73) Assignee: AELAN CELL TECHNOLOGIES, INC., San Francisco, CA (US)

( * ) Notice: Subject to any disclaimer, the term of this patent is extended or adjusted under 35 U.S.C. 154(b) by 0 days.

(21) Appl. No.: 16/164,701

(22) Filed: Oct. 18, 2018

(65) Prior Publication Data
US 2019/0234948 A1 Aug. 1, 2019

Related U.S. Application Data

(63) Continuation of application No. PCT/US2017/028653, filed on Apr. 20, 2017.

(60) Provisional application No. 62/325,392, filed on Apr. 20, 2016, provisional application No. 62/325,408, filed on Apr. 20, 2016, provisional application No. 62/325,362, filed on Apr. 20, 2016, provisional application No. 62/355,265, filed on Jun. 27, 2016, provisional application No. 62/355,277, filed on Jun. 27, 2016.

(51) Int. Cl.
| | |
|---|---|
| G01N 33/573 | (2006.01) |
| C12N 9/10 | (2006.01) |
| C12P 21/06 | (2006.01) |
| C07K 14/47 | (2006.01) |
| C12P 21/02 | (2006.01) |
| C07K 16/18 | (2006.01) |
| G01N 33/68 | (2006.01) |
| G01N 33/543 | (2006.01) |

(52) U.S. Cl.
CPC ........... *G01N 33/573* (2013.01); *C07K 14/47* (2013.01); *C07K 16/18* (2013.01); *C12N 9/1007* (2013.01); *C12P 21/02* (2013.01); *C12P 21/06* (2013.01); *C12Y 201/01043* (2013.01); *G01N 33/54306* (2013.01); *G01N 33/6896* (2013.01); *C12Y 201/01* (2013.01); *G01N 2800/2821* (2013.01); *G01N 2800/50* (2013.01)

(58) Field of Classification Search
None
See application file for complete search history.

(56) References Cited

U.S. PATENT DOCUMENTS

| | | |
|---|---|---|
| 8,981,066 B2 | 3/2015 | Lunyak |
| 9,555,109 B2 | 1/2017 | Bogdanov et al. |
| 2003/0092095 A1 | 5/2003 | Huang |
| 2003/0200563 A1 | 10/2003 | Butler et al. |
| 2007/0287166 A1 | 12/2007 | Kanai et al. |
| 2008/0199964 A1 | 8/2008 | Shokat et al. |
| 2009/0149343 A1 | 6/2009 | Nightingale |
| 2010/0196941 A1 | 8/2010 | Braun et al. |
| 2010/0305473 A1 | 12/2010 | Yuzhakov |
| 2011/0201023 A1 | 8/2011 | Braulke et al. |
| 2012/0121600 A1 | 5/2012 | Rau et al. |
| 2013/0029998 A1 | 1/2013 | Mayanil et al. |
| 2013/0065254 A1* | 3/2013 | Lunyak .................. C07K 16/18 435/7.92 |
| 2013/0230858 A1 | 9/2013 | Cantor et al. |
| 2013/0345115 A1 | 12/2013 | An |
| 2014/0093865 A1 | 4/2014 | Espinosa et al. |
| 2014/0099305 A1 | 4/2014 | Epstein et al. |
| 2014/0162904 A1 | 6/2014 | Yu |
| 2015/0208985 A1 | 7/2015 | Huang |
| 2015/0330996 A1 | 11/2015 | Bawden et al. |
| 2019/0322729 A1* | 10/2019 | Lunyak .................. C07K 14/47 |

FOREIGN PATENT DOCUMENTS

| | | |
|---|---|---|
| WO | WO-2015/131836 A1 | 9/2015 |
| WO | WO-2017/049296 A1 | 3/2017 |
| WO | WO 2017/184873 A2 | 10/2017 |
| WO | WO 2017/184895 A2 | 10/2017 |
| WO | WO-2019/084332 A1 | 5/2019 |

OTHER PUBLICATIONS

Weiss et al. "Histone H1 variant-specific lysine methylation by G9a/KMT1C and Glp1/KMT1D" Epigenetics & Chromatin 3:7 (Year: 2010).*
Extended European Search Report dated Dec. 17, 2019 for EP Application No. 17786657.1, filed Apr. 20, 2017, 12 pages.
Kim, T. et al. "Dimethylation of H3K4 by Set1 recruits the Set3 histone deacetylase complex to 5' transcribed regions", Cell; 137(2): 259-272. (Apr. 17, 2009).
Connor et al. "A simple method for improving the specificity of anti-methyl histone antibodies", Epigenetics, Jul. 1, 2010. 5:392-395.
Fagan, T. J. "Letter: Nomogram for Bayes theorem", N. Engl. J. Med., Jul. 31, 1975. 293(5):257.

(Continued)

*Primary Examiner* — Larry D Riggs, II
*Assistant Examiner* — Zachary J Miknis
(74) *Attorney, Agent, or Firm* — Cooley LLP

(57) ABSTRACT

Provided herein are compositions and methods related to the production and detection of a histone H1.0 protein dimethylated at lysine residue 180 (K180) (H1.0K180me2 protein) or a histone H1.0 peptide dimethylated at a lysine residue corresponding to K180 (H1.0K180me2 peptides). The H1.0K180me2 protein and H1.0K180me2 peptides are useful for applications including, but not limited to, molecular diagnostics of DNA damage, genotoxic stress, radiation exposure, and Alzheimer's disease, therapeutics, monitoring of therapeutic regimens, patient stratification, and drug screening. Also provided herein are antibodies specific for the H1.0K180me2 protein and H1.0K180me2 peptides.

11 Claims, 33 Drawing Sheets

Specification includes a Sequence Listing.

(56) References Cited

OTHER PUBLICATIONS

Horiuchi et al. "Assay Development for Histone Methyltransferases", Assay and drug development technologies. May 1, 2013; 11 (4):227-36.
International Search Report and Written Opinion for related International Application No. PCT/US2017/028653 dated Oct. 19, 2017, 17 pages.
International Search Report and Written Opinion for related International Application No. PCT/US2017/028686 dated Dec. 5, 2017, 26 pages.
Jenuwein, T. et al. "Translating the histone code", Science, Aug. 20, 2001. [retrieved from the internet Apr. 24, 2019]. 293(5532):1074-80.
Kamakaka, R. T. et al. "Histone variants: deviants?", Genes. Dev. Feb. 2005. [retrieved from the internet Apr. 24, 2019]. 1;19(3):295-310.
Lunyak et al. "Epigenetic regulation of stem cell fate", Hum. Mol. Genet., 2008. [retrieved from the internet Apr. 24, 2019]. 17(1), R28-36.
NCBI Blast, "histone H1.0 [*Homo sapiens*]: NCBI Reference Sequence: NP_005309.1", [database online], [retrieved on Apr. 24, 2019] Retrieved from the National Center for Biotechnology Information Search database using Internet <URL:https://www.ncbi.nlm.nih.gov/protein/NP_005309.1/>. 1 page.
Pogribny et al. "Fractionated Low-Dose Radiation Exposure Leads to Accumulation of DNA Damage and Profound Alterations in DNA and Histone Methylation in the Murine Thymus", Mol Cancer Res, Oct. 1, 2005. [retrieved from the internet Apr. 24, 2019]. 3: 553-61.
Prince, M. J. "Predicting the onset of Alzheimer's disease using Bayes' theorem", Am J Epidemiol. Feb. 1, 1996 [retrieved from the internet Apr. 24, 2019]; 143(3):301-8.
Tollervey, J. R. et al. "Epigenetics: judge, jury and executioner of stem cell fate", Epigenetics, Aug. 2012. 7(8):823-40.
Wan, L. B. et al. "Regulation of imprinting in clusters: noncoding RNAs versus insulators", Adv. Genet. 2008. 61:207-223.
Weiss et al. "Histone H1 variant-specific lysine methylation by G9a/KMT1C and Glp1/KMT1D", Epigenetics & Chromatin, Mar. 24, 2010, 3(7):1-13.
International Search Report and Written Opinion for related International Application No. PCT/US2018/057602 filed dated Feb. 1, 2019, 18 pages.
Lanning, D et al. Intestinal Microflora and Diversification of the Rabbit Antibody Repertoire. Journal of Immunology. Aug. 15, 2000, vol. 165, No. 4, pp. 2012-2019; Genbank supplement p. 1; 10 pages.
Lanning, DK et al., "Immunoglobulin heavy chain, partial [Oryctolagus cuniculus]: GenBank: AAB70644.1", National Center for Biotechnology Information. Genbank Entry. Aug. 13, 1997 [retrieved on Dec. 17, 2018]. Retrieved from the internet: <URL:https://www.ncbi.nlm.nih.gov/protein/AAB70644.1?report=genbank&log$=protalign&blast_rank=1&RID=1G1G3EYD015>; 1 page.
Sehgal, D. et al., Generation of Heterogeneous Rabbit Anti-DNP Antibodies by Gene Conversion and Hypermutation of Rearranged VL and VH Genes during Clonal Expansion of B cells in Splenic Germinal Centers. European Journal of Immunology. Dec. 2000, vol. 30, No. 12; pp. 3634-3644, 11 pages.
Non-Final Office Action dated Jul. 9, 2020 for U.S. Appl. No. 16/164,676, filed Oct. 18, 2018, 20 pages.
Edwards, et al. "The remarkable flexibility of the human antibody repertoire; isolation of over one thousand different antibodies to a single protein, BLyS"; J Mol Biol.; 334(1):103-18. (Nov. 14, 2003).
Final Office Action dated Dec. 31, 2020 for U.S. Appl. No. 16/164,676, filed Oct. 18, 2018, 18 pages.

\* cited by examiner

Indirect Detection of H1.0K180me2:
Use of Biotinylated H1.0K180me2 Proteins or Peptides to
Recognize Autoantibodies to H1.0K180me2

Direct Detection of H1.0K180me2:
Use of H1.0K180me2 Antibodies for Detection and
Labeled H1.0K180me2 Proteins or Peptides as a Reference Standard

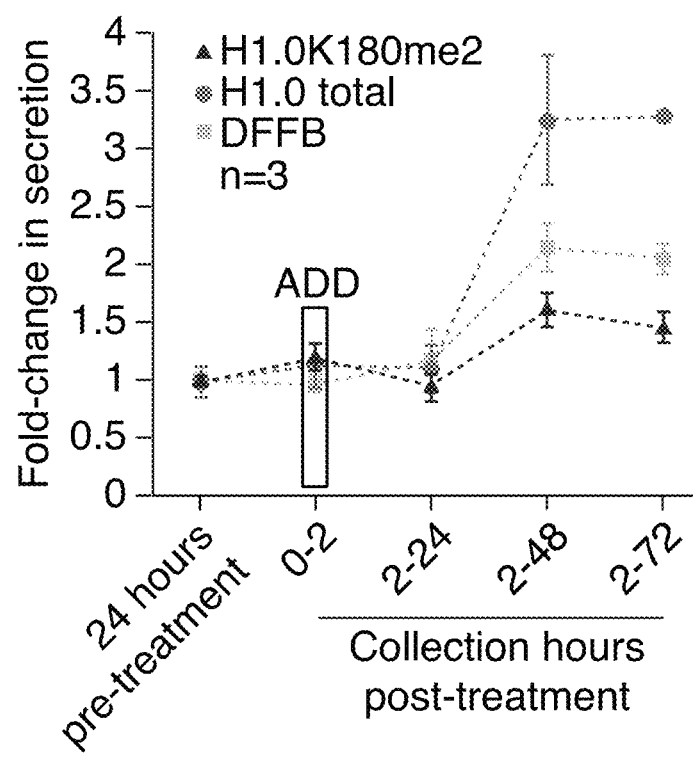

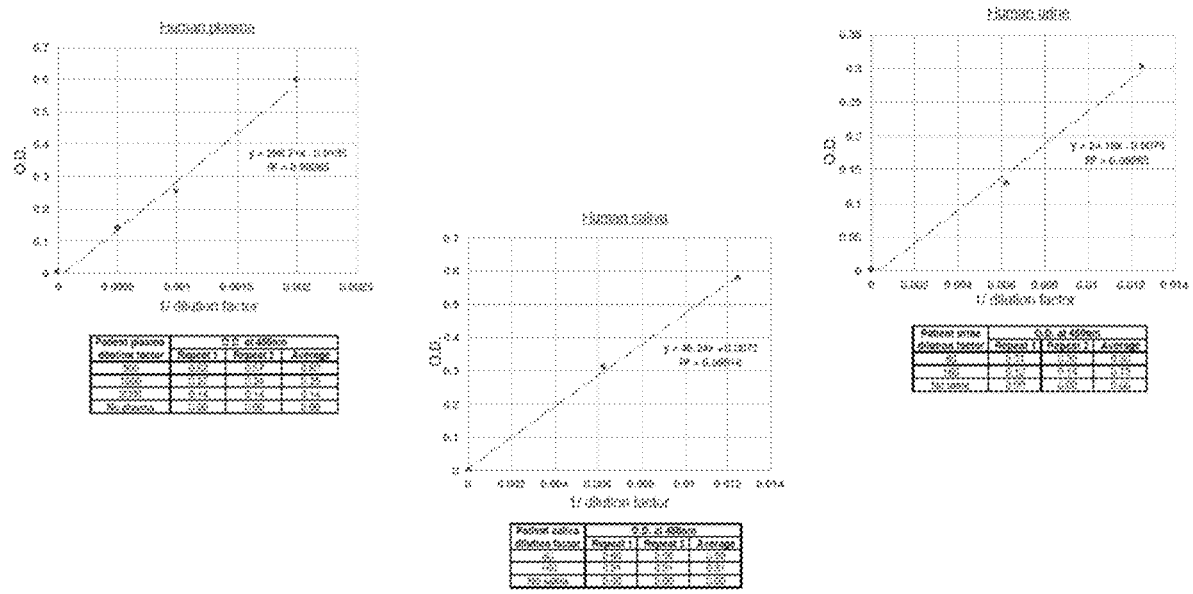
FIG. 6B  H1.0K180me2 IgG Autoantibodies can be Detected in Various Biofluids Using Labeled H1.0K180me2 Peptides, Using an Indirect ELISA FIG. 6D  Serological measurements of levels of circulating total IgM and anti-H1.0K180me2 IgM autoantibodies for the diagnosis of Alzheimer's disease.
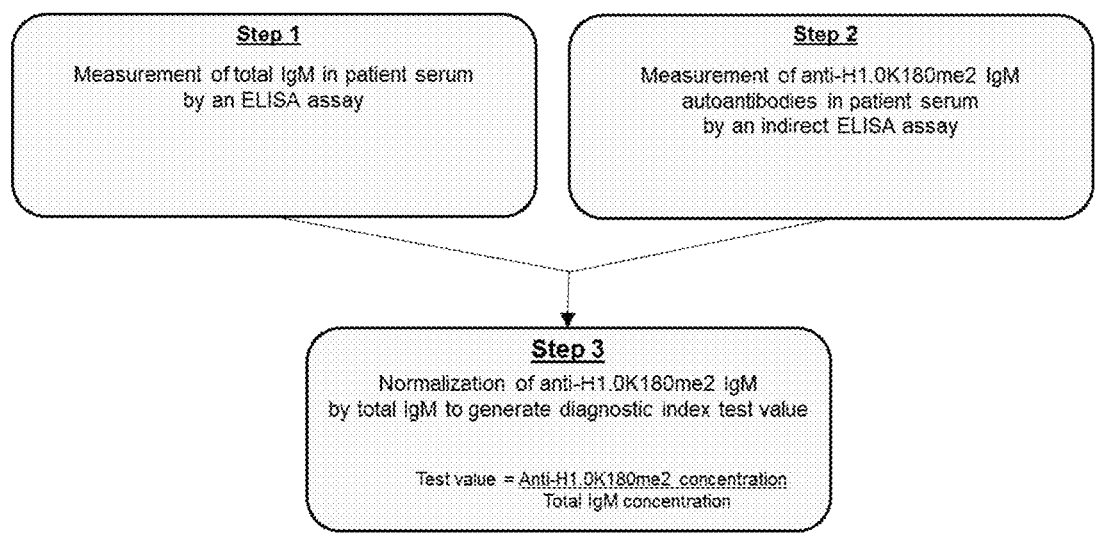

FIG. 6E  STEP 1. The box plot of distribution of total IgM concentrations in the reference test (AD) and neurologic control samples
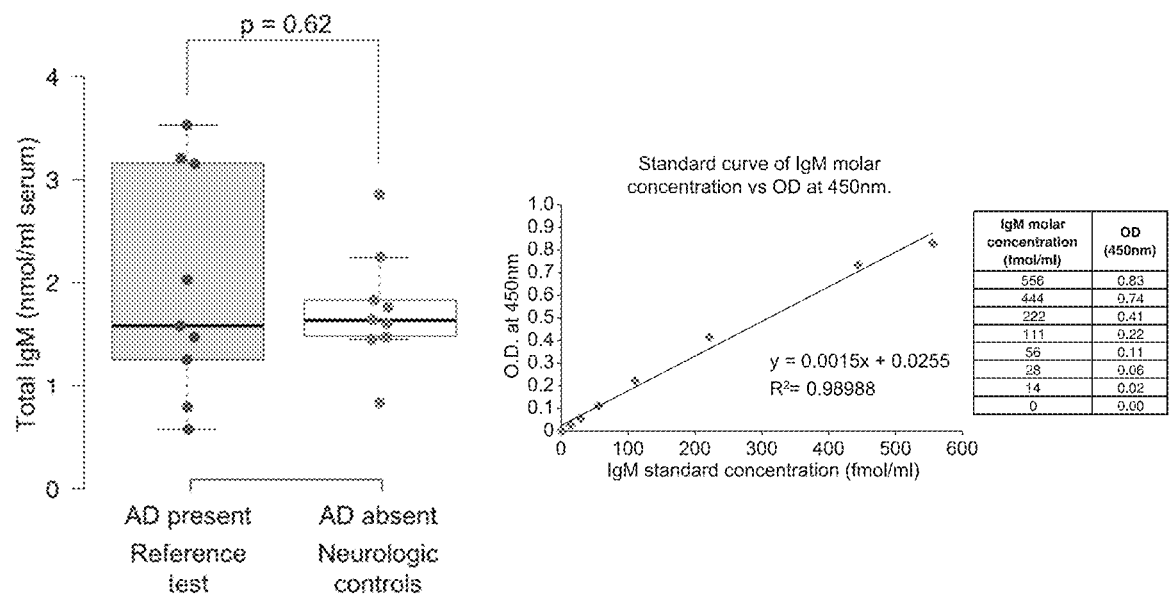

FIG. 6F  STEP 2 Indirect ELISA method for the detection and quantification of autoanti H1.0K180me2 IgM in samples of bodily fluids
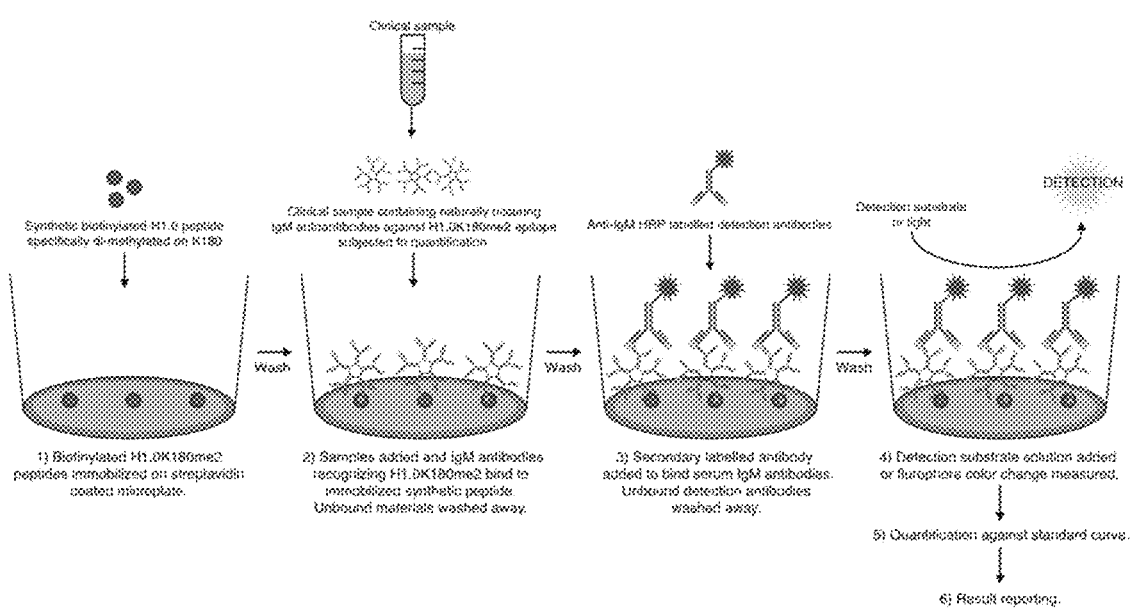

FIG. 6G   STEP 2 Calibration curve for Indirect ELISA method for detection and quantification of autoanti H1.0K180me2 IgM in samples of bodily fluids
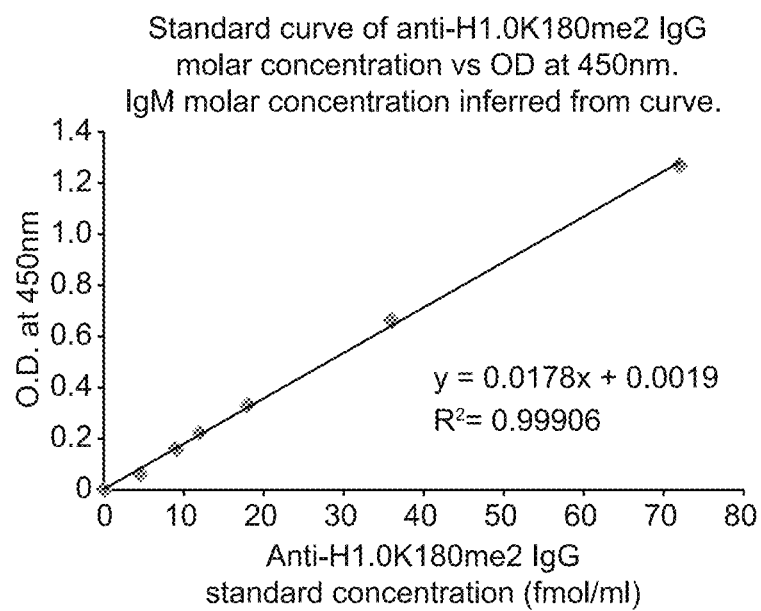

FIG. 6H  STEP 2 Indirect ELISA method for detection and quantification of autoanti- H1.0K180me2 IgM in samples of bodily fluids
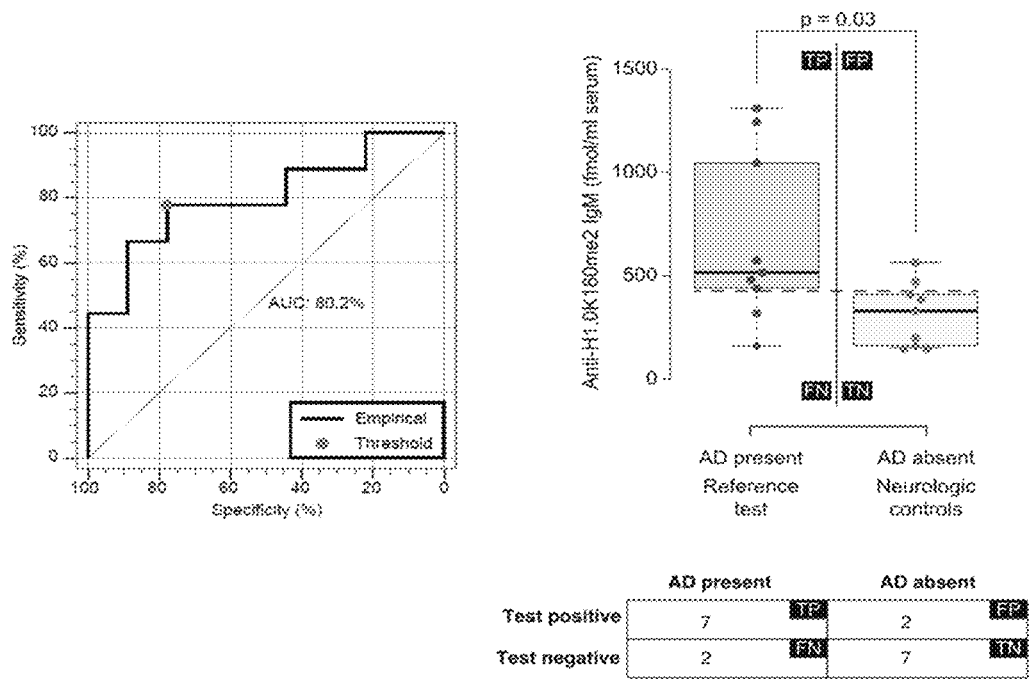

FIG. 6I  STEP 3 Normalized Indirect ELISA method for detection and quantification of autoanti-H1.0K180me2 IgM in samples of bodily fluids ( normalized against total IgM measurements in STEP 1)
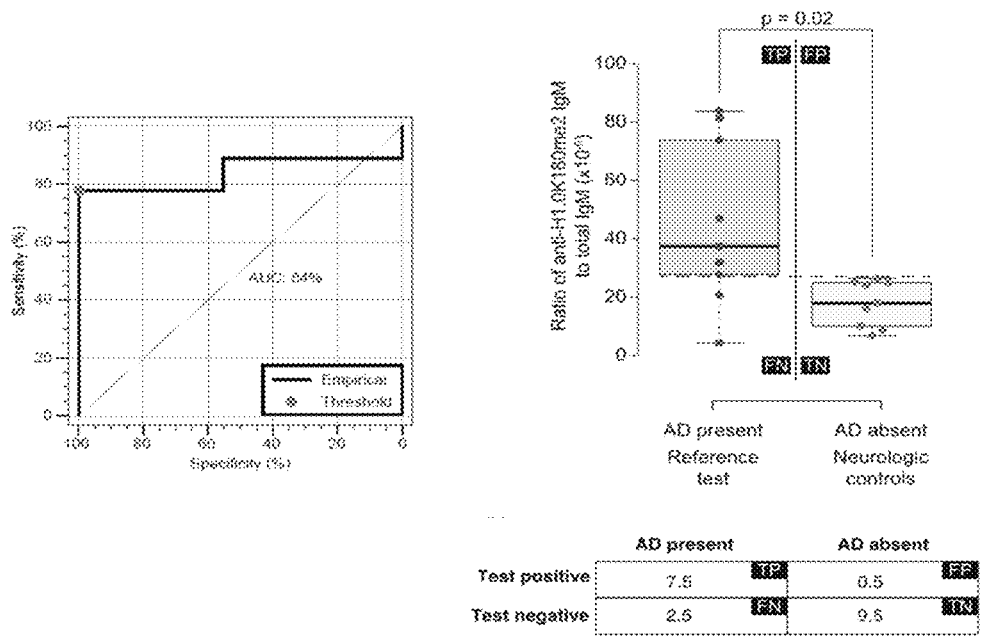

Reproducibility of the test between different operators and different laboratory settings Numerical values represent spectral counts of each species identified after methylation reaction

FIG. 9B

| Enzyme | Input | Confidence | Peptide sequence | Spectral counts | Modified lysine position within peptide sequence | Modified lysine position within full protein |
|---|---|---|---|---|---|---|
| G9A | Non-methylated peptide | < 95% | AKPVKASKPKKAKPVKPK (SEQ ID NO: 36) | 3 | - | |
| G9A | Non-methylated peptide | < 95% | AKPVKASKPKKAKPVKPK (SEQ ID NO: 36) | 3227 | K16(Dimethyl) | K180(Dimethyl) |
| G9A | K180me2 peptide | ≥ 99% | AKPVKASKPKKAKPVKPK (SEQ ID NO: 36) | 2815 | K16(Dimethyl) | K180(Dimethyl) |
| G9A | K180me2 peptide | ≥ 95% | AKPVKASKPKKAKPVKPK (SEQ ID NO: 36) | 36 | K2(Methyl); K16(Dimethyl) | K166(Methyl); K180(Dimethyl) |
| G9A | K180me2 peptide | ≥ 99% | AKPVKASKPKKAKPVKPK (SEQ ID NO: 36) | 10 | K10(Trimethyl); K11(Trimethyl); K13(Methyl); K16(Dimethyl) | K174(Trimethyl); K175(Trimethyl); K177(Methyl); K180(Dimethyl) |
| G9A | K180me2 peptide | ≥ 95% | AKPVKASKPKKAKPVKPK (SEQ ID NO: 36) | 30 | K10(Methyl); K16(Trimethyl) | K174(Methyl); K16(Trimethyl) |
| GLP | Non-methylated peptide | < 95% | AKPVKASKPKKAKPVKPK (SEQ ID NO: 36) | 2 | - | |
| GLP | Non-methylated peptide | ≥ 99% | AKPVKASKPKKAKPVKPK (SEQ ID NO: 36) | 56 | K16(Dimethyl) | K180(Dimethyl) |
| GLP | K180me2 peptide | ≥ 99% | AKPVKASKPKKAKPVKPK (SEQ ID NO: 36) | 1935 | K16(Dimethyl) | K180(Dimethyl) |
| GLP | K180me2 peptide | ≥ 99% | AKPVKASKPKKAKPVKPK (SEQ ID NO: 36) | 20 | K10(Methyl); K16(Trimethyl) | K174(Methyl); K180(Trimethyl) |

Numerical values represent spectral
counts of each species identified
after methylation reaction Numerical values represent spectral
counts of each species identified
after methylation reaction Numerical values represent spectral
counts of each species identified
after methylation reaction (SEQ ID NO: 99)

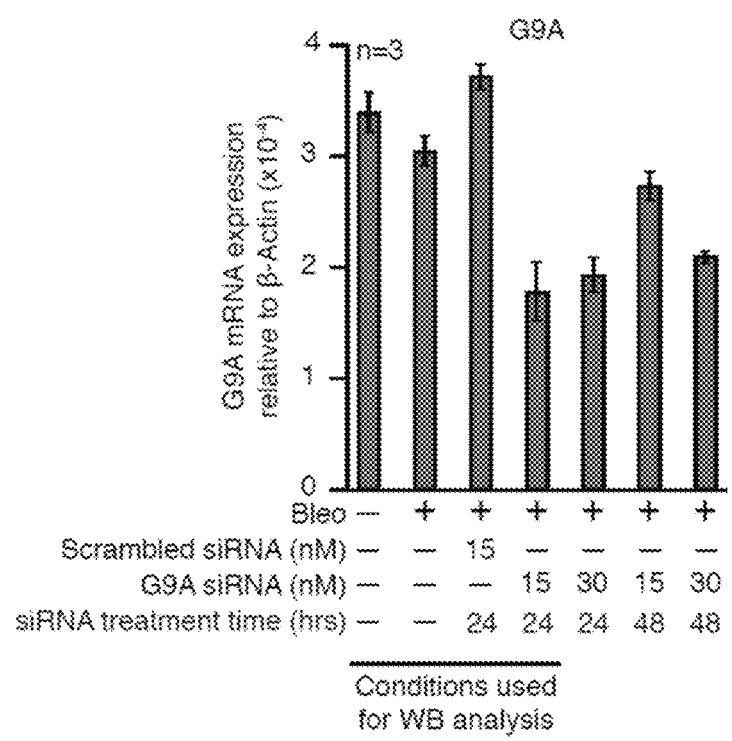
FIG. 15B qPCR

COMPOSITIONS AND METHODS RELATED TO THE METHYLATION OF HISTONE H1.0 PROTEIN

CROSS-REFERENCE TO RELATED APPLICATIONS

This application is a continuation of International Patent Application No. PCT/US2017/028653, filed Apr. 20, 2017, which claims priority to U.S. Provisional Application Ser. No. 62/325,392, filed Apr. 20, 2016, U.S. Provisional Application Ser. No. 62/325,408, filed Apr. 20, 2016, U.S. Provisional Application Ser. No. 62/325,362, filed Apr. 20, 2016, U.S. Provisional Application Ser. No. 62/355,265, filed Jun. 27, 2016, and U.S. Provisional Application Ser. No. 62/355,277, filed Jun. 27, 2016, each of which are incorporated herein by reference in their entirety.

DESCRIPTION OF THE TEXT FILE SUBMITTED ELECTRONICALLY

The contents of the text file submitted electronically herewith are incorporated herein by reference in their entireties: A computer readable format copy of the Sequence Listing (filename: ALNC_006_01US_SubSeqList_ST25.txt, date recorded Jul. 13, 2020, file size 40 kilobytes).

BACKGROUND

The histone lysine methyltransferases G9A (KMT1C/EHTM2) and G9A-like protein (GLP; (KMT1D/EHTM1) are responsible for the post-translational modification (PTM) of various proteins. G9A/GLP-dependent PTMs play roles in numerous cellular processes including gene expression, genomic stability, stem cell maturation, cell lineage development, genetic imprinting, DNA methylation, DNA replication, immune system response, drug addiction and cancer.

Histone proteins are the main protein components of chromatin around which double-stranded DNA is wound. Changes in histone proteins can differentially alter access of the transcriptional machinery to some genes while leaving access to other genes intact. Differential chromatin condensation achieved by histone PTMs underlies packaging of chromatin (Lunyak and Rosenfeld 2008) *Hum. Mol. Genet.,* 17: R28-36; Jenuwein and Allis (2001) *Science,* 293: 1074-1080). Histone PTMs can act as an epigenetic code and play critical roles in many aspects of the cellular responses tightly linked to development, injury, disease and aging.

Five major families of histones exist: H1, H2A, H2B, H3 and H4. Histones H2A, H2B, H3 and H4 are known as the core histones, while histones H1 and H5 are known as the linker histones. G9A/GLP-dependent post-translational modifications of histone protein H3, to produce monomethylated H3K9me1, dimethylated H3K9me2, dimethylated H3K27me2 and monomethylated H3K56me1, have been observed.

Histone H1 and the members of this family can differentially affect the condensation of the chromatin fiber and its stability (Wan et al. (2008) *Adv Genet*). In addition to the canonical histone H1, many variant forms of H1 exist in different cells of the organism: H1.0, H1.1, H1.2, H1.3, H1.4, H1.5, and H1X are variants of H1 (Tollervey & Lunyak, (2012) *Epigenetics;* Kamakaka (2005) *Genes Dev*).

Lysine methyltransferases (KMTs) catalyze mono-, di-, or tri-methylation by transferring one, two, or three methyl groups, respectively, from methyl donors. A single KMT might provide for different methylation events, but substrate specificity or the ability of KMT to recognize a specific lysine residue cannot not be predicted by primary structure alone or deduced from its secondary structure. Although ~80 enzymes have been shown to dynamically regulate histone lysine methylation, only a few histone and non-histone proteins have been reported as substrates of these enzymes.

Post translational modification on H1 family members have been identified. An ability to control and direct post translational modifications of H1.0 may be utilized in a broad spectrum of applications, including molecular diagnostics, therapeutics and drug screening. Provided herein are compositions and methods for this purpose.

BRIEF SUMMARY

In one aspect, provided herein is an in vitro method for dimethylating a histone H1.0 peptide or a histone H1.0 protein comprising contacting the protein or peptide with a methyltransferase enzyme and a methyl donor under conditions that produce a specifically dimethylated protein or peptide, wherein the protein or peptide is specifically dimethylated at a lysine residue corresponding to K180 of a human histone H1.0 protein, and wherein the methyltransferase enzyme is G9A methyltransferase or GLP methyltransferase. In some embodiments, the peptide comprises a sequence selected from the group consisting of SEQ ID NOS:36-68. In some embodiments, the protein comprises the sequence of SEQ ID NO:1. In some embodiments, the protein or peptide is contacted with a G9A methyltransferase. In some embodiments, the protein or peptide is contacted with a GLP methyltransferase. In some embodiments, the methyl donor is S-Adenosyl-L-Methionine. In some embodiments, the contacting is performed in a methylation buffer. In some embodiments, greater than 50%, greater than 60%, greater than 70%, greater than 80%, greater than 90%, greater than 95%, or even greater than 99% of the product is dimethylated at a lysine residue corresponding to K180 of the human histone H1.0 protein. In a related aspect, provided herein is an antibody that specifically binds the dimethylated protein or peptide produced by the in vitro method provided.

In another aspect, provided herein is a synthetic histone H1.0 peptide comprising a dimethylated lysine residue, wherein the lysine residue corresponds to K180 of a human histone H1.0 protein. In some embodiments, the peptide comprises the sequence selected from the group consisting of SEQ ID NOS:3-35. In some embodiments, the peptide comprises the sequence selected from the group consisting of SEQ ID NOS:3-5. In some embodiments, the peptide does not comprise any other lysine residues that are methylated. In some embodiments, the peptide is labeled. In some embodiments, the peptide is biotinylated. In some embodiments, the peptide is attached to solid surface. In some embodiments, the peptide is attached a bead, column, resin, or a microplate. In a related aspect, provided herein is an antibody that specifically binds the synthetic dimethylated peptide.

In another aspect, provided herein is a synthetic histone H1.0 protein (full length protein) comprising a label and a dimethylated lysine residue, wherein the lysine residue corresponds to K180 of a human histone H1.0 protein. In some embodiments, the protein comprises the sequence of SEQ ID NO:2. In some embodiments, the protein does not comprise any other lysine residues that are methylated. In some embodiments, the label is biotin. In some embodiments, the protein is attached to solid surface. In some embodiments, the protein is attached a bead, column, resin, or a microplate. In a related aspect, provided herein is an antibody that specifically binds the synthetic dimethylated protein.

In another aspect, provided herein is a histone H1.0 peptide or a histone H1.0 protein specifically dimethylated at a lysine residue corresponding to K180 of a human histone H1.0 protein produced by a method comprising contacting an H1.0 protein or an H1.0 peptide with a methyltransferase enzyme and methyl donor under conditions that allow for the specific dimethylation, wherein the methyltransferase enzyme is G9A methyltransferase or GLP methyltransferase. In some embodiments, the H1.0 peptide comprises a sequence selected from the group consisting of SEQ ID NOs:36-68. In some embodiments, the H1.0 protein comprises the sequence of SEQ ID NO:1. In some embodiments, the specifically dimethylated H1.0 protein produced comprises the sequence of SEQ ID NO:2. In some embodiments, the specifically dimethylated H1.0 peptide produced comprises the sequence of SEQ ID NOS:3-35. In a related aspect, provided herein is an antibody that specifically binds the dimethylated protein or peptide produced by the in vitro method provided.

In another aspect, provided herein is an antibody that specifically binds a dimethylated antigen, wherein the dimethylated antigen is a histone H1.0 peptide or histone H1.0 protein comprising a dimethylated lysine residue, wherein the lysine residue corresponds to K180 of a human histone H1.0 protein, wherein the dimethylated lysine residue is required for binding. In some embodiments, the dimethylated antigen does not comprise any other lysine residues that are methylated. In some embodiments, the antibody does not bind, or only minimally binds a dimethylated antigen wherein the dimethylated antigen is a histone H1.0 peptide or histone H1.0 protein comprising a dimethylated lysine residue, wherein the lysine residue corresponds to K166, K172, K174, K175, and/or K177 of a human histone H1.0 protein. In some embodiments, the antibody does not bind, or only minimally binds a monomethylated antigen wherein the monomethylated antigen is a histone H1.0 peptide or histone H1.0 protein comprising a monomethylated lysine residue, wherein the lysine residue corresponds to K166, K172, K174, K175, K177, and/or K180 of a human histone H1.0 protein. In some embodiments, the antibody does not bind, or only minimally binds a trimethylated antigen wherein the trimethylated antigen is a histone H1.0 peptide or histone H1.0 protein comprising a trimethylated lysine residue, wherein the lysine residue corresponds to K166, K172, K174, K175, K177, and/or K180 of a human histone H1.0 protein. In some embodiments, the antibody binds the dimethylated antigen in any medium. In some embodiments, the antibody is a monoclonal antibody. In some embodiments, the antibody is a polyclonal antibody. In some embodiments, the antibody is at least 2-fold more specific for the dimethylated antigen, than a monomethylated antigen, wherein the monomethylated antigen comprises a monomethylated lysine residue, and wherein the lysine residue corresponds to K180 of a human histone H1.0 protein. In some embodiments, the antibody is labeled. In some embodiments, the antibody is biotinylated. In some embodiments, the antibody is attached to solid surface. In some embodiments, the antibody attached a bead, column, resin, or a microplate.

In another aspect, provided herein is a kit for the in vitro methylation of an H1.0 protein or H1.0 peptide comprising: (a) an H1.0 protein or an H1.0 peptide; (b) a G9A methyltransferase or GLP methyltransferase enzyme; and a methyl donor. In some embodiments, the kit comprises an H1.0 protein, wherein the H1.0 protein comprises the sequence of SEQ ID NO:1. In some embodiment, the kit comprises an H1.0 peptide. In some embodiments, the H1.0 peptide comprises a sequence selected from the group consisting of SEQ ID NOs:36-68. In some embodiments, the kit comprises a G9A methyltransferase enzyme. In some embodiments, the kit comprises a GLP methyltransferase enzyme. In some embodiments, the methyl donor is S-Adenosyl-L-Methionine. In some embodiments, the kit further comprises a methylation buffer.

In another aspect, provided herein is a kit comprising a synthetic histone H1.0 peptide or a synthetic histone H1.0 protein specifically dimethylated at a lysine residue corresponding to K180 of a human histone H1.0 protein. In some embodiments, the kit comprises a synthetic H1.0K180me2 peptide and the peptide comprises the sequence selected from the group consisting of SEQ ID NOS:3-35. In some embodiments, the peptide is labeled. In some embodiments, the peptide is biotinylated. In some embodiments, the peptide is attached to solid surface. In some embodiments, the peptide is attached a bead, column, resin, or a microplate. In some embodiments, the peptide is provided for the detection of H1.0K180me2 autoantibodies in a sample. In some embodiments, the peptide is provided as a reference standard. In some embodiments, the kit comprises a H1.0K180me2 protein, wherein the H1.0K180me2 protein comprises the sequence of SEQ ID NO:1. In some embodiments, the protein is labeled. In some embodiments, the protein is biotinylated. In some embodiments, the protein is attached to solid surface. In some embodiments, the protein is attached a bead, column, resin, or a microplate. In some embodiments, the protein is provided for the detection of H1.0K180me2 autoantibodies in a sample. In some embodiments, the protein is provided as a reference standard. In some embodiments, the kit further comprises an H1.0K180me2 binding antibody. In some embodiments, the kit is used for the detection of Alzheimer's disease, radiation exposure, exposure to a genotoxin, or exposure to a DNA damaging agent. In some embodiments, the kit is used for drug screening. In some embodiments, the kit is used for patient stratification. In some embodiments, the kit is used for treatment selection. In some embodiments, the kit is used for therapeutics.

In another aspect, provided herein is a kit comprising an antibody that specifically binds a dimethylated antigen, wherein the dimethylated antigen is a histone H1.0 peptide or histone H1.0 protein comprising a dimethylated lysine residue, wherein the lysine residue corresponds to K180 of a human histone H1.0 protein. In some embodiments, the dimethylated antigen does not comprise any other lysine residues that are methylated. In some embodiments, the antibody does not bind, or only minimally binds a dimethylated antigen wherein the dimethylated antigen is a histone H1.0 peptide or histone H1.0 protein comprising a dimethylated lysine residue, wherein the lysine residue corresponds to K166, K172, K174, K175, and/or K177 of a human histone H1.0 protein. In some embodiments, the antibody does not bind, or only minimally binds a monomethylated antigen wherein the monomethylated antigen is a histone H1.0 peptide or histone H1.0 protein comprising a monomethylated lysine residue, wherein the lysine residue corresponds to K166, K172, K174, K175, K177, and/or K180 of a human histone H1.0 protein. In some embodiments, the antibody does not bind, or only minimally binds a trimethylated antigen wherein the trimethylated antigen is a histone H1.0 peptide or histone H1.0 protein comprising a trimethylated lysine residue, wherein the lysine residue corresponds to K166, K172, K174, K175, K177, and/or K180 of a human histone H1.0 protein. In some embodiments, the antibody binds the dimethylated antigen in any medium. In some embodiments, the antibody is a monoclonal antibody. In some embodiments, the antibody is a polyclonal antibody. In some embodiments, the antibody is at least 2-fold more specific for the dimethylated antigen, than a monomethylated antigen, wherein the monomethylated antigen comprises a monomethylated lysine residue, and wherein the lysine residue corresponds to K180 of a human histone H1.0 protein. In some embodiments, the antibody is labeled. In some embodiments, the antibody is biotinylated. In some embodiments, the antibody is attached to solid surface. In some embodiments, the antibody attached a bead, column, resin, or a microplate.

In another aspect, provided herein is a complex comprising a histone H1.0 peptide and a methyltransferase enzyme, wherein the complex is in vitro. In some embodiments, the H1.0 peptide comprises a sequence selected from the group consisting of SEQ ID NOs:36-68. In some embodiments, the methyltransferase enzyme is G9A methyltransferase enzyme. In some embodiments, the methyltransferase enzyme is GLP methyltransferase enzyme.

BRIEF DESCRIPTION OF THE DRAWINGS

FIGS. 4A-4C show that H1.0K180me2 is released from chromatin upon genotoxic stress induced senescence (FIG. 4A) and is secreted out of the cells into the extracellular matrix/cellular media (FIGS. 4B, 4C), as measured by using an H1.0K180me2 antibody of the invention.

FIG. 5A shows that exposure of mice to ionizing radiation induces increased levels of circulating H1.0 K180me2 in mouse serum. FIG. 5A and FIG. 5B show a slot blot analysis of the presence (FIG. 5A) and quantification (FIG. 5B) of H1.0K180me2, using antibodies specific for the H1.0K180me2 epitope in the serum. FIG. 5C shows a western blot analysis of presence of H1.0K180me2 epitope levels, using antibodies specific for the H1.0K180me2 epitope, in mouse serum after X-ray irradiation (7 Gy).

FIG. 6B shows that by using an H1.0K180me2 peptide, autoantibodies against the H1.0K180me2 epitope can be measured in plasma, urine, and saliva.

FIG. 6D shows a schematic representation and steps for measuring IgM autoantibodies using a labeled H1.0K180me2 peptide, under test and normalization conditions.

FIG. 6E shows the results of measurements of total IgMs and a standard curve of anti-IgM molar concentration versus the optical density (O.D.) at 450 nm. The IgM concentration is inferred from the curve. Box plots show total IgM concentrations, demonstrating that total IgM levels do not discriminate between individuals with and without Alzheimer's disease (AD).

FIG. 6F is a schematic representation of the use of an indirect ELISA assay for the measurements and quantification of antiH1.0K180me2 IgM autoantibodies, using a labeled H1.0K180me2 peptide.

FIG. 6G shows a standard curve of anti-IgG molar concentration versus the optical density (O.D.) at 450 nm. The IgM concentration can be inferred from the curve.

FIG. 6H demonstrates the utility of measurements of IgM autoantibodies directed to H1.0K180me2 as biomarkers of Alzheimer's disease (figures show raw non-normalized data).

FIG. 6I demonstrates the utility of measurements of IgM autoantibodies to H1.0K180me2 as biomarkers of Alzheimer's disease (figures show data normalized to total IgM levels).

FIG. 9B is a tabular representation of efficiency of methylation of G9 and GLP methylatransferases.

FIGS. 15A-15B show the siRNA knockdown of G9A in human adipocyte derived stem cells (hADSCs) (FIG. 15B) led to a reduction in H1.0K180me2 levels upon bleomycin treatment (FIG. 15A).

DETAILED DESCRIPTION

Figure 1A:
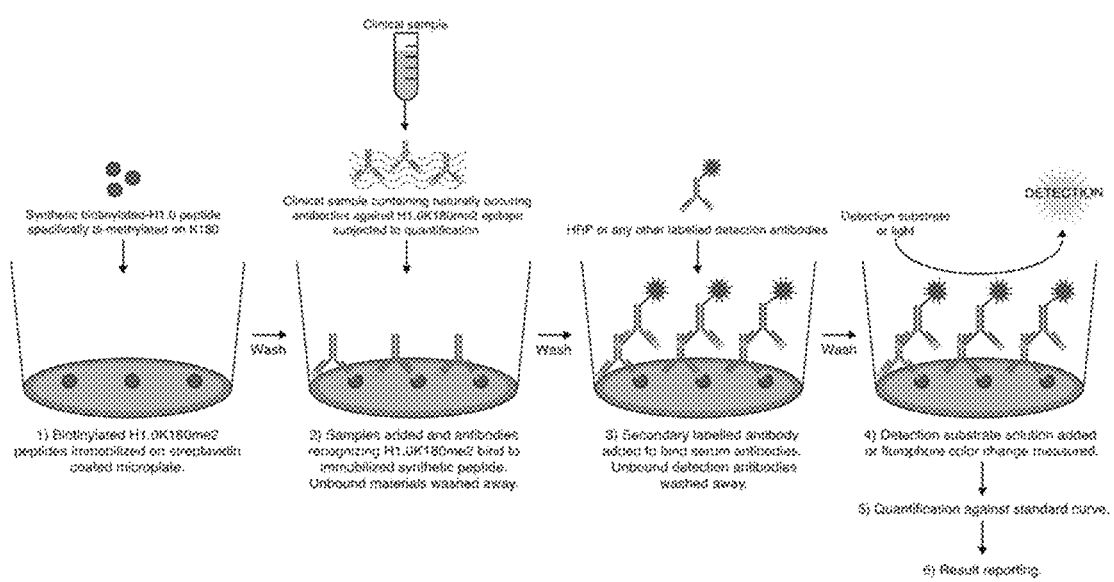
FIG. 1A shows the use of biotinylated H1.0K180me2 peptides in an indirect assay for the detection and quantification of H1.0K180me2 autoantibodies in samples of bodily fluids.

Provided herein are compositions and methods for dimethylating a full length histone H1.0 protein at lysine residue 180 (K180) as well as compositions and methods for dimethylating a peptide fragment of the full length histone H1.0 protein at a lysine corresponding to the K180 residue. The produced dimethylated proteins and peptides find many uses including, but not limited to, molecular diagnostics, therapeutics, the monitoring of therapeutic regimens, patient stratification, and drug screening, as detailed herein. Also provided herein are antibodies that specifically bind the histone H1.0 protein dimethylated at lysine residue 180 (K180) and specifically bind the histone H1.0 peptide dimethylated at a lysine residue corresponding to K180.

Generally, the terms "antigen," "peptide," "polypeptide," and "protein" used herein to refer to a polymer of amino acids, and unless otherwise specified, include atypical amino acids that can function in a similar manner to naturally occurring amino acids.

I. Dimethylated Proteins and Peptides

A full length histone H1.0 protein comprising a dimethylated lysine at a residue corresponding to K180 of the human H1.0 protein is referred to herein as an "H1.0K180me2 protein". Residue positions in the H1.0 protein discussed herein are identified with respect to a reference H1.0 human amino acid sequence. The human H1.0 histone protein used to identify residue positions is NCBI Reference Sequence: NP_005309.1 and can be accessed at http://www.ncbi.nlm.nih.gov/protein/NP_005309.1. In this case, a reference to "H1.0 residue Lysine 180" or "H1.0K180" or "K180" identifies a residue that, in human histone H1.0, is the 180$^{th}$ amino acid from the N-terminus, wherein the methionine is the first residue. The 180$^{th}$ residue is a lysine (K) in human H1.0. Those of skill in the art appreciate that this residue can have a different position in H1 proteins from different species or in different isoforms and, indeed, may be a different amino acid.

Table 1 provides the 194-amino acid sequence of the full length human H1.0 protein (NCBI Reference Sequence: NP_005309.1), numbered sequentially from 1-194 (SEQ ID NO:1). The K180 residue is shown as "K*" in SEQ ID NO:1.

TABLE 1

| Full Length Sequence of Human H1.0 Protein |
| --- |
| 1 MTENSTSAPA AKPKRAKASK KSTDHPKYSD MIVAAIQAEK NRAGSSRQSI QKYIKSHYKV |
| 61 GENADSQIKL SIKRLVTTGV LKQTKGVGAS GSFRLAKSDE PKKSVAFKKT KKEIKKVATP |
| 121 KKASKPKKAA SKAPTKKPKA TPVKKAKKKL AATPKKAKKP KTVKAKPVKA SKPKKAKPVK* |
| 181 PKAKSSAKRA GKKK (SEQ ID NO: 1) |

Use of the term K180 herein refers to the residue corresponding to K180 of the human H1.0 protein. Similarly, the term K172, refers to the residue corresponding to K172 of the human H1.0 protein, and the like.

An H1.0 protein or peptide fragment thereof comprising the dimethylated K180 residue, may be referred to herein as being an H1.0K180me2 antigen or having the H1.0K180me2 epitope. The antigen may be referred to as a dimethylated antigen.

Table 2 provides the 194-amino acid sequence of the full length human H1.0 protein, numbered sequentially from 1-194 comprising a dimethylated K180 (SEQ ID NO:1). The K180me2 residue is shown as K(me2) in SEQ ID NO:2 and other sequences provided herein. This protein is referred to as the H1.0K180me2 protein.

TABLE 2

| Full Length Sequence of Human H1.0 Protein Dimethylated at K180 |
| --- |
| 1 MTENSTSAPA AKPKRAKASK KSTDHPKYSD MIVAAIQAEK NRAGSSRQSI QKYIKSHYKV |
| 61 GENADSQIKL SIKRLVTTGV LKQTKGVGAS GSFRLAKSDE PKKSVAFKKT KKEIKKVATP |
| 121 KKASKPKKAA SKAPTKKPKA TPVKKAKKKL AATPKKAKKP KTVKAKPVKA |
| 171 SKPKKAKPVK(me2) PKAKSSAKRA GKKK (SEQ ID NO: 2) |

Any peptide fragment of the H1.0 protein retaining the dimethylated lysine corresponding to K180, is referred to herein as a "H1.0K180me2 peptide". It can also be referred to as the H1.0K180me2 antibody binding peptide, or an anti-H1.0K180me2 binding peptide, because of its ability to bind to antibodies that specifically recognize an H1.0K180me2 antigen.

Figure 3:
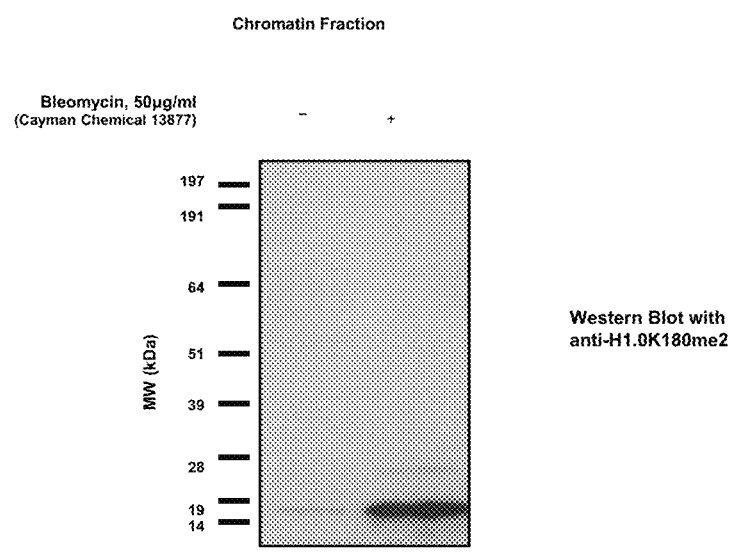
FIG. 3 shows the dimethylation of H1.0K180 on chromatin induced by DNA damage, as measured by western blot analysis, using an H1.0K180me2 antibody.
Figure 4A:
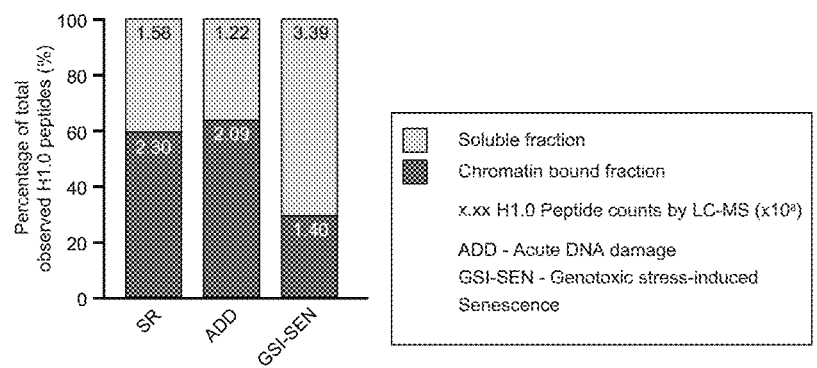
Figure 4B:
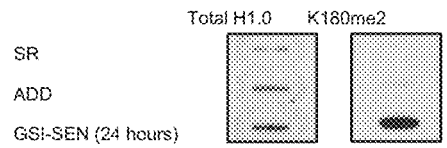
Figure 5A:
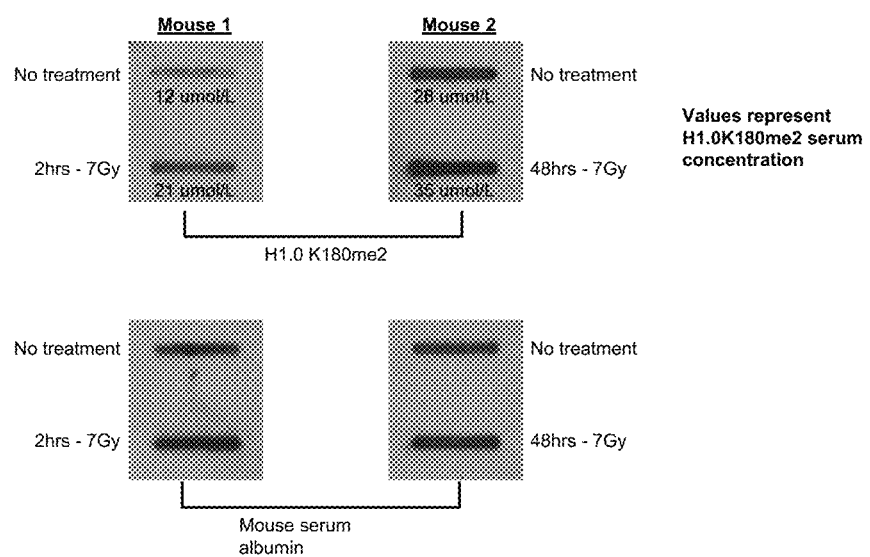
FIGS. 5A-5C show the effect of ionizing radiation on H1.0K180me2 levels.
Figure 5B:
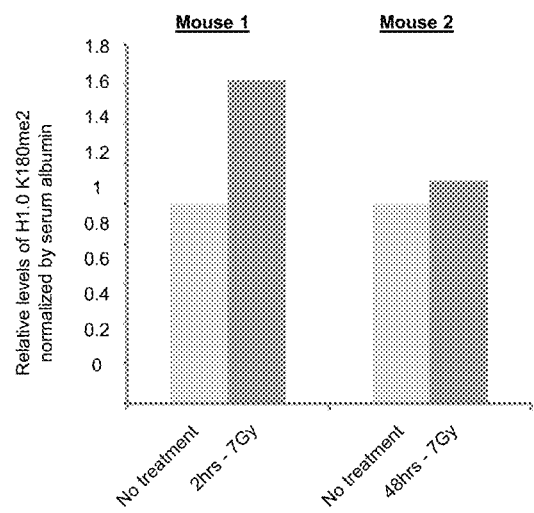
Figure 5C:
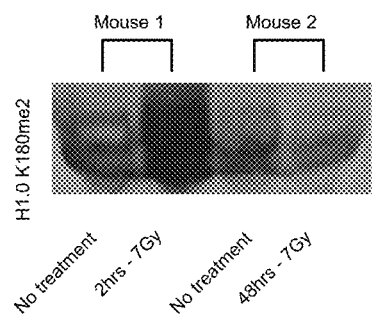

In some embodiments, expounded upon further herein, the H1.0K180me2 proteins and H1.0K180me2 peptides provided herein are useful for the indirect detection of pathophysiologies (schematically provided in FIG. 1A). A number of pathophysiologies, including Alzheimer's disease, DNA damage, genotoxic stress, and radiation damage, result in the production of the H1.0K180me2 biomarker. By way of example, H1.0K180me2 is found on chromatin, immediately after DNA damage by bleomycin, a DNA damaging agent (FIG. 3). It is also observed that H1.0K180me2 is released from chromatin upon genotoxic stress-induced senescence GSI-SEN (FIG. 4A) and is secreted out of the cells in to the extracellular space (FIG. 4B, 4C). Exposure to ionizing radiation induces increased levels of circulating H1.0K180me2 in mouse serum (FIGS. 5A-5C). There is a change in levels of H1.0K180me2 (FIG. 6A) in Alzheimer's disease patients. It has been identified by the inventors that monitoring H1.0K180me2 appearance following drug treatments, provide the basis for drug screening applications—FIG. 7 shows appearance of H1.0K180me2 in human adipose derived stem cells after bleomycin treatment (a DNA damaging agent), revealing that everolimus, a derivative of rapamycin (an approved mTOR Kinase Inhibitor), blocks H1.0K180me2 appearance.

A number of pathophysiologies, including Alzheimer's disease, DNA damage, genotoxic stress, and radiation damage, result in the generation of autoantibodies in response to the H1.0K180me2 produced. For example, there is a change in levels of autoantibody levels (autoantibodies to H1.0K180me2; FIG. 6C) in Alzheimer's disease patients.

Thus in some embodiments, the H1.0K180me2 proteins and H1.0K180me2 peptides provided herein allow for the measurement and quantification of autoantibodies generated in response. Measurement of the binding of H1.0K180me2 peptides to these autoantibodies, provides for quantification of the autoantibodies. Quantification of the autoantibodies, in turn, provides for the indirect measurement of the production of an H1.0K180me2 antigen, indicative of a number of pathophysiologies.

Figure 1B:
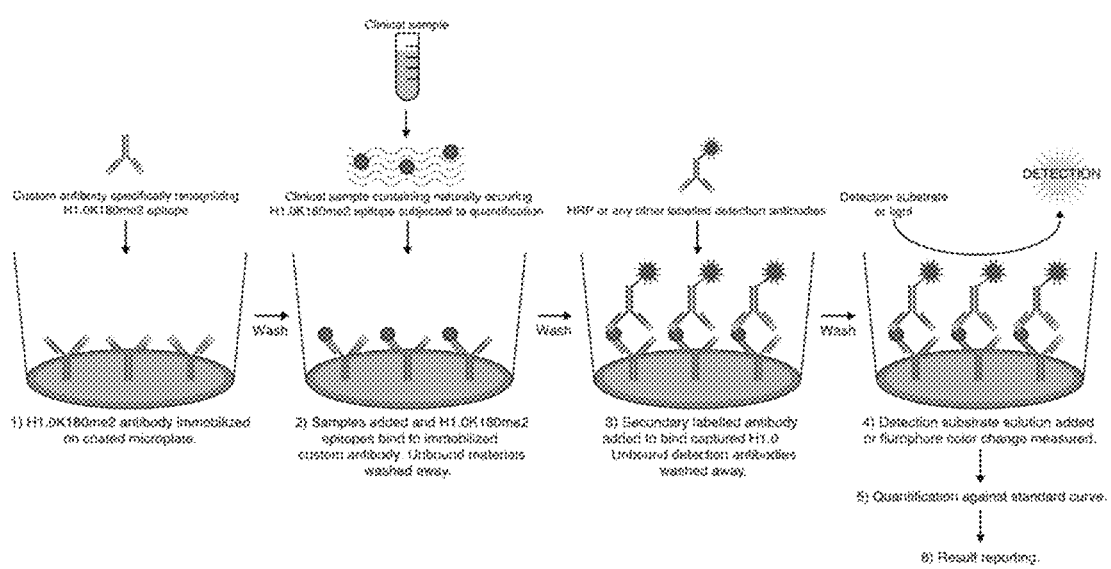
FIG. 1B shows the use of a labeled H1.0K180me2 protein or peptide (as a reference standard) to generate a standard curve (step 5), in a direct assay. This is for the detection and quantification of the H1.0K180me2 antigen (using H1.0K180me2 antibodies that bind to H1.0K180me2 antigen) in samples of bodily fluids.

In other embodiments, also expounded upon further herein, the H1.0K180me2 protein and H1.0K180me2 peptides provided herein are useful for use as a reference standard in methods that directly measure the levels of an H1.0K180me2 antigen generated in pathophysiological conditions (schematically provided in FIG. 1B). Because H1.0K180me2 is a marker of a number of pathophysiologies, H1.0K180me2 antibodies may be utilized for the detection of this biomarker. Thus, the H1.0K180me2 proteins and H1.0K180me2 peptides (e.g. labeled H1.0K180me2 proteins and H1.0K180me2 peptides) provided herein may be included in kits and methods as a reference standard or positive control to ensure the H1.0K180me2 antibodies are indeed binding their target.

II. Production of Dimethylated Protein and Peptides

As above, H1.0K180me2 proteins and peptides provided herein are useful both in the detection of pathophysiologies, and for inclusion as a reference standard in methods incorporating a quantitative assessment of H1.0K180me2 antigen presence. Provided herein are compositions and methods for the synthetic production of H1.0 proteins/peptides carrying only a dimethylated K180 residue.

In vitro methylation of protein or peptides traditionally poses challenges of specificity (e.g. specificity of the substrate to be methylated; and control of the same). Provided herein are compositions and methods for specifically dimethylating a histone H1.0 protein at lysine residue 180 (K180) (H1.0 with a K180me2) and specifically dimethylating a H1.0K180me2 peptide at a lysine corresponding to K180.

A. Production of H1.0K180me2 Peptides

The H1.0K180me2 peptides are useful both in the indirect detection of pathophysiologies, and for inclusion as a reference standard for the quantification of the data in methods including, but not limited to (1) molecular diagnostics of at least DNA damage, genotoxic stress (e.g. associated with environmental exposure), radiation exposure, chemotherapy and immunotherapy with an antibody bearing a DNA-damaging payload, radiation therapy, and Alzheimer's disease, (2) monitoring therapeutic regimens and patient stratification, (3) drug screening and (4) therapeutic use.

The H1.0K180me2 peptides provided herein range from 5-193 amino acids (aa) long. In various embodiments, the length of the H1.0K180me2 peptide is 5aa, 6aa, 7aa, 8aa, 9aa, 10aa, 11aa, 12aa, 13aa, 14aa, 15aa, 16aa, 17aa, 18aa, 19aa, 20aa, 21aa, 22aa, 23aa, 24aa, 25aa, 26aa, 27aa, 28aa, 29aa, or 30aa. In certain exemplary embodiments, the length of the H1.0K180me2 peptide is 15aa, 16aa, 17aa, 18aa, 19aa, or 20aa.

Listed in Table 3 are exemplary H1.0K180me2 peptides that can be synthetically produced (e.g. produced in vitro) using the methods and compositions described herein. In some embodiments, the H1.0K180me2 peptides of the invention comprise one of the sequences selected from those presented in Table 3. In some embodiments, the H1.0K180me2 peptide consists of one of the sequences selected from those presented in Table 3. In an exemplary embodiment, the H1.0K180me2 peptide comprises the sequence of SEQ ID NO:3, SEQ ID NO:4, or SEQ ID NO:5. In an exemplary embodiment, the H1.0K180me2 peptide consists of the sequence of SEQ ID NO:3, SEQ ID NO:4, or SEQ ID NO:5. The peptides provided in Table 3 can further comprise a label, e.g. biotin.

TABLE 3

| H1.0K180me2 Peptides | |
|---|---|
| AKPVKASKPKKAKPVK(me2)PK | (SEQ ID NO: 3) |
| KPVKASKPKKAKPVK(me2)PK | (SEQ ID NO: 4) |
| PVKASKPKKAKPVK(me2)PK | (SEQ ID NO: 5) |
| VKASKPKKAKPVK(me2)PK | (SEQ ID NO: 6) |
| KASKPKKAKPVK(me2)PK | (SEQ ID NO: 7) |
| ASKPKKAKPVK(me2)PK | (SEQ ID NO: 8) |
| SKPKKAKPVK(me2)PK | (SEQ ID NO: 9) |
| KPKKAKPVK(me2)PK | (SEQ ID NO: 10) |
| PKKAKPVK(me2)PK | (SEQ ID NO: 11) |
| KKAKPVK(me2)PK | (SEQ ID NO: 12) |
| KAKPVK(me2)PK | (SEQ ID NO: 13) |
| AKPVKASKPKKAKPVK(me2)P | (SEQ ID NO: 14) |
| KPVKASKPKKAKPVK(me2)P | (SEQ ID NO: 15) |
| PVKASKPKKAKPVK(me2)P | (SEQ ID NO: 16) |
| VKASKPKKAKPVK(me2)P | (SEQ ID NO: 17) |
| KASKPKKAKPVK(me2)P | (SEQ ID NO: 18) |
| ASKPKKAKPVK(me2)P | (SEQ ID NO: 19) |
| SKPKKAKPVK(me2)P | (SEQ ID NO: 20) |

TABLE 3-continued

H1.0K180me2 Peptides

| | |
|---|---|
| KPKKAKPVK(me2)P | (SEQ ID NO: 21) |
| PKKAKPVK(me2)P | (SEQ ID NO: 22) |
| KKAKPVK(me2)P | (SEQ ID NO: 23) |
| KAKPVK(me2)P | (SEQ ID NO: 24) |
| AKPVKASKPKKAKPVK(me2) | (SEQ ID NO: 25) |
| KPVKASKPKKAKPVK(me2) | (SEQ ID NO: 26) |
| PVKASKPKKAKPVK(me2) | (SEQ ID NO: 27) |
| VKASKPKKAKPVK(me2) | (SEQ ID NO: 28) |
| KASKPKKAKPVK(me2) | (SEQ ID NO: 29) |
| ASKPKKAKPVK(me2) | (SEQ ID NO: 30) |
| SKPKKAKPVK(me2) | (SEQ ID NO: 31) |
| KPKKAKPVK(me2) | (SEQ ID NO: 32) |
| PKKAKPVK(me2) | (SEQ ID NO: 33) |
| KKAKPVK(me2) | (SEQ ID NO: 34) |
| KAKPVK(me2) | (SEQ ID NO: 35) |

Provided herein are methods for the in vitro methylation (e.g. in vitro production) of H1.0K180me2 peptides (synthetically produced H1.0K180me2 peptides). Generally the method comprises contacting a peptide with a G9A methyltransferase enzyme or a G9A-like protein (GLP) methyltransferase enzyme and a methyl donor under conditions that allow for the specific dimethylation of a lysine residue corresponding to K180 of the histone H1.0 protein (in vitro methylation). In various embodiments, the H1.0 peptide comprises a sequence selected from the group of sequences presented in Table 4. In related embodiments, the peptide is a sequence selected from the group of sequences presented in Table 4.

The non-methylated peptides used for methylation may be synthetically produced or produced using methods familiar to those with skill in the art.

TABLE 4

H1.0 Peptides for In vitro Methylation

| | |
|---|---|
| AKPVKASKPKKAKPVKPK | (SEQ ID NO: 36) |
| KPVKASKPKKAKPVKPK | (SEQ ID NO: 37) |
| PVKASKPKKAKPVKPK | (SEQ ID NO: 38) |
| VKASKPKKAKPVKPK | (SEQ ID NO: 39) |
| KASKPKKAKPVKPK | (SEQ ID NO: 40) |
| ASKPKKAKPVKPK | (SEQ ID NO: 41) |
| SKPKKAKPVKPK | (SEQ ID NO: 42) |
| KPKKAKPVKPK | (SEQ ID NO: 43) |
| PKKAKPVKPK | (SEQ ID NO: 44) |
| KKAKPVKPK | (SEQ ID NO: 45) |

TABLE 4-continued

H1.0 Peptides for In vitro Methylation

| | |
|---|---|
| KAKPVKPK | (SEQ ID NO: 46) |
| AKPVKASKPKKAKPVKP | (SEQ ID NO: 47) |
| KPVKASKPKKAKPVKP | (SEQ ID NO: 48) |
| PVKASKPKKAKPVKP | (SEQ ID NO: 49) |
| VKASKPKKAKPVKP | (SEQ ID NO: 50) |
| KASKPKKAKPVKP | (SEQ ID NO: 51) |
| ASKPKKAKPVKP | (SEQ ID NO: 52) |
| SKPKKAKPVKP | (SEQ ID NO: 53) |
| KPKKAKPVKP | (SEQ ID NO: 54) |
| PKKAKPVKP | (SEQ ID NO: 55) |
| KKAKPVKP | (SEQ ID NO: 56) |
| KAKPVKP | (SEQ ID NO: 57) |
| AKPVKASKPKKAKPVK | (SEQ ID NO: 58) |
| KPVKASKPKKAKPVK | (SEQ ID NO: 59) |
| PVKASKPKKAKPVK | (SEQ ID NO: 60) |
| VKASKPKKAKPVK | (SEQ ID NO: 61) |
| KASKPKKAKPVK | (SEQ ID NO: 62) |
| ASKPKKAKPVK | (SEQ ID NO: 63) |
| SKPKKAKPVK | (SEQ ID NO: 64) |
| KPKKAKPVK | (SEQ ID NO: 65) |
| PKKAKPVK | (SEQ ID NO: 66) |
| KKAKPVK | (SEQ ID NO: 67) |
| KAKPVK | (SEQ ID NO: 68) |

In some embodiments, provided herein is an in vitro method for dimethylating a histone H1.0 peptide comprising contacting the peptide with a methyltransferase enzyme and a methyl donor under conditions that produce a specifically dimethylated peptide, wherein the peptide is specifically dimethylated at a lysine residue corresponding to K180 of a human histone H1.0 protein, and wherein the methyltransferase enzyme is G9A methyltransferase or GLP methyltransferase.

In some embodiments of the methods for the in vitro production of H1.0K180me2 peptide, the G9A methyltransferase may be recombinant G9A methyltransferase, a purified G9A mammalian methyltransferase, a human G9A methyltransferase, a mouse G9A methyltransferase, or the like. The G9A methyltransferase includes enzymatically active orthologs, chimeras and artificially or naturally produced isoforms containing enzymatic domains.

In some embodiments of the methods for the in vitro production of H1.0K180me2 peptide, the GLP methyltransferase may be recombinant GLP methyltransferase, a purified GLP mammalian methyltransferase, a human GLP methyltransferase, a mouse GLP methyltransferase, or the like. The GLP methyltransferase includes enzymatically active orthologs, chimeras and artificially or naturally produced isoforms containing enzymatic domains.

In embodiments of the methods for the in vitro methylation or in vitro production of H1.0K180me2 peptide, the methyl donor may be S-Adenosyl-L-Methionine (SAM).

In embodiments of the methods for the in vitro production of H1.0K180me2 peptide, the contacting may be done in a methylation buffer.

In embodiments of the methods for the in vitro production of H1.0K180me2 peptide, the peptide may comprise a label (e.g. biotin) prior to the methylation.

In embodiments of the methods for the in vitro production of H1.0K180me2 peptide, the peptide maybe conjugated with a label (e.g. biotin) after the methylation.

In embodiments of the methods for the in vitro methylation of the peptide substrate, greater than 50%, 60%, 65%, 70%, 75%, 80%, 85%, 90%, 95%, 99%, or even 99.9% of the product comprises K180me2. Likewise, in embodiments of the methods for the in vitro production of H1.0K180me2 peptide, in various embodiments, less than 50%, 40%, 30%, 25%, 20%, 15%, 10%, 5%, 4%, 3%, 2%, 1%, 0.5%, or less than 0.35% of the product also contains other methylated residues (e.g. K172me1, K172me2, K172me3, K174me1, K174me2, K174me3, K175me1, K175me2, K175me3, K177me1, K177me2, K177me3, K166me1, K166me2, K166me3, K180me1,and/or K180me3). In exemplary embodiments, less than 0.35% of the product having the K180me2 also comprises K174me3, K175me3, and K177me1; less than 1.25% of the product having the K180me2 also comprises K166me1; and less than 1.04% of the product having the K180me2 comprises K174me1 and K180me3.

In some embodiments an H1.0K180me2 peptide binds an antibody that is specific for an H1.0K180me2 antigen (an H1.0K180me2 antibody). Provided herein, is an antibody that specifically binds a dimethylated antigen, wherein the dimethylated antigen is a histone H1.0 peptide comprising a dimethylated lysine residue, wherein the lysine residue corresponds to K180 of a human histone H1.0 protein.

In certain embodiments, an H1.0K180me2 peptide binds an H1.0K180me2 antibody with a dissociation constant (Kd) of about 0.0001 nM to about 1 µM. For example, Kd of the peptide may be about 1 µM, about 100 nM, about 50 nM, about 10 nM, about 5 nM, about 1 nM, about 0.5 nM, about 0.1 nM, about 0.05 nM, about 0.01 nM, about 0.005 nM, about 0.001 nM, about 0.0005 nM, or even about 0.0001 nM.

In some embodiments, an H1.0K180me2 peptide binds only a human H1.0K180me2 antibody. In some embodiments, an H1.0K180me2 peptide is cross reactive with an H1.0K180me2 antibody from other species.

In some embodiments, an H1.0K180me2 peptide only binds H1.0K180me2 antibody and exhibits little or no binding to H1.0K180me1 or H1.0K180me3 antibodies.

In some embodiments, the binding preference of an H1.0K180me2 peptide (e.g., affinity) for the H1.0K180me2 antibody is generally at least about 2-fold, about 5-fold, or at least about 10-, 20-, 50-, $10^2$-, $10^3$-, $10^4$, $10^5$, or $10^6$-fold over a non-specific target antibody (e.g. a randomly generated antibody).

The H1.0K180me2 peptides can be equally specific/selective for antibodies carrying a payload (e.g. including but not limited to a radionuclide, a cytotoxin, a chemotherapeutic agent, a drug, a pro-drug, a toxin, an enzyme, an immunomodulator, a pro-apoptotic agent, a cytokine, a hormone, an antagonist, an agonist or a receptor decoy).

The H1.0K180me2 peptides provided herein may be further conjugated for a variety of purposes including, but not limited to, for use in detection, diagnostics, visualization, quantification, sorting, therapeutics, and for use in biological assays.

In some embodiments, an unmethylated H1.0 peptide or the H1.0K180me2 peptide is comprises a label (either before or after the methylation), for example a detectable label, a spin label, a colorimetric label, a radioactive label, an enzymatic label, a fluorescent label, a magnetic label, or the like.

In some embodiments, the peptide comprises (e.g. conjugated to) a detectable label either before or after methylation. The detectable group may be any material having a detectable physical or chemical property, for example detectable by spectroscopic, photochemical, biochemical, immunochemical, fluorescent, electrical, optical or chemical means. Useful labels in the present invention include, but are not limited to, magnetic beads (e.g. DYNABEADS®), fluorescent dyes (e.g., fluorescein isothiocyanate, red, rhodamine, and the like), radiolabels (e.g., $^3$H, $^{125}$I, $^{35}$S, $^{14}$C, or $^{32}$P), enzymes (e.g., LacZ, CAT, horseradish peroxidase, alkaline phosphatase and others, commonly used as detectable enzymes, either as marker gene products or in an ELISA), biotin, avidin, or streptavidin and colorimetric labels such as colloidal gold colored glass or plastic (e.g. polystyrene, polypropylene, latex, etc.) beads, and nanoparticles. In an exemplary embodiment, an H1.0K180me2 peptide is biotinylated.

The labels provided herein may be coupled directly or indirectly to the desired component of the assay according to methods well known in the art. As indicated above, a wide variety of labels may be used, with the choice of label depending on the sensitivity required, ease of conjugation of the compound, stability requirements, available instrumentation, and disposal provisions. Labels are often attached by indirect means. Generally, a ligand molecule (e.g., biotin) is covalently bound to the molecule. The ligand then binds to an anti-ligand (e.g., streptavidin) molecule which is either inherently detectable or covalently bound to a signal system, such as a detectable enzyme, a fluorescent compound, or a chemiluminescent compound. Alternatively, any haptenic or antigenic compound may be used in combination with an antibody. Components may also be conjugated directly to signal-generating compounds, e.g., by conjugation with an enzyme or fluorophore. Enzymes of interest as labels may primarily be hydrolases, particularly phosphatases, esterases and glycosidases, or oxitranscription factoreductases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol.

In some embodiments, an H1.0K180me2 peptide is conjugated or attached to a solid surface, for example a bead (e.g. a magnetic, glass or plastic bead), column, resin, or a microplate. In specific embodiments, an H1.0K180me2 peptide is coated onto the microplate. In some embodiments, an H1.0K180me2 peptide is conjugated to an effector molecule including, but not limited to, a radionuclide, a cytotoxin, a chemotherapeutic agent, a drug, a pro-drug, a toxin, an enzyme, an immunomodulator, a pro-apoptotic agent, a cytokine, a hormone, an oligonucleotide, an antisense molecule, a siRNA, or a second antibody.

In some embodiments, provided herein is a complex comprising a histone H1.0 peptide and a methyltransferase enzyme, wherein the complex is in vitro (e.g. in a test tube, in a reaction container, in a reaction chamber, and the like). In some embodiments, the H1.0 peptide comprises a sequence selected from the group consisting of SEQ ID NOs:36-68. In some embodiments, the methyltransferase enzyme is G9A methyltransferase enzyme. In some embodiments, the methyltransferase enzyme is GLP methyltransferase enzyme.

B. Production of H1.0K180me2 Proteins

The full length H1.0K180me2 proteins described herein are useful both in the detection of pathophysiologies, and for inclusion as a reference standard in methods including, but not limited to (1) molecular diagnostics of at least DNA damage, genotoxic stress (e.g. associated with environmental exposure), radiation exposure, chemotherapy and immunotherapy with an antibody bearing a DNA-damaging payload, radiation therapy, and Alzheimer's disease, (2) monitoring therapeutic regimens and patient stratification, (3) drug screening, and (4) used as therapeutics.

In some embodiments, provided herein are in vitro methods for dimethylating a histone H1.0 protein comprising contacting the protein with a methyltransferase enzyme and a methyl donor under conditions that produce a specifically dimethylated protein, wherein the protein is specifically dimethylated at a lysine residue corresponding to K180 of a human histone H1.0 protein, and wherein the methyltransferase enzyme is a G9A methyltransferase or GLP methyltransferase. The resulting product is a synthetic H1.0K180me2 protein.

In some embodiments, provided herein are methods for in vitro production of an H1.0K180me2 protein. In one embodiment, the method comprises contacting a full length H1.0 protein with a G9A methyltransferase enzyme and a methyl donor under conditions that allow for the specific dimethylation the K180 residue. The G9A methyltransferase includes enzymatically active orthologs, chimeras and artificially or naturally produced isoforms containing enzymatic domains.

In some embodiments, provided herein are methods for the in vitro production of an H1.0K180me2 protein. In one embodiment, the method comprises contacting a full length H1.0 protein with a GLP methyltransferase enzyme and a methyl donor under conditions that allow for the specific dimethylation the K180 residue. The GLP methyltransferase includes enzymatically active orthologs, chimeras and artificially or naturally produced isoforms containing enzymatic domains.

The full length H1.0 unmethylated protein substrate used for the in vitro methylation may be isolated, synthetically produced, or recombinantly produced, using methods familiar to those with skill in the art. Provided herein are nucleic acids encoding the H1.0K180me2 protein. Also provided herein are vectors comprising any of the nucleic acids encoding for the H1.0K180me2 proteins provided herein.

In some embodiments of the methods for the in vitro production of an H1.0K180me2 protein, the G9A methyltransferase may be a recombinant G9A methyltransferase, a purified G9A mammalian methyltransferase, a human G9A methyltransferase, a mouse G9A methyltransferase, or the like.

In some embodiments of the methods for the in vitro production of H1.0K180me2 protein, the GLP methyltransferase may be a recombinant GLP methyltransferase, a purified GLP mammalian methyltransferase, a human GLP methyltransferase, or a mouse GLP methyltransferase.

In some embodiments of the methods for the in vitro production of H1.0K180me2 protein, the protein comprises may comprise label (e.g. biotin) prior to the methylation.

In some embodiments of the methods for the in vitro production of H1.0K180me2 protein, the protein maybe conjugated with a label (e.g. biotin) after the methylation.

In some embodiments of the methods for the in vitro methylation or in vitro production of H1.0K180me2 protein, the methyl donor is S-Adenosyl-L-Methionine.

In some embodiments of the methods for the in vitro production of H1.0K180me2 protein, the contacting is done in a methylation buffer.

In embodiments of the methods for the in vitro methylation of the protein substrate, greater than 50%, 60%, 65%, 70%, 75%, 80%, 85%, 90%, 95%, 96%, 97%, 98%, 99%, or even 99.9% of the product can comprise K180me2. Likewise, in some embodiments of the methods for the in vitro production of H1.0K180me2 protein, less than 50%, 40%, 30%, 25%, 20%, 15%, 10%, 5%, 4%, 3%, 2%, 1%, 0.5%, or less than 0.35% of the product also contains other methylated residues (e.g. K172me1, K172me2, K172me3, K174me1, K174me2, K174me3, K175me1, K175me2, K175me3, K177me1, K177me2, K177me3, K166me1, K166me2, K166me3, K180me1, and/or K180me3). In exemplary embodiments, less than 0.35% of the product having the K180me2 also comprises K174me3, K175me3, and K177me1; less than 1.25% of the product having the K180me2 also comprises K166me1; and/or less than 1.04% of the product having the K180me2 comprises K174me1 and K180me3.

Provided herein is an antibody that specifically binds a dimethylated antigen, wherein the dimethylated antigen is found in a histone H1.0 protein comprising a dimethylated lysine residue, wherein the lysine residue corresponds to K180 of a human histone H1.0 protein.

In some embodiments the H1.0K180me2 protein is selective for an antibody that is specific for H1.0K180me2 (H1.0K180me2 antibody). In some embodiments, the peptide binds an antibody that is non-specific for H1.0K180me2.

In certain embodiments, the H1.0K180me2 proteins bind an H1.0K180me2 antibody with a dissociation constant (Kd) of about 0.0001 nM to about 1 µM. For example, the Kd may be about 1 µM, about 100 nM, about 50 nM, about 10 nM, about 5 nM, about 1 nM, about 0.5 nM, about 0.1 nM, about 0.05 nM, about 0.01 nM, about 0.005 nM, about 0.001 nM, about 0.0005 nM, or even about 0.0001 nM.

In some embodiments, the H1.0K180me2 protein is specific for the anti-human H1.0K180me2 antibody. In some embodiments, an H1.0K180me2 protein is cross reactive with an H1.0K180me2 antibody from other species.

In some embodiments, the H1.0K180me2 protein is selective for the H1.0K180me2 antibody and exhibits little or no binding to H1.0K180me1 or H1.0K180me3 antibodies.

In some embodiments, the binding preference of the H1.0K180me2 protein (e.g., affinity) for the H1.0K180me2 antibody is generally at least about 2-fold, about 5-fold, or at least about 10-, 20-, 50-, $10^2$-, $10^3$-, $10^4$, $10^5$, or $10^6$-fold over a non-specific target antibody (e.g. a randomly generated antibody).

The H1.0K180me2 proteins provided herein may be further conjugated for a variety of purposes including, but not limited to, for use in detection, diagnostics, visualization, quantification, sorting, therapeutics, and for use in biological assays.

In some embodiments, the H1.0 proteins (H1.0 substrate before methylation) or the H1.0K180me2 proteins (after methylation) comprises (e.g. is further conjugated to) a label, for example a detectable label, a spin label, a colorimetric label, a radioactive label, an enzymatic label, a fluorescent label, a magnetic label, or the like.

In some embodiments, the H1.0 substrate (before methylation) and H1.0K180me2 proteins (after methylation) are conjugated to a detectable label. The detectable group may be any material having a detectable physical or chemical property, for example detectable by spectroscopic, photochemical, biochemical, immunochemical, fluorescent, electrical, optical or chemical means. Useful labels in the present invention include, but are not limited to, magnetic beads (e.g. DYNABEADS®), fluorescent dyes (e.g., fluorescein isothiocyanate, red, rhodamine, and the like), radiolabels (e.g., $^3$H, $^{125}$I, $^{35}$S, $^{14}$C, or $^{32}$P), enzymes (e.g., LacZ, CAT, horseradish peroxidase, alkaline phosphatase and others, commonly used as detectable enzymes, either as marker gene products or in an ELISA), biotin, avidin, or streptavidin and colorimetric labels such as colloidal gold colored glass or plastic (e.g. polystyrene, polypropylene, latex, etc.) beads, and nanoparticles. In an exemplary embodiment, an H1.0K180me2 peptide is biotinylated.

The labels provided herein may be coupled directly or indirectly to the desired component of the assay according to methods well known in the art. As indicated above, a wide variety of labels may be used, with the choice of label depending on the sensitivity required, ease of conjugation of the compound, stability requirements, available instrumentation, and disposal provisions. Labels are often attached by indirect means. Generally, a ligand molecule (e.g., biotin) is covalently bound to the molecule. The ligand then binds to an anti-ligand (e.g., streptavidin) molecule which is either inherently detectable or covalently bound to a signal system, such as a detectable enzyme, a fluorescent compound, or a chemiluminescent compound. A number of ligands and anti-ligands may be used. Where a ligand has a natural anti-ligand, for example, biotin, it may be used in conjunction with the labeled, naturally occurring anti-ligands. Alternatively, any haptenic or antigenic compound may be used in combination with an antibody. Components may also be conjugated directly to signal-generating compounds, e.g., by conjugation with an enzyme or fluorophore. Enzymes of interest as labels may primarily be hydrolases, particularly phosphatases, esterases and glycosidases, or oxitranscription factoreductases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol.

In some embodiments, the H1.0K180me2 proteins are conjugated or attached to a solid surface, for example a bead (e.g. a magnetic, glass or plastic bead), column, resin, or a microplate. In specific embodiments, the H1.0K180me2 protein is coated onto the microplate. In some embodiments, the H1.0K180me2 protein is conjugated to an effector molecule including, but not limited to, a radionuclide, a cytotoxin, a chemotherapeutic agent, a drug, a pro-drug, a toxin, an enzyme, an immunomodulator, a pro-apoptotic agent, a cytokine, a hormone, a decoy receptor, an agonist, an oligonucleotide, an antisense molecule, a siRNA, or a second antibody.

III. Use of Dimethylated Proteins and Peptides

A. Use in Detection of Naturally Occurring H1.0K180me2 Autoantibodies—Indirect Quantification of H1.0K180me2

The H1.0K180me2 protein and peptide compositions provided herein may be used for the detection and measurement of naturally occurring autoantibodies specific to an H1.0K180me2 protein or fragment thereof. Specifically provided herein are the H1.0K180me2 proteins and H1.0K180me2 peptides, wherein they bind an antibody that specifically binds a histone H1.0 protein comprising a dimethylated lysine at residue 180 (K180) or the antibody binds a fragment of a histone H1.0 protein comprising a dimethylated lysine corresponding to K180. The H1.0K180me2 proteins and the H1.0K180me2 peptides provided herein may be useful for the detection of a marker that is indicative of the presence of H1.0K180me2 in a sample. The H1.0K180me2 peptides may comprise the sequence selected from those presented in Table 3. The H1.0K180me2 proteins may comprise the sequence provided in Table 2.

B. Use as a Reference Standard in the Direct Detection and Quantification of H1.0K180me2

In another embodiment, the H1.0K180me2 protein and H1.0K180me2 peptides provided herein are useful as a reference standard in methods that directly measure the naturally occurring levels of an H1.0K180me2 antigen. As discovered herein, because H1.0K180me2 is a marker of a number of pathophysiologies, H1.0K180me2 antibodies may be utilized for the detection of this biomarker. Thus, the H1.0K180me2 protein and peptides provided herein may be included in kits and methods as a reference standard or positive control to ensure the H1.0K180me2 antibodies are indeed binding their target.

Direct detection of H1.0K180me2 may be carried out using antibodies specific and/or selective for H1.0K180me2 antibodies; such antibodies are provided herein. FIG. 1B schematically illustrates such detection.

The H1.0K180me2 protein and peptides are produced and may be concentrated (for example using lyophilization), quantified, and included in kits (e.g. ELISA kits) as a reference standard.

C. Use in Molecular Diagnostics, Personalized Medicine, Drug Screening, and Therapeutics The direct and indirect detection and quantification assays described herein are useful for detecting replicative senescence, DNA damage, genotoxic stress (e.g. associated with environmental exposure), radiation exposure, Alzheimer's disease, biological aging, and are useful for monitoring therapeutic regimens (e.g. chemotherapy, radiation therapy, immunotherapy), useful for drug screening, useful for therapeutics, and useful for stratification of patients as responders or non-responders to drug treatments aimed to restore cell viability, prevent DNA damage, increase cellular metabolism and autophagy, inhibit cellular senescence and block insoluble protein waste accumulation in cellular cytoplasm, neutralize or sensitize immune responses.

As above, H1.0K180me2 may be detected directly using an H1.0K180me2 antibody, an assay in which H1.0K180me2 protein and peptides are used as reference standards. Alternatively, H1.0K180me2 may be detected indirectly by using an H1.0K180me2 protein or peptides, which bind autoantibodies that are generated in pathophysiologies.

Depending on the application, detection may be in vivo, in vitro, ex vivo, in situ, or in a cell-free system.

Detection may be carried out on any biological sample. Biological samples include, but are not limited to whole blood, plasma, serum, saliva, urine, feces, synovial fluid, cerebrospinal fluid, bronchial lavage, ascites fluid, bone marrow aspirate, pleural effusion, tissue, cells, a biopsy, interstitial fluid, lymphatic fluid, or fractions thereof derived from an individual. In some embodiments, the biological sample comprises cells and the cells are in culture, in a suspension, on a slide, in an intact tissue, or in preparation ready for a FACs analysis.

Biological samples are obtained from individuals. As used herein, an individual refers to any animal classified as a mammal, including humans, domestic and farm animals, and zoo, sport, or pet animals, such as dogs, horses, rabbits, cattle, pigs, hamsters, gerbils, mice, ferrets, rats, cats, and the like. Individuals may be male or female. In one embodiment, the individual is a female. In one embodiment, the individual is a male.

Biological samples are obtained according to standard methods well known to those of skill in the art. The sample is optionally pretreated as necessary by dilution in an appropriate buffer solution or concentrated, if desired. Any of a number of standard aqueous buffer solutions, employing one of a variety of buffers, such as phosphate, TRIS, or the like, at physiological pH may be used.

The direct detection methods described herein may be used to quantify the concentration of H1.0K180me2 in the biological sample, using the H1.0K180me2 protein or peptides to establish a standard curve. In some embodiments, an H1.0K180me2 peptide of the invention may be used in tandem, for example, as a positive control or as competitor in a competitive immunoassay, and may be labeled or not, depending on the format of the assay to be carried out.

The indirect detection methods described herein may also be used to quantify the concentration of H1.0K180me2 autoantibodies in the biological sample. In some embodiments, an H1.0K180me2 antibody of the invention may be used in tandem, for example, as a positive control or as competitor in a competitive immunoassay, and may be labeled or not, depending on the format of the assay to be carried out.

One of skill will appreciate that in many embodiments, it may be necessary to compare the determined concentrations of an H1.0K180me2 antigen or autoantibodies to an H1.0K180me2 antigen to a control. The relative comparison may allow, for example, the determination of whether an individual has, or is at risk of developing a disease (e.g. Alzheimer's disease or whether the individual is responsive, or may be responsive to a particular treatment (e.g. an Alzheimer's disease treatment; or a treatment with a rapalogue). Controls may be age-matched controls; sex-matched controls; age- and sex-matched controls; or a standard developed over time that reflects the compilation of a predetermined standard. The comparisons may also be made to a sample from the same individual prior to a treatment (e.g. with an Alzheimer's disease treatment or rapalogue treatment) or prior to an exposure to a genotoxic stressor, DNA-damaging agent, or radiation, for example. The comparisons may also be made to a sample from the same individual from an unaffected area, for example from an unaffected tissue.

One of skill will appreciate that it is often desirable to reduce non-specific binding in immunoassays and during analyte detection. Where the assay involves H1.0K180me2 antibodies or H1.0K180me2 protein or peptides, immobilized on a solid substrate, it may be desirable to minimize the amount of non-specific binding to the substrate. Methods of reducing such non-specific binding are known to those of skill in the art. Typically, this involves coating the substrate with a proteinaceous composition. In some embodiments, protein compositions such as bovine serum albumin (BSA), nonfat powdered milk, and gelatin may be utilized.

Detection may be carried out by any of number of means well known to those of skill in the art. The H1.0K180me2 protein and peptides provided herein are readily used in a variety of immunoassays. These immunoassays include, but are not limited to enzyme-linked immunosorbent assay (ELISA), Western blot, radioimmunoassay (MA), flow cytometry, lateral flow immunoassay, slot blot, magnetic immunoassay, a radioimmunoassay, indirect immunofluorescence assay, direct immunofluorescence assay, surround Optical Fiber Immunoassay (SOFIA), spectrophotometry, radiography, electrophoresis, immunoelectrophoresis, capillary electrophoresis, high performance liquid chromatography (HPLC), thin layer chromatography (TLC), hyperdiffusion chromatography, fluid or gel precipitation reactions, immunodiffusion, spectrometry, mass spectrometry, quantitative mass-spectrometry, any type of multiplex assay, and any type of microfluidic assay. Methods of detecting labels are well known to those of skill in the art.

In another embodiment, H1.0K180me2 protein or peptide may be used as a therapeutic to decrease levels or neutralize activity of naturally occurring autoantibodies to this antigen in the blood, and other body fluids or tissue, as well as sensitize the immune response.

IV. Antibodies Specific for Dimethylated Proteins and Peptides

A. H1.0K180me2 Antibodies

Provided herein are antibodies that specifically bind a dimethylated antigen, wherein the dimethylated antigen is a histone H1.0 peptide or histone H1.0 protein comprising a dimethylated lysine residue, wherein the lysine residue corresponds to K180 of a human histone H1.0 protein. This dimethylated antigen is the H1.0K180me2 antigen, also referred to as the H1.0K180me2 epitope. These antibodies specifically bind the histone H1.0 protein dimethylated at lysine residue 180 (K180) and fragments thereof. These antibodies specifically bind the dimethylated antigen (specifically bind to an H1.0K180me2 epitope) and require the presence of the dimethyl group at K180 for binding. The terms "anti-H1.0K180me2" or "H1.0K180me2 antibody" or "anti-H1.0K180me2 antibody" interchangeably refer to these antibodies.

The term "antibody" as used herein throughout is in the broadest sense and includes, but is not limited to, a monoclonal antibody, polyclonal antibody, human antibody, humanized antibody, non-human antibody, chimeric antibody, bispecific antibody, multi-specific antibody, polyfunctional antigen-binding fragment (e.g Fab fragment, a Fab'2 fragment, a CDR or a ScFv), antibody-drug conjugates, and other antibody fragments that retain specificity for an H1.0K180me2 antigen. In some embodiments, the antibody is a single chain antibody that retains the specificity for an H1.0K180me2 antigen.

It is appreciated that an H1.0K180me2 antigen may be chromatin bound, or may be released from the chromatin into the nucleus, cytoplasm, or the extracellular space. The antibodies provided herein can bind extracellular H1.0K180me2, cellular membrane bound H1.0K180me2, MHC-I and MHC-II bound-H1.0K180me2, and/or intracellular H1.0K180me2. If intracellular, an H1.0K180me2 antigen may be further bound to chromatin, or released in the nucleus, released from the nucleus into the cytoplasmic space, or further localized in a cytoplasmic sub-structure.

In some embodiments, the antibody is a neutralizing antibody, and the antibody neutralizes one or more biological activities of H1.0K180me2. For example, the antibody may bind extracellular H1.0K180me2 and neutralize any binding or signaling activity it may possess.

The antibodies provided herein may be of any immunoglobulin type such as IgG, IgA, IgE, IgD, or IgM. In some embodiments, the antibody is of the IgG subtype and may be an IgG1 antibody, an IgG2 antibody, an IgG3 antibody, or an IgG4 antibody.

The H1.0K180me2 antibodies may be specific for dimethylated H1.0 proteins or fragments thereof, from any species, e.g., any eukaryote. In some embodiments, the H1.0K180me2 antibody is specific for human H1.0K180me2. In some embodiments, the H1.0K180me2 antibody is cross reactive with H1.0K180me2 from other species.

The H1.0K180me2 antibodies provided herein specifically bind a dimethylated antigen, wherein the dimethylated antigen is a histone H1.0 peptide or histone H1.0 protein comprising a dimethylated lysine residue, wherein the lysine residue corresponds to K180 of a human histone H1.0 protein. In some embodiments, the dimethylated antigen does not comprise any other lysine residues that are methylated. The antibodies provided herein bind H1.0K180me2 proteins and H1.0K180me2 peptides with specificity. In some embodiments, these antibodies bind H1.0K180me2 proteins and H1.0K180me2 peptides with specificity and selectivity.

In some embodiments, the H1.0K180me2 antibody does not bind, or only minimally binds a dimethylated antigen wherein the dimethylated antigen is a histone H1.0 peptide or histone H1.0 protein comprising a dimethylated lysine residue, wherein the lysine residue corresponds to K166, K172, K174, K175, and/or K177 of a human histone H1.0 protein.

In some embodiments, the H1.0K180me2 antibody does not bind, or only minimally binds, an antigen that comprises one or more of the following residues: K172me1, K172me2, K172me3, K174me1, K174me2, K174me3, K175me1, K175me2, K175me3, K177me1, K177me2, K177me3, K166me1, K166me2, K166me3, K180me1, and/or K180me3.

In some embodiments, the H1.0K180me2 antibody does not bind, or only minimally binds, an antigen that comprises a dimethylated K180 residue, but also comprises one or more of the following residues: K172me1, K172me2, K172me3, K174me1, K174me2, K174me3, K175me1, K175me2, K175me3, K177me1, K177me2, K177me3, K166me1, K166me2, K166me3, K180me1, and/or K180me3.

In some embodiments, the H1.0K180me2 antibody does not bind, or only minimally binds a monomethylated antigen wherein the monomethylated antigen is a histone H1.0 peptide or histone H1.0 protein comprising a monomethylated lysine residue, wherein the lysine residue corresponds to K166, K172, K174, K175, K177, and/or K180 of a human histone H1.0 protein.

In some embodiments, the H1.0K180me2 antibody does not bind, or only minimally binds a trimethylated antigen wherein the trimethylated antigen is a histone H1.0 peptide or histone H1.0 protein comprising a trimethylated lysine residue, wherein the lysine residue corresponds to K166, K172, K174, K175, K177, and/or K180 of a human histone H1.0 protein.

The H1.0K180me2 antibody binds the dimethylated antigen in any medium.

A variety of immunoassay formats may be used to select antibodies specifically immunoreactive with H1.0K180me2. For example, solid-phase ELISA immunoassays may be used to select monoclonal antibodies specific to H1.0K180me2 (see, e.g., Harlow and Lane (1988) Antibodies, A Laboratory Manual, Cold Spring Harbor Publications, New York, for a description of immunoassay formats and conditions that may be used to determine specific immunoreactivity).

Production of the antibodies provided herein may be by any method known to those with skill in the art. For example, in some embodiments, the antibodies are produced by recombinant cells engineered to express the desired VH, VL and constant domains of the desired antibody. In some embodiments the antibodies are produced by hybridomas.

In some embodiments, any peptide comprising an H1.0K180me2 antigen, optionally linked to the immunogenic carrier, is used for immunization using standard protocols. In specific embodiments, a peptide comprising a sequence from those presented in Table 3, optionally linked to the immunogenic carrier, is used for immunization using standard protocols. In an exemplary embodiment, a peptide comprising AKPVKASKPKKAKPVK$^{me2}$PK (SEQ ID NO:3), optionally linked to the immunogenic carrier, and is used for immunization using standard protocols. The quality and titre of generated antibodies may be assessed using techniques known to those in the art.

In some embodiments, the H1.0K180me2 antibody exists in a high titer.

In some embodiments, the H1.0K180me2 antibody is an affinity purified antibody.

In some embodiments, the H1.0K180me2 antibody displays at least 1.5-fold, 2-fold, 2.5-fold, 2.7-fold, 5-fold, or even 10-fold more specificity (e.g. binding efficiency, binding preference, affinity) for the dimethylated antigen at K180 (H1.0K180me2 antigen), than a monomethylated antigen at K180 (H1.0K180me1 antigen). (FIG. 2C) In some embodiments the specificity for an H1.0K180me2 antigen is generally at least about 2-fold, about 5-fold, or at least about 10-, 20-, 50-, $10^2$-, $10^3$-, $10^4$, $10^5$, or $10^6$-fold over a non-specific target molecule (e.g. a randomly generated molecule lacking the specifically recognized site(s)), over a monomethylated K180 residue, over a trimethylated K180 residue, or over an H1.0 protein methylated at any other residue.

In some embodiments, the binding efficiency of an H1.0K180me2 antibody is monitored by an ELISA assay. In some embodiments, the antibody is at least 2.7-fold more efficient at binding an H1.0K180me2 peptide than an H1.0K180me1 peptide. In some embodiments, 1 molecule of the antibody recognizes 1 out of 117 molecules of an H1.0K180me2 peptide, but only 1 out of 316 molecules of an H1.0K180me1 peptide.

In certain embodiments, an antibody provided herein has a dissociation constant (Kd) of range of 0.0001 nM to 1 μM. For example, Kd of the antibody may be about 1 μM, about 100 nM, about 50 nM, about 10 nM, about 5 nM, about 1 nM, about 0.5 nM, about 0.1 nM, about 0.05 nM, about 0.01 nM, about 0.005 nM, about 0.001 nM, about 0.0005 nM, or even about 0.0001 nM.

The H1.0K180me2 antibodies provided herein may be further conjugated for a variety of purposes including, but not limited to, for use in detection, diagnostics, visualization, quantification, sorting, therapeutics, and for use in biological assays.

In some embodiments, the H1.0K180me2 antibodies comprise a label (e.g. are conjugated to a label), for example a detectable label, a spin label, a colorimetric label, a radioactive label, an enzymatic label, a fluorescent label, or a magnetic label.

In some embodiments, the H1.0K180me2 antibodies comprise a label (e.g. are conjugated to a label). The detectable group may be any material having a detectable physical or chemical property, for example detectable by spectroscopic, photochemical, biochemical, immunochemical, fluorescent, electrical, optical or chemical means. Useful labels in the present invention include, but are not limited to, magnetic beads (e.g. DYNABEADS®), fluorescent dyes (e.g., fluorescein isothiocyanate, red, rhodamine, and the like), radiolabels (e.g., $^3$H, $^{125}$I, $^{35}$S, $^{14}$C, or $^{32}$P), enzymes (e.g., LacZ, CAT, horseradish peroxidase, alkaline phosphatase and others, commonly used as detectable enzymes, either as marker gene products or in an ELISA), biotin, avidin, or streptavidin and colorimetric labels such as colloidal gold colored glass or plastic (e.g. polystyrene, polypropylene, latex, etc.) beads, and nanoparticles. In an exemplary embodiment, an H1.0K180me2 antibody is biotinylated.

The H1.0K180me2 antibody labels provided herein may be coupled directly or indirectly to the desired component of the assay according to methods well known in the art. As indicated above, a wide variety of labels may be used, with the choice of label depending on the sensitivity required, ease of conjugation of the compound, stability requirements, available instrumentation, and disposal provisions. Labels are often attached by indirect means. Generally, a ligand molecule (e.g., biotin) is covalently bound to the molecule. The ligand then binds to an anti-ligand (e.g., streptavidin) molecule which is either inherently detectable or covalently bound to a signal system, such as a detectable enzyme, a fluorescent compound, or a chemiluminescent compound. A number of ligands and anti-ligands may be used. Where a ligand has a natural anti-ligand, for example, biotin, it may be used in conjunction with the labeled, naturally occurring anti-ligands. Alternatively, any haptenic or antigenic compound may be used in combination with an antibody. Components may also be conjugated directly to signal-generating compounds, e.g., by conjugation with an enzyme or fluorophore. Enzymes of interest as labels may primarily be hydrolases, particularly phosphatases, esterases and glycosidases, or oxitranscription factoreductases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol.

In some embodiments, the H1.0K180me2 antibodies are conjugated or attached to a solid surface, for example a bead (e.g. a magnetic, glass or plastic bead), column, resin, or a microplate. In specific embodiments, the H1.0K180me2 antibody is coated onto the microplate. In some embodiments, the H1.0K180me2 antibody is conjugated to an effector molecule including, but not limited to, a radionuclide, a cytotoxin, a chemotherapeutic agent, a drug, a pro-drug, a toxin, an enzyme, an immunomodulator, a pro-apoptotic agent, a cytokine, a hormone, an agonist, an antagonist, a receptor decoy, an oligonucleotide, an antisense molecule, a siRNA, or a second antibody.

The inventive compositions described herein also include nucleic acids encoding the antibodies, vectors comprising any of the nucleic acids encoding the antibodies, and host cells comprising any such vectors.

As those of skill in the art readily appreciate, antibodies can also be prepared by any of a number of commercial services.

B. Exemplary Uses for H1.0K180me2 Antibodies

FIG. 1B shows the use of antibody in order to detect an antigen comprising the H1.0K180me2 epitope in an in vitro assay.

The use of an H1.0k180me2 antibody that specifically binds an H1.0K180me2 antigen shows that an H1.0K180me2 antigen is a biomarker of acute DNA damage. (FIG. 3).

The use of an H1.0k180me2 antibody that specifically binds an H1.0K180me2 antigen shows that an H1.0K180me2 antigen is released from chromatin upon senescence, and is secreted into the extracellular matrix. (FIGS. 4A-4C).

The use of an H1.0k180me2 antibody that specifically binds an H1.0K180me2 antigen shows that exposure to ionizing radiation induces the levels of an H1.0K180me2 antigen in the serum. (FIG. 5A-5C).

The use of an H1.0k180me2 antibody that specifically binds an H1.0K180me2 antigen levels in the brain and serum are an indication of Alzheimer's disease. (FIGS. 6A-6M).

V. Kits and Other Articles of Manufacture

Provided herein are kits (e.g. diagnostic kits) useful for the detection of H1.0K180me2 antigen. In some embodiments, the kit comprises one or more H1.0K180me2 protein or H1.0K180me2 peptides as described herein. In certain embodiments, the proteins or peptides are labeled. In certain embodiments, the proteins or peptides are attached to a solid surface (e.g. a bead, column, resin, or a microplate).

The kits may also include additional components to facilitate the particular application for which the kit is designed. Thus, for example, where a kit contains an H1.0K180me2 protein or peptide that is labeled, the kit may additionally contain methods of detecting the label (e.g., enzyme substrates for enzymatic labels, filter sets to detect fluorescent labels, appropriate secondary labels, or the like). The kits may additionally include buffers and other reagents routinely used for the practice of a particular method.

An exemplary kit useful in an immunoassay to detect H1.0K180me2 antigen in a sample, may comprise an H1.0K180me2 protein or peptide. Such a kit may be useful for indirect detection of an H1.0K180me2 in a sample (by detection of the autoantibodies produced in response to the antigen).

Another exemplary kit useful in an immunoassay to detect H1.0K180me2 in a sample, may comprise an H1.0K180me2 antibody, and may include an H1.0K180me2 protein or peptide as a reference standard. This peptide may be employed, for example, as a positive control or as competitor in a competitive immunoassay, and may be labeled or not, depending on the format of the assay to be carried out. Such a kit may be useful for the direct detection of an H1.0K180me2 in a sample (detection achieved by the binding of the H1.0K180me2 antibody to the H1.0K180me2 in the sample).

Another exemplary kit useful in an immunoassay to detect H1.0K180me2 in a sample, may comprise an H1.0K180me2 antibody. Such a kit may be useful for therapeutics or for the direct detection of an H1.0K180me2 antigen in a sample.

In various exemplary embodiments, the kits described herein may be used for the detection of Alzheimer's disease, radiation exposure, exposure to a genotoxic stressors, or exposure to a DNA damaging agent; for drug screening; for therapeutics monitoring (e.g. chemotherapy, immunotherapy, radiation treatment); for therapeutics; for patient stratification; or for treatment selection.

In addition, the kits may optionally include instructional materials for carrying out any of the methods described herein. While the instructional materials typically comprise written or printed materials, they are not limited to such. Any medium capable of storing such instructions and communicating them to an end user is contemplated herein. Such media include, but are not limited to, electronic storage media (e.g., magnetic discs, tapes, cartridges, chips), optical media (e.g., CD ROM), and the like. Such media may include addresses to internet sites that provide such instructional materials.

The following examples are included for illustrative purposes and are not intend to limit the scope of the invention.

EXAMPLES

Example 1: Materials and Methods

Provided here are materials and methods used in the subsequent examples.

In Vitro Methylation of H1.0 Protein and Peptides—Radiolabel in Vitro Methylation Assay In order to visualize methylation of H1.0 peptide by G9A methyltransferase in vitro, a methylation assay was performed incorporating a radiolabelled methyl donor, which allows for visualization of methylated peptide on a gel after autoradiography exposure. The following methylation reaction was set up in a 1.5 ml tube: 1×HMT reaction buffer (50 mM Tris-HCl, 5 mM $MgCl_2$, 4 mM dithiothreitol, pH 9.0), 10U G9A Methyltransferase (NEB, M0235S, Lot #0031201), 3.2 mM Adenosyl-L-Methionine, S-[Methyl-3H] (Perkin Elmer, NET155H, Lot #1664720), 10 µg H1.0 peptide (ThermoFisher Scientific, Biotin-AKPVKASKPK-KAKPVKPK (SEQ ID NO:69)), final volume 10 µl. A control reaction as above but without H1.0 peptide was also created. Reactions were incubated in a thermocycler at 37° C. for 1 hour. Reactions were stopped by incubating on ice for 5 minutes, and subsequently resolved on a 16.5% Tricine gel (BioRad, 4563063). Gels were soaked in 30% methanol, 5% glycerol for 30 minutes before vacuum drying at RT for 24 hours. Autoradiography analysis of dried gels with a phosphoimager (Molecular Dynamics) was then performed to assess effective methylation of H1.0 peptide with methyl-3H groups by the G9A methyltransferase. (Example 1, FIG. 8A)

Liquid Chromatography and High-Resolution Mass Spectrometry (LC-MS)

In order to identify the precise sites of methylation by G9A and GLP methyltransferases on histone H1.0, in vitro methylation assays were performed and subsequently analyzed by Liquid Chromatography and High-resolution Mass Spectrometry (LC-MS) analysis. Methylation reactions were set up using either G9A methyltransferase (NEB, M0235S, Lot #0031201) or GLP methyltransferase (Cayman Chemical, 10755). The methyl donor in each reaction was unlabeled S-Adenosyl-L-Methionine (NEB, B9003S). The H1.0 substrate in each reaction was either unmodified H1.0 peptide labeled with biotin (ThermoFisher Scientific, Biotin-AKPVKASKPKKAKPVKPK (SEQ ID NO:69)), dimethylated H1.0 peptide (ThermoFisher Scientific, Biotin-AKPVKASKPKKAKPVK$^{(me2)}$PK (SEQ ID NO:70)), or full-length recombinant human H1.0 (NEB, M2501S). Methylation reactions were set up in triplicate for each condition as follows: 1×HMT reaction buffer (50 mM Tris-HCl, 5 mM $MgCl_2$, 4 mM dithiothreitol, pH 9.0); 10U G9A or GLP Methyltransferase; 3.2 mM S-Adenosyl-L-Methionine; 500 ng unmodified or modified H1.0 peptide, or 1 µg full-length protein; final volume 10 µl. As controls, reactions were set up as above but without any methyltransferase present. All reactions were incubated in a thermocycler at 37° C. for 1 hour, and subsequently stopped by incubating on ice for 5 minutes. Samples were frozen at −80° C. prior to LC-MS analysis.

For the Liquid Chromatography and High-resolution Mass Spectrometry (LC-MS) analysis, samples were prepared as described above and about 1 µg o the product was injected onto a Thermo Scientific Easy nLC system configured with a 10 cm×100 um trap column and a 25 cm×100 um ID resolving column. Buffer A was 98% water, 2% methanol, and 0.2% formic acid. Buffer B was 10% water, 10% isopropanol, 80% acetonitrile, and 0.2% formic acid. Samples were loaded at 4 uL/min for 10 min, and a gradient from 0-45% B at 375 nL/min was run over 130 min, for a total run time of 150 min (including regeneration and sample loading). The Thermo Scientific LTQ Orbitrap Velos mass spectrometer was run in a standard Top-10 data-dependent configuration except that a higher trigger-threshold (20 K) was used to ensure that the MS2 did not interfere with the full-scan duty cycle. This ensured optimal full-scan data for quantification. MS2 fragmentation and analysis were performed in the ion trap mass analyzer. Samples were run in triplicate.

LC-MS Data Analysis

Protein identification was performed using Thermo Scientific Proteome Discoverer version 1.4 (including Sequest and Percolator algorithms) using RefSeqHuman sequence database. These searches were performed with the control reactions lacking any methyltransferase enzyme. The Percolator peptide confidence filter was set to "high". Protein quantification was performed using Pinpoint version 1.4 software. The Pinpoint quantification workflow included importing the Proteome Discoverer .msf files as spectral libraries. Identified peptides were subsequently quantified in MS .raw files using the Pinpoint peak finding, chromatographic alignment and area calculation algorithms.

Figure 9A:
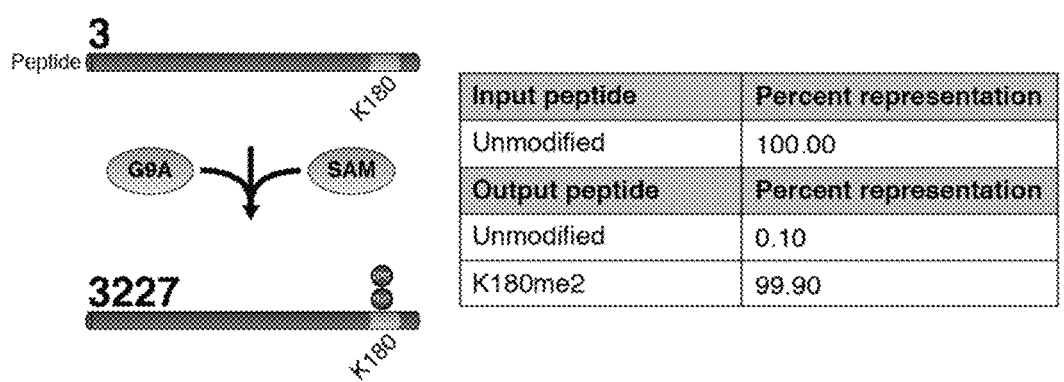
FIG. 9A shows that in the presence of unmethylated H1.0 peptide, G9A methyltransferase specifically and abundantly dimethylates H1.0K180 (99.9% of all peptides).

In order to identify the precise locations of G9A methylation on unmodified H1.0 peptide (AKPVKASKPKKAK-PVKPK (SEQ ID NO:36)), a methylation reaction was set up and the products identified by LC-MS. The methylation reaction comprised recombinant G9A, an unlabeled methyl donor (S-Adenosyl-L-Methionine), and unmodified H1.0 peptide. The methylation reaction was subsequently analyzed by LC-MS, and each spectral peak (corresponding to a peptide species in the final reaction) was identified and quantified using spectral counts. The number of "me" circles in FIG. 9A represents the methylation state of the lysine residue (mono-, di-, or tri-methylated). FIG. 9A shows that in the presence of unmethylated H1.0 peptide, G9A specifically and abundantly dimethylates H1.0K180 (99.9% of all peptides).

Culture of hADSCs

Human adipose-derived mesenchymal stem cells (hAD-SCs) used in this research were obtained commercially from Life Technologies (R7788-115) and the American Type Culture Collection, ATCC (PCS-500-011). All cell lines were isolated from human adipose tissues obtained from three healthy adult female Caucasian donors aged 38, 45 and 49 undergoing routine liposuction procedures. Flow cytometry analysis and immunostaining analysis confirmed hADSCs were positive for CD29, CD44, CD73, CD90, CD105, and CD166, and negative for CD14, CD31, CD34, and CD45. Cell lines were confirmed capable of adipogenic, chondrogenic and osteogenic differentiation under in vitro conditions.

Isolated adipose-derived stem cell lines were grown in DMEM/F12 medium (Life Technologies, 11330-057), supplemented with 10% (v/v) Fetal Bovine Serum (FBS) and 50 U/ml penicillin/streptomycin at 37° C./5% $CO_2$. Cumulative population doublings (PD) were calculated as PD=log(N/NO)×3.33 across the multiple passages as a function of the number of days of growth in culture, where NO is the number of cells plated in the flask and N is the number of cells harvested at this passage. hADSCs PD 4-10 for self-renewing populations (SR) and PD 41-46 for replicatively senescent populations (REP-SEN) were used in all experiments.

Surface Marker Characterization.

Five×$10^5$ cells each were incubated for 30 min on ice in the dark with fluorochrome-conjugated antibodies (CD31, CD44, CD45 and CD105; Invitrogen) in PBS with 1% BSA (Sigma), washed and analyzed in a Guava EasyCyte Mini System (Guava Technologies, Millipore). Data analysis was performed using FlowJo software (Tree Star, Ashland, Oreg.).

Senescence Induction and Assessment

For replicative senescence, hADSCs were grown in culture until reaching replicative exhaustion (PD 41-46). For acute DNA damage conditions, SR hADSCs (PD 4-10) were treated with 50μg/ml bloemycin sulfate (Cayman Chemical, 13877) in growth media for 2 hours. For genotoxic stress induced senescence, SR hADSCs (PD 4-10) were treated with 50 μg/ml bloemycin sulfate (Cayman Chemical, 13877) in growth media for 2 hours then washed with PBS and given fresh growth media without bloemycin. Cells were then grown for 3 days before collection.

To assess cellular senescence, cells were scored for senescence markers, including growth arrest, SA-β-gal activity, and the presence of persistent DNA-damage foci. The assay for monitoring the expression of pH-dependent senescence-associated β-galactosidase activity (SA-β-Gal) was performed as described in manufacturer's kit (BioVision). The cultured hADSCs were fixed with fixative solution for 15 minutes at room temperature, washed with twice with PBS and stained with X-Gal containing staining supplement overnight at 37° C. The cells were washed twice with PBS, and the images were captured using light microscopy (Leica, DMiL). DNA-damage foci were assessed by immunostaining for γH2AX foci.

Antibodies

Primary antibodies used: Anti-H1.0K180me2, 1:100 dilution, rabbit polyclonal, Aviva Systems Biology. Anti-H1.0 total, 1:500 dilution, EMD Millipore MABE446. Anti-γH2AX (Ser139Ph), 1:500-1000 dilution, EMD Millipore 05-636. Anti-beta-actin, 1:2000, Abcam ab6276. Anti-poly-(ADP)-ribose, 1:500, Enzo Life Sciences ALX-804-220-R100. Anti-G9A, 1:500, Bethyl Laboratories A300-933A. Anti-GLP, 1:500, Bethyl Laboratories A301-643A. Anti-H3K9me2, 1:1000, Abcam A301-643A.

Secondary antibodies used: Goat-anti-mouse-HRP, 1:4000, Biorad 1706516. Goat-anti-rabbit-HRP, 1:4000, Biorad 1706515. Goat-anti-human-HRP, 1:4000, Biorad 1721050. AlexaFluor-488-donkey anti-mouse, 1:5000, Life Technologies A-21202. AlexaFluor-488-donkey anti-rabbit, 1:5000, Life Technologies A-21206. AlexaFluor-555-donkey anti-mouse, 1:5000, Life Technologies A-31570. AlexaFluor-555-donkey anti-rabbit, 1:5000, Life Technologies A-31572.

Western Blot

Material for western blot analysis (cultured cells or tissue) was lysed in ice-cold RIPA lysis buffer (Thermo Scientific 89900) and sonicated using a Covaris S2 sonicator (10% duty cycle, Intensity 5, Bursts per minute 100, 120 seconds). Total protein concentration in each sample was quantified using Quick Start Bradford 1× Dye Reagent (BioRad, 5000205) following manufacturer's protocol. Samples were then mixed with NuPAGE LDS sample loading buffer (ThermoFisher, NP0007) and NuPAGE sample reducing buffer (ThermoFisher, NP0004), and heat denatured at 70° C. for 10 minutes. Proteins were separated on 4-12% precast polyacrylamide gels (ThermoFisher, NP0321) by electrophoresis and transferred to 0.45 μm nitrocellulose membrane. The membrane was blocked with 5% non-fat milk in PBS-T for 30 minutes at RT then immunoblotted with the above primary antibodies at 4° C. overnight. Proteins were detected with HRP secondary antibodies listed above for 1 hour at RT followed by ECL Western Blotting Substrate (ThermoFisher, 32106) using manufacturer's instructions. All washes between steps were with PBS-T. Membranes were imaged with Omega LUM-C imaging system (Gel Company).

Immunofluorescence

For immunofluorescence, cells were cultured and treated in chamber slides, fixed in neutral 10% formalin, and permeabilized with PBS containing 0.5% Triton X-100. After washing, the slides were blocked using PBS containing 1% BSA and 4% donkey serum. After washing, the slides were incubated with primary antibodies listed above, washed again, incubated with AlexaFluor secondary antibodies listed above, and mounted with slow-fade gold (Molecular Probes) containing DAPI (to visualize nuclei). Cells were viewed by fluorescence microscopy and images were acquired for analysis using Spotfire software (Diagnostics Instruments).

Slot Blot Analysis 0.5 μl of serum sample or known amounts of synthesized peptide were diluted in 200 μl TBS. Samples were then heat denatured at 70° C. for 10 minutes before being transferred to nitrocellulose membrane using a vacuum manifold slot blot apparatus (BioRad, 1706542). The membrane was blocked with 5% non-fat milk in PBS-T for 30 minutes at RT then immunoblotted with the above primary antibodies at 4° C. over night. Proteins were detected with HRP secondary antibodies listed above for 1 hour at RT followed by ECL Western Blotting Substrate (ThermoFisher, 32106) using manufacturers instructions. All washes between steps were with PBS-T. Membranes were imaged with Omega LUM-C imaging system (Gel Company). Slot blot bands for each sample were then quantified using ImageJ.

Proteomic Analysis

Post-translational modifications of histones were assessed by M/Z Pair Tag LC-MS. Five technical replicate injections of self-renewing and replicatively senescent hADSC lysates were processed in a full-scan optimized configuration. It was determined that the chromatography and instrument methods for optimal full scan quantitative measurements conflicted with methods of optimal fragmentation scans. Therefore the mass spectrometer's accurate mass and broad dynamic range capabilities were exploited by incorporating into analysis two distinct passes of data measurement. The first pass focused upon acquiring un-compromised and optimized full scan (MS) data for highly reproducible quantification. This first full-scan quantitative pass was used to generate an inclusion list of potentially interesting features. The inclusion list was then used for targeted fragmentation scan acquisition during a second pass for a subset of the data samples.

RNAseq Analysis

Total RNA was isolated from self-replicating and replicatively senescent cell culture samples using TRIzol reagent (Invitrogen) according to the manufacturer's protocol. Samples from two different hADSC cell lines were combined together for the relevant conditions and RNA concentrations were measured with the Qubit 2.0 fluorometer using the RNA HS Assay kit (Invitrogen, Life technologies). The ERCC RNA Spike-In Control mix (Ambion, Life Technologies) was added to total RNA for quality control analysis.

Subsequently, rRNA depletion was performed with the Low Input Ribominus Eukaryote System v2 (Ambion, Life technologies). cDNA libraries were constructed with Ion total RNA-seq kit v2 (Ambion, Life technologies), and barcoded with Ion Xpress RNA-seq barcode (Ambion, Life technologies). The size distribution and quantification of the libraries was performed with DNA HS bioanalyzer kit on a Bioanalyzer 2100 (Agilent Technologies). Library sequencing was performed on the Ion Proton System with P1 chip (Life Technologies), and each library was sequenced 3 times.

RNA-seq reads from individual Ion Proton System sequencing runs were combined for each library. Sequence reads were mapped to the reference human genome assembly hg19 (GRCh37) using the Torrent Mapping Alignment Program (TMAP, Life technologies). The quality of the RNA-seq runs for each condition was evaluated by comparing the expected counts of ERCC spike-in RNA sequences, obtained from the manufacturer's website, against the observed counts of RNA-seq tags that map to the same sequences. Initial gene expression levels were taken as the sum of exon-mapped reads for individual NCBI RefSeq gene models (c), and lowly expressed genes (read counts per million<1) were removed from subsequent analyses. For each library, individual gene expression levels were normalized using the beta-actin (ACTB) expression levels (cACTB) and the total exon length l of each gene. For library j, the beta-acting normalization factor sj was calculated as:

$$s_j = \frac{\frac{1}{n}\sum_{k=1}^{n} c_{ACTB,k}}{c_{ACTB,j}}.$$

The final normalized expression value for gene i in library j was calculated as:

$$e_{i,j} = \frac{c_{i,j} \times s_j}{l_i}$$

Drug Treatments

Bleomycin treatment: Cell growth media was supplemented with 50 µg/ml bleomycin (Cayman Chemical 13877) for 2 hours to induce DNA double strand breaks. Cells were either collected immediately post-bleomycin treatment (acute DNA damage), or grown for 3 days post-bleomycin treatment (genotoxic stress induced senescence). PARP-1 Inhibitor: Cell growth media was supplemented with 1 µM of the potent PARP-1 inhibitor AG14361 (Selleckchem S2178) for 24 hours prior to downstream analysis. Rapamycin treatment: Cell growth media was supplemented with 500nM Rapamycin (Cayman Chemical 11346) for 24 hours prior to downstream analysis or treatment. Everolimus treatment: Cell growth media was supplemented with 500 nM Everolimus (Cayman Chemical 11597) for 24 hours prior to downstream analysis or treatment. Temozolomide treatment: Cell growth media was supplemented with 50 µg/ml Temozolomide (Cayman Chemical 14163) for 2 hours prior to downstream analysis.

Analysis of H1.0K180me2 in Mice After Irradiation

Blood was collected from two 13-month-old mice via cheek puncture and serum separated using Microtainer Tubes® with SST Serum Separator (BD, 365956). The same mice were then exposed to 7 Gy ionizing radiation (in the form of X-rays). Blood was drawn again from one mouse 2 hours after irradiation, and from the other mouse 48 hours after irradiation. Serum was again separated from blood using a Microtainer Tube®. Serum from each mouse before and after irradiation was then analyzed by slot blot and western blot.

Adipose Derived Stem Cell (ADSC) Isolation from Mice

Mouse adipose derived stem cells were isolated from wild type, mice. Subcutaneous or perirenal white adipose tissue was collected and suspended in Hank's Buffered Salt Solution (HBSS), 3.5% Bovine Serum Albumin (BSA), 1% Collagenase, type II (Sigma) in 1:3 w/v ratio and shaken at 37° C. for 50 min. The cells were filtered through a 70 µm mesh cell strainer (BD Falcon #352350), treated with Red Blood Cell Lysis buffer (150 mM NH4Cl, 10 mM KHCO3, 0.1 mM EDTA, pH 7.3), and expanded ex-vivo in DMEM/F12 complete medium (DMEM/F12, 10% FBS, 100 U/ml penicillin, 100 µg/ml streptomycin, 2.5 µg/ml amphotericin B; Invitrogen) in 10% $CO_2$ at 37° C. and passaged at 80% confluency, changing medium every 72-96 hours. Cells were then used for western blot analysis as described elsewhere.

siRNA Transfection siRNA pools designed to target G9A were obtained from Qiagen (GS10919) and random scrambled siRNA pools were obtained from ThermoFisher Scientific (4390843). siRNA pools were transfected into self-replicating hADSCs using Lipofectamine 3000 (Life Technologies) following manufacturer's protocols. Cells were collected 24 hours after siRNA transfection and analyzed by qPCR or western blot.

qPCR

Cell cultures were homogenized in Trizol (Invitrogen) and total RNA was isolated using the RNeasy kit (Qiagen). The RNA was quantified with Qubit (Invirtogen) and reverse transcribed using SuperScript III following manufacturer's protocol (Invitrogen). Quantitative PCR analyses were performed in triplicate using an Applied Biosystems 7700 sequence detector with ~5 ng of cDNA, 1 µM designated primer pairs and Fast-SYBR Green PCR master mix following manufacturers protocol (Applied Biosystems). Primer pairs are listed below. The mean cycle threshold (Ct) for each gene was normalized to levels of beta-actin in the same sample (delta Ct). Unpaired two-sample t-tests were used to determine differences in mean delta Ct values between treatment groups. Where appropriate, the fold change was calculated by the delta-delta Ct method (fold=2ΔΔCt).

TABLE 5

| Primers | |
|---|---|
| GLP-Forward | 5'-AGGGGAGTGCTGACACAGAG-3' (SEQ ID NO: 71) |
| GLP-Reverse | 5'-GGGATCTTTACTGGCTGCAT-3' (SEQ ID NO: 72) |
| Beta-actin-Forward | 5'-CTCTTCCAGCCTTCCTTCCT-3' (SEQ ID NO: 73) |
| Beta-actin-Reverse | 5'-AGCACTGTGTTGGCGTACAG-3' (SEQ ID NO: 74) |
| H1.0-Forward | 5'-CTCAAGCAGACCAAAGGGGT-3' (SEQ ID NO: 75) |
| H1.0-Reverse | 5'-GGCGTGGCTACCTTCTTGAT-3' (SEQ ID NO: 76) |

TABLE 5-continued

| Primers | |
|---|---|
| H1.1-Forward | 5'-AGGCAACGGGTGCATCTAAA-3' (SEQ ID NO: 77) |
| H1.1-Reverse | 5'-GATTTCCTTGTTGCCGCAGG-3' (SEQ ID NO: 78) |
| H1.2-Forward | 5'-CAAAGAAGGCCAAGGTTGCG-3' (SEQ ID NO: 79) |
| H1.2-Reverse | 5'-CGCCTTCTTAGGCTTGACAAC-3' (SEQ ID NO: 80) |
| H1.3-Forward | 5'-AGTGGCCAAGAGTGCGAAAA-3' (SEQ ID NO: 81) |
| H1.3-Reverse | 5'-CTTCGGCTTCCCCGACTTAG-3' (SEQ ID NO: 82) |
| H1.4-Forward | 5'-ACGCTTGCCTTCAACATGTCC-3' (SEQ ID NO: 83) |
| H1.4-Reverse | 5'-AGTAATGAGCTCGGACACCG-3' (SEQ ID NO: 84) |
| H1.5-Forward | 5'-CCGGCTAAGAAGAAGGCAAC-3' (SEQ ID NO: 85) |
| H1.5-Reverse | 5'-GCTCCTTAGAAGCAGCCACA-3' (SEQ ID NO: 86) |
| G9A-Forward | 5'-TGCTGAGGCTGATGTGAGAG-3' (SEQ ID NO: 87) |
| G9A-Reverse | 5'-GGTCACACAGGTGGTTGATG-3' (SEQ ID NO: 88) |

Drug treatments

Bleomycin treatment: Cell growth media was supplemented with 50 µg/ml bleomycin (Cayman Chemical 13877) for 2 hours to induce DNA double strand breaks. Cells were either collected immediately post-bleomycin treatment (acute DNA damage), or grown for 3 days post-bleomycin treatment (genotoxic stress induced senescence). PARP-1 Inhibitor: Cell growth media was supplemented with 1 µM of the potent PARP-1 inhibitor AG14361 (Selleckchem S2178) for 24 hours prior to downstream analysis. Rapamycin treatment: Cell growth media was supplemented with 500 nM Rapamycin (Cayman Chemical 11346) for 24 hours prior to downstream analysis or treatment. Everolimus treatment: Cell growth media was supplemented with 500 nM Everolimus (Cayman Chemical 11597) for 24 hours prior to downstream analysis or treatment. Temozolomide treatment: Cell growth media was supplemented with 50 µg/ml Temozolomide (Cayman Chemical 14163) for 2 hours prior to downstream analysis.

Example 2: In Vitro Methylation with G9A and Analysis of Products

Figure 8A:
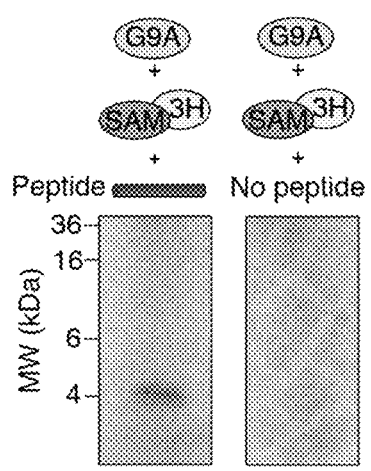
FIGS. 8A-8B show the results of the in vitro G9A methyltransferase methylation assay. The G9A methyltransferase is capable of methylating an H1.0 peptide (FIG. 8A) and is capable of methylating full length H1.0 (FIG. 8B).
Figure 8B:
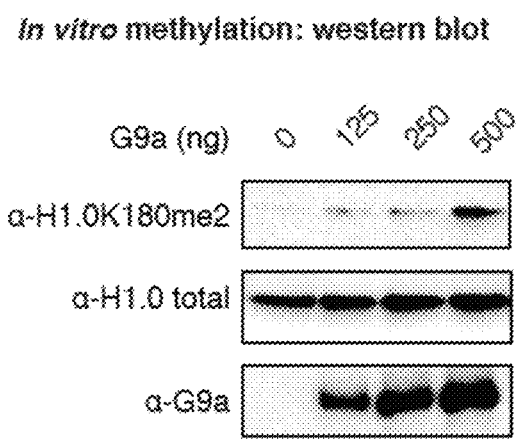

FIGS. 8A-8B show the results of this in vitro G9A methylation assay.

A G9A methyltransferase is capable of methylating an H1.0 peptide (FIG. 8A). The methylation reaction was subsequently resolved on a gel and visualized via autoradiography. The appearance of a band at 4 kDa shows that The G9A methyltransferase capable of methylating H1.0 peptide through the transfer of tritium-labeled methyl groups to the peptide, allowing for visualization. A control reaction lacking H1.0 peptide yielded no tritium-labeled products.

A G9A methyltransferase is capable of methylating a full-length recombination H1.0 (FIG. 8B). An in vitro methylation assay of recombinant full-length histone H1.0 with increasing amounts of G9A is shown in FIG. 8B. G9A is capable of dimethylating full length H1.0 at K180.

In order to identify the precise locations of G9A methylation on an unmodified H1.0 peptide (AKPVKASKPK-KAKPVKPK (SEQ ID NO:36)), a methylation reaction was set up and the products identified by LC-MS. The methylation reaction comprised recombinant G9A, an unlabeled methyl donor (S-Adenosyl-L-Methionine), and unmodified H1.0 peptide. The methylation reaction was subsequently analyzed by LC-MS, and each spectral peak (corresponding to a peptide species in the final reaction) was identified and quantified using spectral counts. The number of "me" circles in FIG. 9A represents the methylation state of the lysine residue (mono-, di-, or tri-methylated). FIG. 9A shows that in the presence of unmethylated H1.0 peptide, G9A specifically and abundantly dimethylates H1.0K180 (99.9% of all peptides).

Figure 10:
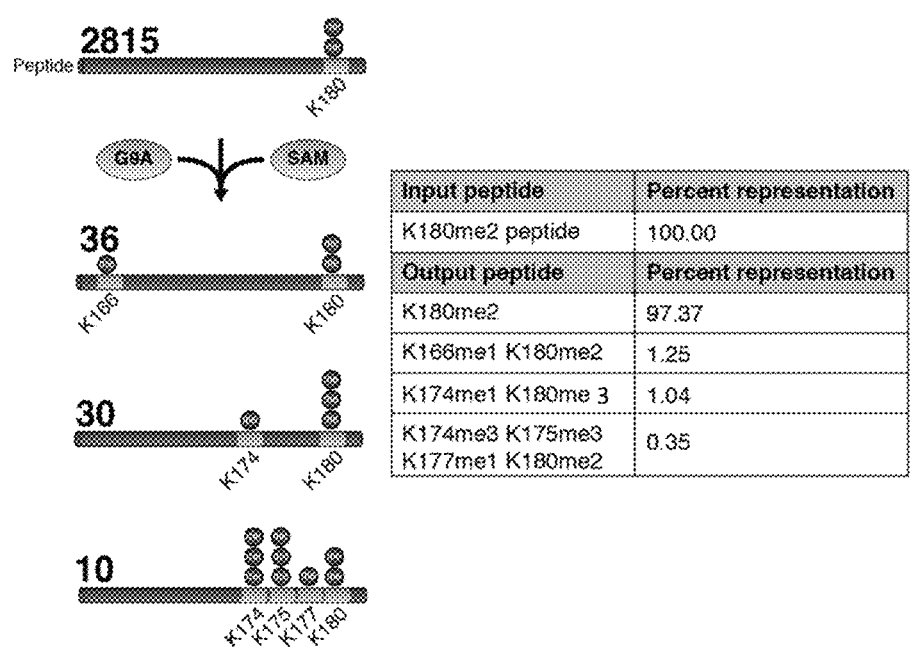
FIG. 10 shows that in the presence of dimethylated H1.0 peptide, there is minimal further methylation that takes place (only 2.64% of peptides are further methylated).

More specifically, the data demonstrate that G9A dimethylates lysine K180 but not other lysines (K166, K174, K175 or K177) present in the same peptide fragment, with an estimated methylation efficiency of about 99% (FIG. 9A and FIG. 9B). To further address the sensitivity and specificity of G9A methylation to lysine 180 of H1.0 peptide, the K180me2 peptide (H1.0 AA 165-182) was used as a substrate in similar in vitro methylation experiments. Only minor quantitates of further methylated peptide were detected: H1.0K166me1K180me2 (1.27% of the total peptide in the reaction), H1.0K174me1K180me3 (1.06% of the total peptide in the reaction) and H1.0K174me3K175me3K177me1K180me2 (0.35% of the total peptide in the reaction) as shown in FIG. 9B FIG. 10.

Figure 11:
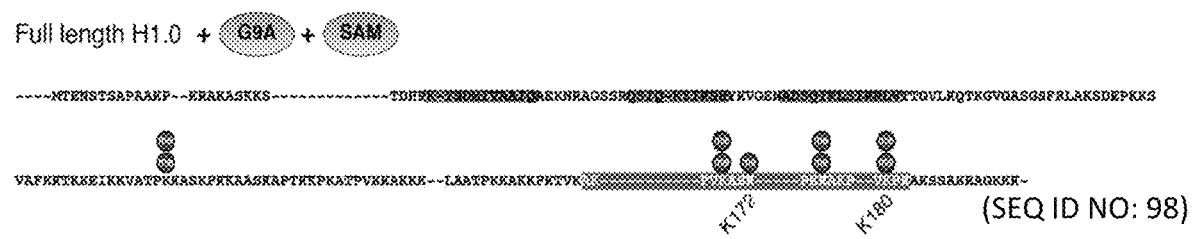
FIG. 11 shows that in the presence of recombinant, full-length H1.0, G9A methyltransferase methylates C-terminal lysine residues, including H1.0K180me2.

In order to identify the precise locations of G9A methylation on full-length H1.0 protein, a methylation reaction was set up and the products identified by LC-MS. The methylation reaction comprised recombinant G9A, an unlabeled methyl donor (S-Adenosyl-L-Methionine), and recombinant human H1.0 protein. The methylation reaction was subsequently analyzed by LC-MS, and sites of methylation were identified. The number of "me" circles in FIG. 11 represents the methylation state of the lysine residue (mono-, di-, or tri-methylated). FIG. 11 shows that in the presence of recombinant, full-length H1.0, G9A methylates C-terminal lysine residues, including H1.0K180me2.

Example 3: In Vitro Methylation with GLP and Analysis of Products

Figure 12:
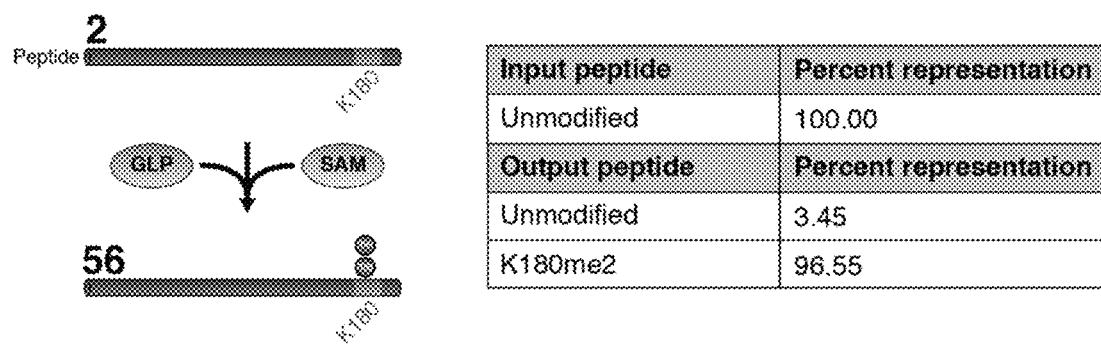
FIG. 12 shows that in the presence of unmethylated H1.0 peptide, GLP methyltransferase specifically dimethylates H1.0K180 (96.6% of all peptides) to produce H1.0K180me2.

In order to identify the precise locations of GLP methylation on unmodified H1.0 peptide (AKPVKASKPKKAK-PVKPK (SEQ ID NO:36)), a methylation reaction was set up and the products identified by LC-MS. The methylation reaction comprised recombinant GLP, an unlabeled methyl donor (S-Adenosyl-L-Methionine), and unmodified H1.0 peptide. The methylation reaction was subsequently analyzed by LC-MS, and each spectral peak (corresponding to a peptide species in the final reaction) was identified and quantified using spectral counts. The number of "me" circles in FIG. 12 represents the methylation state of the lysine residue (mono-, di-, or tri-methylated). FIG. 12 shows that in the presence of unmethylated H1.0 peptide, GLP specifically dimethylates H1.0K180 (96.6% of all peptides).

Figure 13:
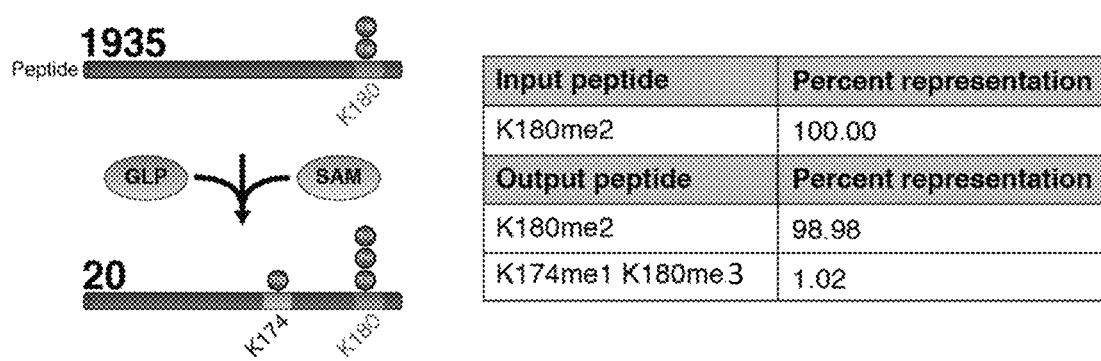
FIG. 13 shows that in the presence of a K180 dimethylated H1.0 peptide, GLP methyltransferase only further methylates H1.0K180 and H1.0K174, and only with a very low efficiency (1.02% of peptides are further methylated).

In order to identify the precise locations of GLP methylation on K180 dimethylated H1.0 peptide (AKPVKASKPK-KAKPVK$^{(me2)}$PK (SEQ ID NO:3)), a methylation reaction was set up and the products identified by LC-MS. The methylation reaction comprised recombinant GLP, an unlabeled methyl donor (S-Adenosyl-L-Methionine), and H1.0K180me2 peptide. The methylation reaction was subsequently analyzed by LC-MS, and each spectral peak (corresponding to a peptide species in the final reaction) was identified and quantified using spectral counts. The number of "me" circles in FIG. 13 represents the methylation state of the lysine residue (mono-, di-, or tri-methylated). FIG. 13 shows that in the presence of K180 dimethylated H1.0 peptide, GLP only further methylates H1.0K180 and H1.0K174, and only with a very low efficiency (1.02% of peptides are further methylated).

Figure 14:
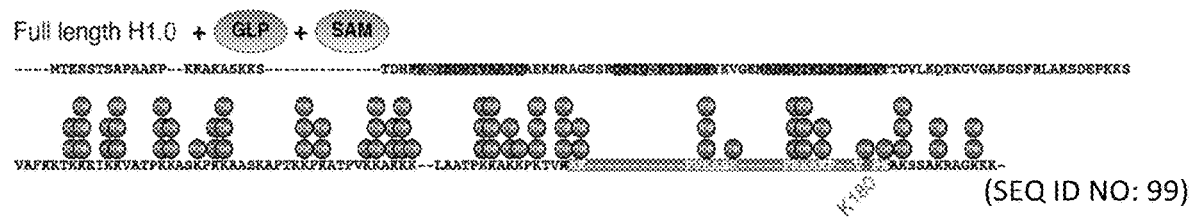
FIG. 14 shows the methylation of recombinant full-length H1.0 protein with GLP methyltransferase.

In order to identify the precise locations of GLP methylation on full-length H1.0 protein, a methylation reaction was set up and the products identified by LC-MS. The methylation reaction comprised recombinant GLP, an unlabeled methyl donor (S-Adenosyl-L-Methionine), and recombinant human H1.0 protein. The methylation reaction was subsequently analyzed by LC-MS, and sites of methylation were identified. The number of "me" circles in FIG. 14 represents the methylation state of the lysine residue (mono-, di-, or tri-methylated). FIG. 14 shows that in the presence of recombinant full-length H1.0, under the conditions described herein, GLP does not methylated full length H1.0. GLP methylates a large number of lysine residues on the C-terminal tail of H1.0, lacking the specificity of G9A, under the conditions provided herein.

Example 4: siRNA Knockdown of G9A in hADSCs

Figure 15A:
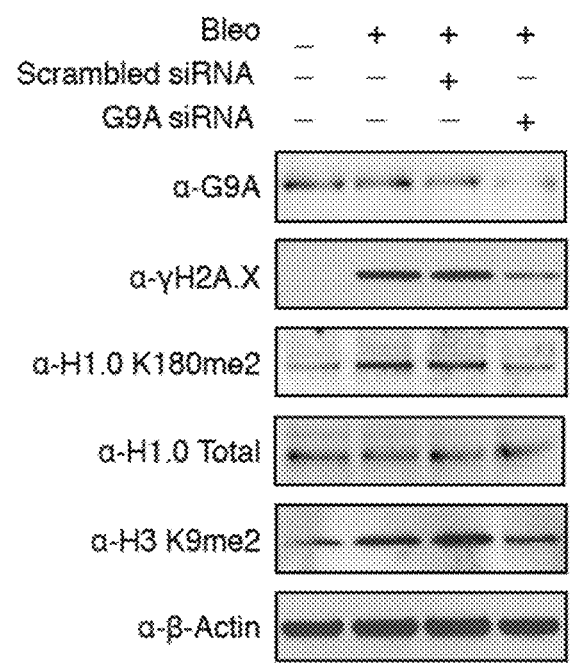

Self renewing (SR) human adipose derived stem cells (hADSCs) were transfected with either scrambled control siRNA or siRNA targeting G9A. The cells were then subjected to 2 hours bleomycin treatment. Western blot analysis indicated knockdown of G9A in vivo results in reduced H1.0K180me2 appearance upon DNA damage. H3K9me2, a known methylation product of G9A, was used to monitor loss of G9A activity upon knockdown. (FIG. 15A)

The siRNA knockdown of G9A in hADSCs led to a significant reduction in H1.0K180me2 levels upon 2 hours bleomycin treatment (ADD) concomitantly with a reduction of H3K9me2, a known PTM provided by G9A (FIG. 15B).

Example 5: Production of in Vitro Methylated H1.0K180me2 Proteins or Peptides in Bulk As observed in FIG. 8B and FIG. 11, G9A is capable of efficiently and specifically dimethylating K180 on full length recombinant human H1.0. This process may be utilized in order to create large quantities of H1.0K180me2 full length protein that could be incorporated into ELISA kits (e.g. sandwich ELISA kits) as a reference standard for the detection of H1.0K180me2 in biological samples. This process could involve setting up a bulk methylation reaction comprising 1×HMT reaction buffer (50 mM Tris-HCl, 5 mM $MgCl_2$, 4 mM dithiothreitol, pH 9.0), recombinant human or mouse G9A Methyltransferase, 3.2 mM S-Adenosyl-L-Methionine, and recombinant full-length human H1.0 labeled with an N-terminal tag (HA, His, GST, FLAG or other tag suitable for downstream purification). The reaction could be incubated at 37° C. for 1 hour to enable G9A-mediated H1.0K180me2 methylation.

Full-length H1.0 containing K180me2 would then be enriched and purified in a one or two-step process. First, all full-length recombinant H1.0 species in the reaction would be purified away from the reaction mixture through affinity purification utilizing the N-terminal tag. In one instance, H1.0 could be labeled with HA tag and purified with an HA antibody immobilized on a column or resin. After purification, the tag could be removed through proteolytic cleavage if required. This process would enrich for only full-length H1.0K180me2 in the final product, ensuring both capture and detection epitopes were present. The second step would utilize an H1.0K180me2 antibody immobilized on a column or resin, in order to further purify only full length H1.0 species containing H1.0K180me2. This final product could then be concentrated (for example using lyophilization), quantified, and included in ELISA kits as a reference standard, or used as a therapeutic. A one step purification approach utilizing only H1.0K180me2 antibody purification may be sufficient in some instances.

Example 6: H1.0K180me2 Antibody

A polyclonal antibody specific to an H1.0K180me2 antigen was made as follows: Two New Zealand rabbits were immunized for antibody production. Injections were administered subcutaneously (SQ) as emulsions of Keyhole Limpet Hemocyanin (KLH) conjugated to a H1.0K180me2 peptide (Peptide: CAKPVKASKPKKAKPVK(me2)PK (SEQ ID NO:89); Conjugated Peptide: (KLH-CAK-PVKASKPKKAKPVK(me2)PK (SEQ ID NO:90)) in Complete Freund's Adjuvant (CFA) or Incomplete Freund's Adjuvant (IFA). Initial immunization was performed with 0.5 mg of antigen in CFA at 10 SQ sites. 6 subsequent booster immunizations were performed at routine intervals over a 7-8 week period. Boosters consisted of 0.25 mg antigen in IFA at 4 SQ sites. Rabbits were bled at week 5 (~25 ml blood per rabbit) and at week 8 (~50 ml blood per rabbit). The titer of the immunization was assessed using ELISA by comparing pre- and post-immunization bleeds. The antibody was then purified using antigen affinity chromatography. The antigen used for purification was either biotin- or bovine serum albumin (BSA)-conjugated H1.0K180me2 peptide (biotin-CAKPVKASKPKKAKPVK (me2)PK (SEQ ID NO:91)) or BSA-CAKPVKASKPK-KAKPVK(me2)PK (SEQ ID NO:92)).The peptides were dimethylated using the in vitro methylation methods provided herein.

Figure 2A:
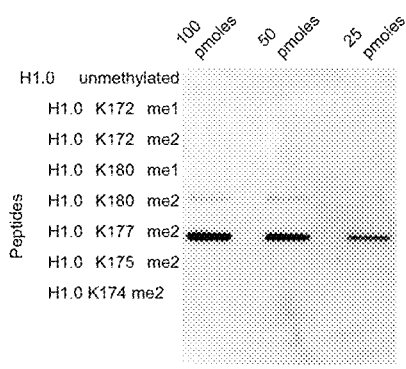
FIGS. 2A-2C show the specificity of an H1.0K180me2 antibody.
Figure 2B:
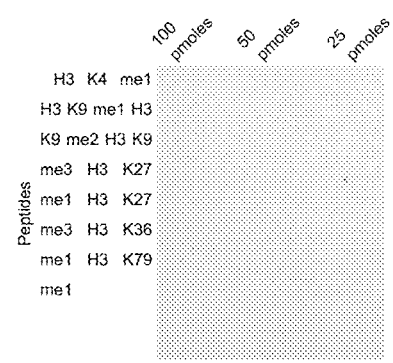

The H1.0K180me2 antibody was tested as follows. To check the specificity of H1.0K180me2 antibody, histone H1.0 peptides methylated on K172, K174, K175, K177, or K180 were transferred to a membrane using a vacuum-manifold slot blot in a dilution series. The membrane was then immunoblotted using the H1.0K180me2 antibody to identify potential cross-reactivity with other methyl-lysine groups. The H1.0K180me2 antibody is highly specific for H1.0K180me2, even in low concentrations (FIG. 2A). To further check the specificity of the H1.0K180me2 antibody, histone H3 peptides methylated on K4, K9, K27, K36 or K79 were transferred to a membrane using a vacuum-manifold slot blot in a dilution series. The membrane was then immunoblotted using the H1.0K180me2 antibody to identify potential cross-reactivity with other methyl-lysine groups. This antibody exhibited no cross-reactivity with any methylated H3 peptides analyzed (FIG. 2B). The slot blot analysis protocol was carried out according to methods described in Example 1.

Figure 2C:
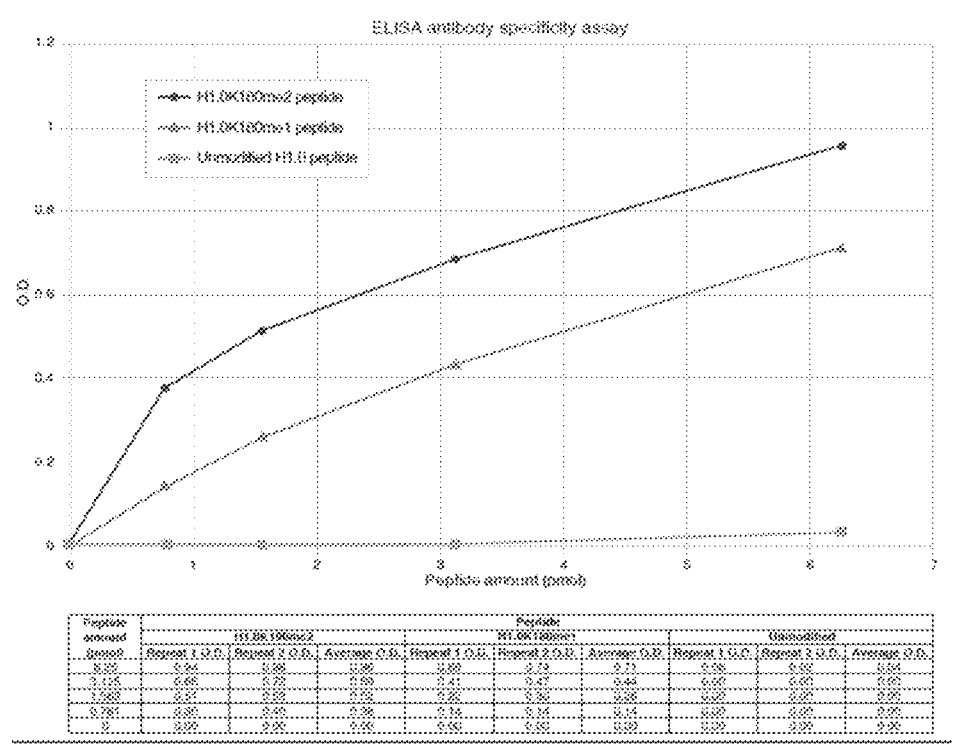

The specificity of the rabbit anti-H1.0K180me2 IgG antibody was determined using the anti-H1.0K180me2 IgG ELISA test. Wells were coated with either H1.0K180me2 peptide, H1.0K180me1 peptide, or unmodified peptide, in a 2×dilution series from 6.25 pmol to 781 fmol. 6.67 fmol of rabbit anti-H1.0K180me2 IgG antibody in 100 ul buffer were added to each well and antibody binding efficiency was monitored by ELISA. Curves for each peptide were generated by plotting peptide amount against measured O.D at 450 nm. Raw ELISA data is given in the table the figure for the two experimental repeats. (FIG. 2C)

The rabbit anti-H1.0K180me2 IgG antibody is 2.7× more efficient at binding H1.0K180me2 peptide than H1.0K180me1 peptide. Within the optimal linear range, 1 molecule of rabbit anti-H1.0K180me2 IgG antibody recognizes 1 out of 117 molecules of H1.0K180me2 peptide, but only 1 out of 316 molecules of H1.0K180me1 peptide. Unmodified peptide is not recognized in this range.

Example 7: Use of the H1.0K180me2 Antibody Shows that H1.0K180me2 is Associated with Acute DNA Damage To assess the relationship between H1.0K180 methylation and DNA damage, SR hADSCs and hADSCs treated with DNA damaging agent bleomycin for 2 hours (according to methods described in Example 1) were lysed and fractionated to obtain the chromatin bound fraction. Western blot analysis with an anti-H1.0K180me2 antibody (performed according to methods described in Example 1) shows methylation of H1.0K180 on the chromatin upon DNA damage (FIG. 3). Upon treatment of SR hADSCs with bleomycin to induce DNA double-strand breaks (according to methods described in Example 1), H1.0K180me2 localized to the cytoplasm.

Example 8: Use of the H1.0K180me2 Antibody Shows that H1.0K180me2 is Released From Chromatin Upon Genotoxic Stress-Induced Senescence and is Secreted Into the Extracellular Matrix SR hADSCs, hADSCs treated with bleomycin for 2 hours (acute DNA damage) and hADSCs treated with bleomycin and allowed to senesce for 3 days (genotoxic stress induced senescence) were lysed and fractionated into soluble and chromatin bound fractions. These fractions were then subjected to LC-MS/MS analysis. Peptide expression levels were taken as the total area under the LC-MS/MS relative intensity curve, and individual peptides were unambiguously assigned to proteins using Pinpoint software, version 1.4 (Thermo Scientific). The areas of all peptides assigned to an individual protein were summed to yield protein expression levels, which were normalized against the total protein library size for each sample. For each cellular fraction, H1.0 peptide abundance is represented as a percentage of total H1.0 peptides observed in each condition. Normalized absolute values of H1.0 peptide levels in each fraction were also shown. As shown in FIG. 4A, Chromatin bound H1.0 decreased from ~60% of total in SR and acute DNA damage, to ~30% of total upon genotoxic stress induced senescence. Culture media from SR hADSCs treated with bleomycin was collected for slot blot analysis with α-H1.0 and α-H1.0K180me2 antibodies to assess secretion of H1.0 to the extracellular matrix (ECM). The experiment was carried out according to methods described in Example 1. Secreted H1.0 was detectable in the cell culture media, and after 24 hours of bleomycin treatment, secreted H1.0K180me2 was also readily detected (FIG. 4B). These results confirmed that methylated H1.0K180 is released from chromatin upon genotoxic stress induced senescence and is secreted into the ECM. By slot blot immunoassay, it was found that the presence of H1.0K180me2 was detected in the conditioned medium of hADSCs in a time course dependent manner after genotoxic insult imposed by bleomycin, with maximal H1.0K180me2 secretion detected within 48 hours (FIG. 4C). This signifies secretion out of the cells. An increase in DFFB secretion upon GSI-SEN was seen, in a similar manner to H1.0K180me2 starting 48 hours after treatment (FIG. 4C).

Example 9: Use of the H1.0K180me2 Antibody Shows that Exposure to Ionizing Radiation Induces Increased Levels of H1.0k180me2 in Serum The effect of ionizing radiation on H1.0K180me2 levels in serum was examined. Serum was collected from wild-type mice before and either 2 hours or 48 hours after exposure to 7 Gy of ionizing radiation, according to methods described in Example 1. H1.0K180me2 serum levels 2 hours (mouse 1) or 48 hours (mouse 2) after irradiation were compared to initial levels before treatment using slot blot and immunoblotting with α-H1.0K180me2 antibody (FIG. 5A). The concentration of H1.0K180me2 in each serum sample was calculated using a standard curve of H1.0K180me2 peptide included in each analysis. Mouse serum albumin was used as a loading control. H1.0K180me2 dot blot bands were quantified and normalized by serum albumin. Relative increases in H1.0K180me2 after irradiation are shown (FIG. 5B). Western blot analysis of equal volumes of mouse serum with α-H1.0K180me2 antibody also showed increased H1.0K180me2 after irradiation (FIG. 5C).

Example 10: Use of the H1.0K180me2 Antibody to Show that Repamycin and its Derivatives Block the Accumulation of H1.0K180me2 in the Cytoplasm, Following DNA Damage To test if rapamycin derivatives can block H1.0K180me2 appearance upon DNA damage, SR hADSCs were treated with bleomycin for 2 hours with or without pretreatment with rapamycin or everolimus (a derivative of rapamycin) for 24 hours. Cells were then lysed and analyzed be western blot for H1.0K180me2, γH2A.X and β-Actin, according to methods described in Example 1. As shown in FIG. 7, both rapamycin and everolimus reduced the appearance of H1.0K180me2 upon bleomycin treatment, suggesting everolimus can also block H1.0K180me2 appearance upon DNA damage.

Example 11: Use of the H1.0K180me2 Antibody Shows that the H1.0K180me2 Level in Brain Tissue and Serum is an Indication of Alzheimer's Disease Human sera were obtained from the Cooperative Human Tissue Network (CHTN) and Nuclea Biotechnologies (NCB). Sera were derived from three groups: 1) middle-aged healthy donors with no significant medical condition (n=7, age range=32-38 years old) 2) old healthy donors with no significant medical condition (n=9, age range=63-76 years old) 3) old donors with clinically diagnosed Alzheimer's disease (n=10, age range=75-103 years old). Further details of each donor in Table 6.

TABLE 6

Characteristics of Tissue Donors

| Sample Type | Age | Gender | Race | Patient Diagnosis |
|---|---|---|---|---|
| Brain | 23 | Female | White | Normal |
| Brain | 60 | Female | White | Normal |
| Brain | 73 | Female | White | Normal |
| Brain | 77 | Female | White | Normal |
| Serum | 32 | Female | White | Normal |
| Serum | 32 | Female | Black | Normal |
| Serum | 32 | Male | Black | Normal |
| Serum | 36 | Female | White | Normal |
| Serum | 36 | Male | White | Normal |
| Serum | 37 | Male | Black | Normal |
| Serum | 38 | Male | White | Normal |
| Serum | 63 | Female | White | Normal |
| Serum | 66 | Female | White | Normal |
| Serum | 67 | Female | White | Normal |
| Serum | 70 | Female | White | Normal |
| Serum | 70 | Female | White | Normal |
| Serum | 70 | Female | White | Normal |
| Serum | 73 | Female | Black | Normal |
| Serum | 74 | Female | White | Normal |
| Serum | 76 | Female | White | Normal |
| Serum | 83 | Male | Black | Alzheimer's disease |
| Serum | 103 | Male | White | Alzheimer's disease |
| Serum | 94 | Female | White | Alzheimer's disease |
| Serum | 77 | Male | Black | Alzheimer's disease |
| Serum | 78 | Female | Black | Alzheimer's disease |
| Serum | 78 | Male | White | Alzheimer's disease |
| Serum | 75 | Female | White | Alzheimer's disease |
| Serum | 91 | Female | Black | Alzheimer's disease |
| Serum | 93 | Female | Black | Alzheimer's disease |
| Serum | 90 | Female | Black | Alzheimer's disease |

Whole cell lysates of human brain samples from 23 years (young) and or greater than 60 years (old) healthy individuals were also analyzed by western blot with antibodies and methods described above. Table 6 provides characteristics of brain tissue donors.

Figure 6A:
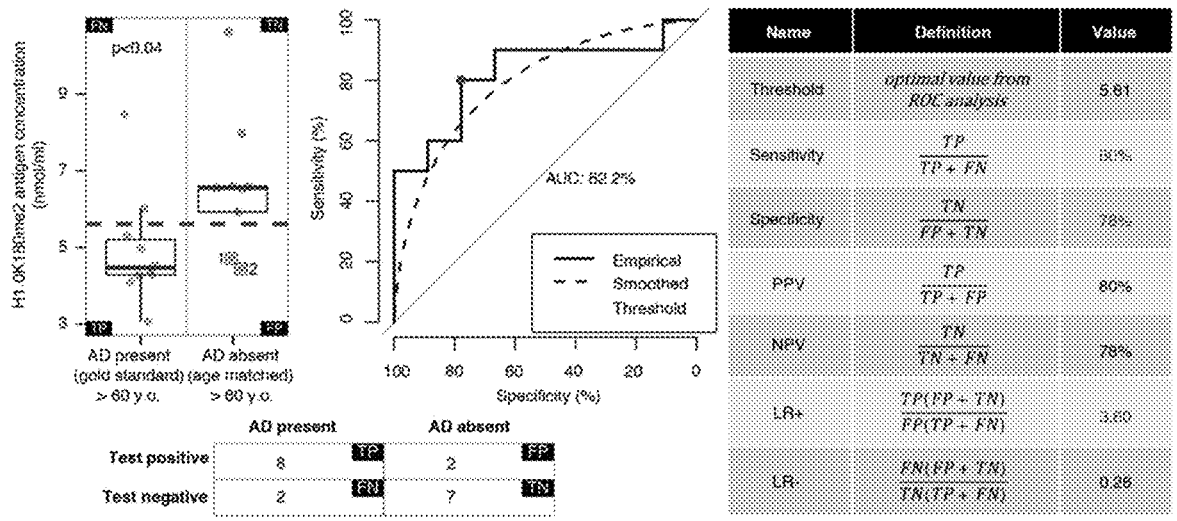
FIG. 6A shows that measuring H1.0K180me2 using an H1.0K180me2 antibody can be used as a biomarker of Alzheimer's disease.
Figure 6C:
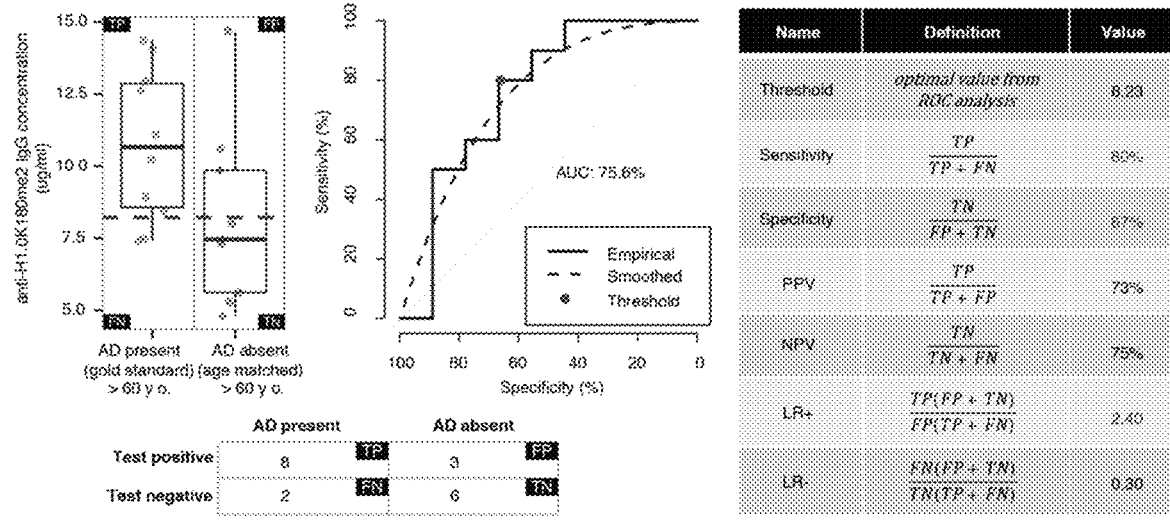
FIG. 6C shows that the measurement of serum antibodies (autoantibodies) using an H1.0K180me2 peptide can be used as a biomarker of Alzheimer's disease.
Figure 7:
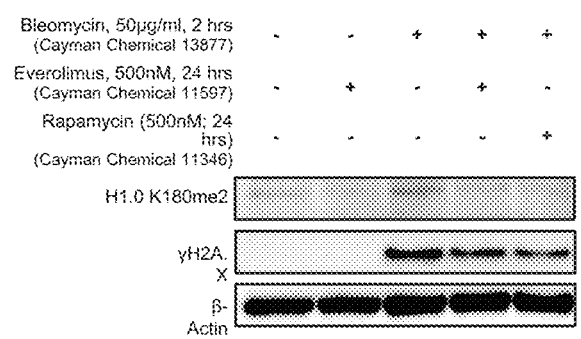
FIG. 7 shows a western blot analysis of H1.0K180me2 (using an H1.0K180me2 antibody) in human adipose derived stem cells after bleomycin treatment (a DNA damaging agent), revealing that everolimus, a derivative of rapamycin (an approved mTOR Kinase Inhibitor), blocks H1.0K180me2 deposition on chromatin.

FIG. 6A shows the quantification of H1.0K180me2 levels determined by slot blot analysis in Alzheimer's disease patients and age-matched controls, using the H1.0K180me2 antibody. Quantification of H1.0K180me2 levels was determined by slot blot analysis in Alzheimer's disease patients and age-matched controls. The concentration of H1.0K180me2 in each serum sample was calculated using a standard curve of H1.0K180me2 peptide included in each analysis. As shown in FIG. 6A, Alzheimer's disease patients displayed lower concentrations of serum H1.0K180me2 than healthy age-matched controls, indicating that H1.0K180me2 serum concentrations can effectively segregate patients with Alzheimer's disease from healthy individuals and could act as a diagnostic tool for Alzheimer's disease detection. As shown in Table 7, measurement of H1.0K180me2 antigen concentration in serum at or below 5.61 nmol/ml is indicative of the disease presence with likelihood of 24%, compared to pre-test probability; and the positive likelihood ratio (PLR) is 3.6. Post-test probability is calculated based on following formula: Pre-test Odds X LR/(1+Pre-test Odds×LR), where pre-test odds are the clinical suspicion of disease present before testing. This is usually calculated from the Likelihood Ratio Nomogram or Fagan Nomogram (NEJM 1975; 293: 257).

TABLE 7

H1.0K180me2 antigen concentration normalized by serum volume

| Metric | Value | 95% confidence interval |
|---|---|---|
| Threshold | 5.61 | |
| Sensitivity | 80% | [56%, 100%] |
| Specificity | 78% | [40%, 100%] |
| PPV | 80% | [69%, 100%] |
| NPV | 78% | [60%, 100%] |
| LR+ | 3.60 | [2.03, 17.27] |
| LR− | 0.26 | [0.00, 0.60] |
| ln(OR) | 2.64 | [0.43, 4.85] |

Example 12: Use of Labeled H1.0K180me2 Peptides to Measure H1.0K180me2 IgG Levels in Human Fluids FIG. 6B shows that human anti-H1.0K180me2 IgG can be detected in different human biofluids using the indirect ELISA method (using H1.0K180me2 peptides of the invention). Human plasma, urine, and saliva were each tested for anti-H1.0K180me2 IgG using the indirect ELISA test. A linear relationship between plasma concentration and O.D. measured at 450 nm was detected when plasma was diluted 500×, 1000×, and 2000× in loading buffer. Similarly, a linear relationship between urine and saliva concentration and O.D. measured at 450 nm was detected when these fluids were diluted 80× and 160× in loading buffer. This suggests that the anti-H1.0K180me2 IgG indirect ELISA test has a utility to detect anti-H1.0K180me2 IgG in a wide variety of human biofluids.

In a related experiment anti-H1.0K180me2 IgG levels in human serum were quantified by indirect ELISA analysis using biotinylated-H1.0K180me2 peptide, as methylated using the in vitro methods provided herein, followed by a secondary antibody specific for IgG antibodies. Equal volumes of serum from healthy individuals of 30-40 years (n=7) or >60 years (n=9), and individuals with clinically diagnosed Alzheimer's disease of >60 years (n=10) were analyzed. (FIG. 6C)

FIG. 6C shows the quantification of autoanti-H1.0K180me2 IgG levels determined by indirect ELISA in Alzheimer's disease patients and age-matched controls. The concentration of anti-H1.0K180me2 IgG in each serum sample was calculated using a standard curve created with serial dilutions of the H1.0K180me2 specific antibody described above. Alzheimer's disease patients display higher concentrations of serum anti-H1.0K180me2 IgG than healthy age-matched controls. Anti-H1.0K180me2 IgG serum concentrations can effectively segregate patients with Alzheimer's disease from healthy individuals and can act as a diagnostic tool for Alzheimer's disease detection. As shown in Table 8, measurement of auto antiH1.0K180me2 antibodies in concentration equal to, or higher than, 9.69 ug/ml is indicative of the disease presence with likelihood of 30%, compared to pre-test probability, with a PLR of 5.4. FIG. 6C shows standard curve the quantification of H1.0K180me2 autoantibodies in human serum. Total serum protein was measured for each sample using the Bradford assay. Anti-H1.0K180me2 IgG concentrations were normalized by measured protein concentration in each sample. Anti-H1.0K180me2 IgG levels are decreased in healthy >60 year individuals relative to healthy younger individuals (30-40 years). Patients with Alzheimer's disease exhibit increased normalized levels of anti-H1.0K180me2 IgG relative to healthy aged individuals (>60 years).

TABLE 8

Anti-H1.0K180me2 IgG concentration normalized by serum volume

| Metric | Value | 95% confidence interval |
|---|---|---|
| Threshold | 8.23 | |
| Sensitivity | 80% | [33%, 100%] |
| Specificity | 67% | [50%, 100%] |
| PPV | 73% | [63%, 100%] |
| NPV | 75% | [62%, 100%] |
| LR+ | 2.40 | [1.50, 15.45] |

The anti-H1.0K180me2 IgM concentration was calculated for each replicate from the standard curve shown in FIG. 6G. The average anti-H1.0K180me2 IgM concentration for each sample was calculated from the three technical replicates. The sample standard deviation between the three technical replicates was also calculated. The coefficient of embodiment between the replicates was calculated as CV%=standard deviation/average×100%.

As an anti-H1.0K180me2 standard curve was not available, the standard curve was created using an anti-H1.0K180me2 IgG antibody (FIG. 6G). The molar concentration of anti-H1.0K180me2 IgG was plotted against OD at 450 nm. The curve was then used to infer the molar concentration of anti-H1.0K180me2 IgM in each sample.

TABLE 9

Raw data from anti-H1.0K180me2 IgM ELISA

| | | | Repeat 1 | | Repeat 2 | | Repeat 3 | | | | |
|---|---|---|---|---|---|---|---|---|---|---|---|
| Patient Group | Patient ID | Patient Age | O.D. | Anti-H1.0 K180me2 IgM (fmol/ml) | O.D. | Anti-H1.0 K180me2 IgM (fmol/ml) | O.D. | Anti-H1.0 K180me2 IgM (fmol/ml) | Average Anti-H1.0 K180me2 IgM (fmol/ml) | Standard deviation | % CV |
| AD | NC17 | 75 | 0.18 | 498.9 | 0.18 | 510.1 | 0.16 | 431.5 | 480.1 | 42.5 | 8.9 |
| AD | NC14 | 77 | 0.46 | 1288.2 | 0.47 | 1321.9 | 0.47 | 1319.1 | 1309.7 | 18.7 | 1.4 |
| AD | NC15 | 78 | 0.23 | 653.4 | 0.20 | 566.3 | 0.18 | 498.9 | 572.8 | 77.5 | 13.5 |
| AD | NC11 | 83 | 0.13 | 358.4 | 0.10 | 285.4 | 0.11 | 313.5 | 319.1 | 36.8 | 11.5 |
| AD | NC20 | 90 | 0.38 | 1063.5 | 0.37 | 1021.3 | 0.38 | 1049.4 | 1044.8 | 21.5 | 2.1 |
| AD | NC18 | 91 | 0.49 | 1369.7 | 0.48 | 1350.0 | 0.36 | 1010.1 | 1243.3 | 202.1 | 16.3 |
| AD | NC19 | 93 | 0.16 | 434.3 | 0.15 | 428.7 | 0.16 | 456.7 | 439.9 | 14.9 | 3.4 |
| AD | NC13 | 94 | 0.19 | 518.5 | 0.18 | 512.9 | 0.19 | 515.7 | 515.7 | 2.8 | 0.5 |
| AD | NC12 | 103 | 0.06 | 156.2 | 0.05 | 147.8 | 0.06 | 173.0 | 159.0 | 12.9 | 8.1 |
| Control | WD-32339 | 63 | 0.06 | 175.8 | 0.05 | 139.3 | 0.06 | 153.4 | 156.2 | 18.4 | 11.8 |
| Control | WD-32347 | 66 | 0.06 | 164.6 | 0.05 | 142.1 | 0.05 | 147.8 | 151.5 | 11.7 | 7.7 |
| Control | WD-32398 | 70 | 0.20 | 557.9 | 0.20 | 569.1 | 0.20 | 566.3 | 564.4 | 5.8 | 1.0 |
| Control | WD-36002 | 70 | 0.13 | 347.2 | 0.12 | 344.4 | 0.16 | 456.7 | 382.8 | 64.1 | 16.7 |
| Control | WD-32351 | 70 | 0.12 | 344.4 | 0.11 | 313.5 | 0.12 | 330.3 | 329.4 | 15.5 | 4.7 |
| Control | WD-36008 | 73 | 0.07 | 184.3 | 0.07 | 192.7 | 0.08 | 215.2 | 197.4 | 16.0 | 8.1 |
| Control | WD-36010 | 74 | 0.06 | 161.8 | 0.07 | 184.3 | 0.05 | 142.1 | 162.7 | 21.1 | 13.0 |
| Control | WD-32346 | 76 | 0.15 | 420.2 | 0.14 | 389.3 | 0.15 | 417.4 | 409.0 | 17.1 | 4.2 |
| Control | WD-32350 | 66 | 0.15 | 417.4 | 0.16 | 451.1 | 0.20 | 543.8 | 470.8 | 65.5 | 13.9 |

TABLE 8-continued

Anti-H1.0K180me2 IgG concentration normalized by serum volume

| Metric | Value | 95% confidence interval |
|---|---|---|
| LR− | 0.30 | [0.00, 0.56] |
| ln(OR) | 2.08 | [0.00, 4.16] |

Example 13: Use of Labeled H1.0K180me2 Peptides to Measure H1.0K180me2 IgM Levels in Human Fluids In another related experiment, anti-H1.0K180me2 IgM levels in human serum were quantified by indirect ELISA analysis using biotinylated-H1.0K180me2 capture peptide (an H1.0K180me2 autoantibody-binding peptide), followed by a secondary antibody specific for IgM antibodies. Equal volumes of serum from healthy individuals >60 years (n=9), and individuals with clinically diagnosed Alzheimer's disease of >60 years (n=10) were analyzed. (raw data in FIG. 6H; data normalized to total IgM levels in FIG. 6I).

Table 9 below shows the raw data from the indirect ELISA analysis, and further analyzed in FIGS. 6G-6H. The ELISA was performed in triplicate for each patient sample.

FIG. 6H demonstrates the utility of measurements of IgG autoantibodies to H1.0K180me2 as biomarkers of Alzheimer's disease (figures show raw data). The left panel shows the ROC curve analysis, used to evaluate the overall predictive performance, and to pick an optimal threshold cutoff value, to distinguish between positive and negative test results. The relationship between percent specificity and sensitivity at each possible threshold are plotted as shown to create the empirical ROC curve (solid line). The empirical ROC curve was used to calculate the optimal threshold cutoff value pictured in the right panel. The optimal threshold value is shown as a gray dot on the empirical ROC curve. The right panel of FIG. 6H shows a box plot distribution of anti-H1.0K180me2 IgM concentrations in patients with Alzheimer's disease and those without (neurologic controls). Individual measurement values for all samples are shown as dots, and box-plots are shown for each distribution along with the upper quartile, lower quartile, and distance of the upper and lower quartile to the largest and lowest non-outlying points. Samples above the threshold cutoff (dashed line) are considered positive for the test. Samples below the threshold cutoff are considered negative for the test. The 2×2 matrix at the bottom of FIG. 6H shows the distribution can be divided into four groups: true positives (TP; where the index was positive, and AD was present); false positives (FP; where the index was positive, but AD was not present); true negatives (TN; where the index was negative, and AD was not present); and false negatives (FN; where the index was negative, but AD was present). The numbers of samples that fall within each group were plotted on the 2×2 matrix.

Table 10 below shows the assessment of anti-H1.0K180me2 IgM test performance, for the raw data.

TABLE 10

Assessment of anti-H1.0K180me2 test performance

| Metric | Value | 95% confidence interval |
|---|---|---|
| Threshold | 409 | |
| Sensitivity | 78% | [45%, 94%] |
| Specificity | 78% | [45%, 94%] |
| PPV | 78% | [45%, 94%] |
| NPV | 78% | [45%, 94%] |
| LR+ | 3.50 | [0.98, 12.47] |
| LR− | 0.29 | [0.08, 1.02] |
| ln(OR) | 2.51 | [0.28, 4.73] |

Figure 6J:
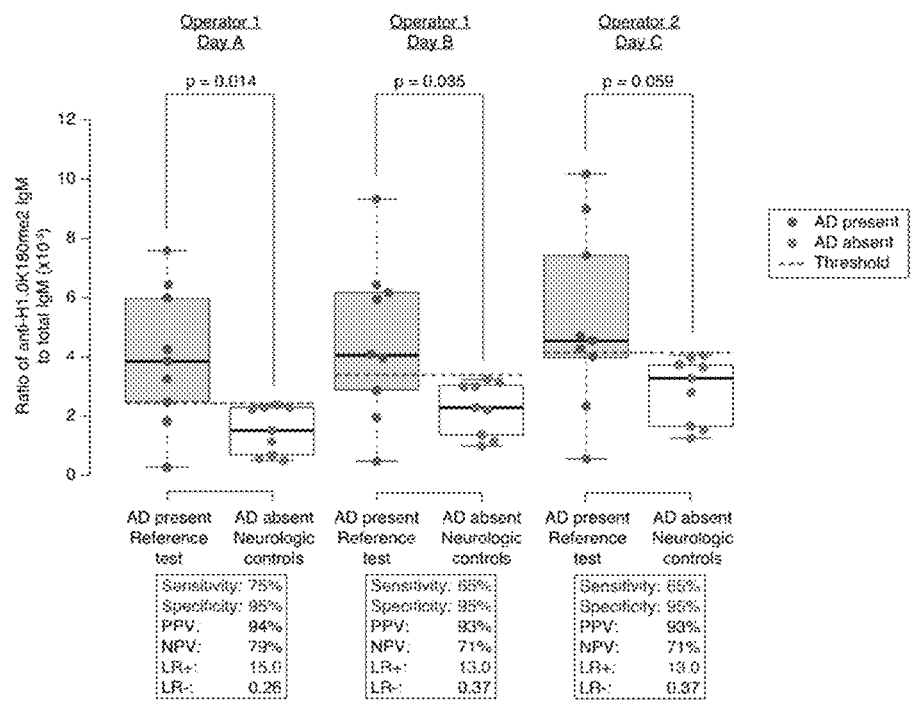
FIG. 6J demonstrates the stability and reproducibility of diagnostic characteristics of serological indirect ELISA for the measurements and quantification of antiH1.0K180me2 IgM between different operators and different laboratory settings.

Table 11 below shows the normalized data (anti-H1.0K180me2 IgM normalized by total IgM levels) from the indirect ELISA analysis, and further analyzed in FIG. 6I, FIG. 6J. The ELISA was performed in triplicate for each patient sample. The anti-H1.0K180me2 IgM concentration was calculated for each replicate from the standard curve shown in FIG. 6G, and normalized by the average total IgM concentration measured in the sample (FIG. 6E). The average, normalized anti-H1.0K180me2 IgM concentration for each sample was calculated from the three technical replicates. The sample standard deviation between the three technical replicates was also calculated. The coefficient of embodiment between the replicates was calculated as CV %=standard deviation/average×100%.

FIG. 6I demonstrates the utility of measurements of IgM autoantibodies to H1.0K180me2 as biomarkers of Alzheimer's disease (figures show normalized data). The left panel shows the ROC curve analysis, used to evaluate the overall predictive performance, and to pick an optimal threshold cutoff value, to distinguish between positive and negative test results. The relationship between percent specificity and sensitivity at each possible threshold are plotted as shown to create the empirical ROC curve (solid line). The empirical ROC curve was used to calculate the optimal threshold cutoff value pictured in the right panel. The optimal threshold value is shown as a gray dot on the empirical ROC curve. The right panel of FIG. 6I shows a box plot distribution of normalized anti-H1.0K180me2 IgM concentrations in patients with Alzheimer's disease and those without (neurologic controls). Individual measurement values for all samples are shown as dots, and box-plots are shown for each distribution. The box plots show median values along with the upper quartile, lower quartile, and distance of the upper and lower quartile to the largest and lowest non-outlying points. Samples above the threshold cutoff (dashed line) are considered positive for the test. Samples below the threshold cutoff are considered negative for the test. The 2×2 matrix at the bottom of FIG. 6I shows the distribution can be divided into four groups: true positives (TP; where the index was positive, and AD was present); false positives (FP; where the index was positive, but AD was not present); true negatives (TN; where the index was negative, and AD was not present); and false negatives (FN; where the index was negative, but AD was present). The numbers of samples that fall within each group were plotted on the 2×2 matrix. FIG. 15 B demonstrates that test characteristics do not fluctuate depending on laboratory setting and different operators.

Table 12 below shows the assessment of anti-H1.0K180me2 IgM test performance, for the normalized data.

TABLE 11

Normalized data from anti-H1.0K180me2 IgM ELISA

| Patient Group | Patient ID | Age | Ratio of anti-H1.0K180me2 IgM to total IgM ($\times 10^{-6}$) | | | | Standard deviation | % CV |
|---|---|---|---|---|---|---|---|---|
| | | | Repeat 1 | Repeat 2 | Repeat 3 | Average | | |
| AD | NC17 | 75 | 87.0 | 89.0 | 75.3 | 83.7 | 7.4 | 8.9 |
| AD | NC14 | 77 | 80.2 | 82.3 | 82.1 | 81.5 | 1.2 | 1.4 |
| AD | NC15 | 78 | 53.6 | 46.4 | 40.9 | 47.0 | 6.3 | 13.5 |
| AD | NC11 | 83 | 23.3 | 18.5 | 20.4 | 20.7 | 2.4 | 11.5 |
| AD | NC20 | 90 | 32.5 | 31.2 | 32.1 | 31.9 | 0.7 | 2.1 |
| AD | NC18 | 91 | 41.3 | 40.7 | 30.4 | 37.5 | 6.1 | 16.3 |
| AD | NC19 | 93 | 27.4 | 27.0 | 28.8 | 27.7 | 0.9 | 3.4 |
| AD | NC13 | 94 | 74.3 | 73.5 | 73.9 | 73.9 | 0.4 | 0.5 |
| AD | NC12 | 103 | 4.3 | 4.0 | 4.7 | 4.3 | 0.4 | 8.1 |
| Control | WD-32339 | 63 | 18.6 | 14.7 | 16.2 | 16.5 | 1.9 | 11.8 |
| Control | WD-32347 | 66 | 9.6 | 8.3 | 8.6 | 8.8 | 0.7 | 7.7 |
| Control | WD-32350 | 66 | 22.2 | 23.9 | 28.9 | 25.0 | 3.5 | 13.9 |
| Control | WD-32398 | 70 | 23.9 | 24.4 | 24.3 | 24.2 | 0.3 | 1.0 |
| Control | WD-36002 | 70 | 22.9 | 22.7 | 30.1 | 25.3 | 4.2 | 16.7 |
| Control | WD-32351 | 70 | 18.8 | 17.1 | 18.0 | 18.0 | 0.8 | 4.7 |
| Control | WD-36008 | 73 | 6.3 | 6.6 | 7.3 | 6.7 | 0.5 | 8.1 |
| Control | WD-36010 | 74 | 10.0 | 11.4 | 8.8 | 10.1 | 1.3 | 13.0 |
| Control | WD-32346 | 76 | 27.3 | 25.3 | 27.1 | 26.6 | 1.1 | 4.2 |

TABLE 12 anti-H1.0K180me2 IgM/total IgM test performance.

| Metric | Value | 95% confidence interval |
|---|---|---|
| Threshold | 26.6 | |
| Sensitivity | 75% | [44%, 92%] |
| Specificity | 95% | [66%, 99%] |
| PPV | 94% | [53%, 100%] |
| NPV | 79% | [47%, 95%] |
| LR+ | 15.00 | [0.98, 228.9] |
| LR− | 0.26 | [0.09, 0.78] |
| ln(OR) | 4.04 | [0.86, 7.23] |

The results of this test modify the probability of disease from 10% pre-test to 63% post-test. The positive likelihood ratio (LR+) is 15.0 (95% CI: 0.98, 229), and the positive predictive value (PPV) is 94% (95% CI: 53, 100). The negative likelihood ratio (LR−) is 0.26 (95% CI: 0.09, 0.78), and negative predictive value is 79% (95% CI: 47, 95).

Controls

FIG. 6E shows a standard curve: the molar concentration of a human IgG dilution series was plotted against OD at 450 nm. The curve was then used to extrapolate the molar concertation of total IgM in each sample.

Table 13 below shows the data from a total IgM ELISA. The ELISA was performed in triplicate for each patient sample. The total IgM molar concentration was calculated for each replicate from the standard curve shown in FIG. 6E. The average total IgM molar concentration for each sample was calculated from the three technical replicates. The sample standard deviation between the three technical replicates was also calculated. The coefficient of embodiment between the replicates was calculated as CV %=standard deviation/average×100%.

Figure 6K:
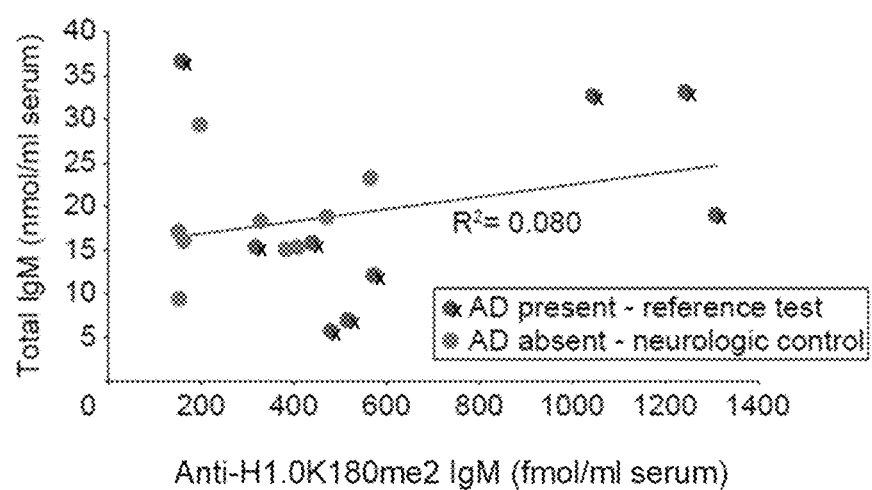
FIG. 6K demonstrates that correlation between total IgM and antiH1.0K180me2 IgM is not significant in both Alzheimer's disease and neurological controls patients (based on the $R^2$ value).

FIG. 6K demonstrates that there is no correlation between total IgM levels and anti-H1.0K180me2 IgM levels in patient samples. All patient samples were distributed on a scatter plot based on their measured anti-H1.0K180me2 IgM concentrations versus their measured total IgM concentration. Anti-H1.0K180me2 IgM levels are not influenced by total IgM levels in patient serum, as evidenced by the low $R^2$ value.

Figure 6L:
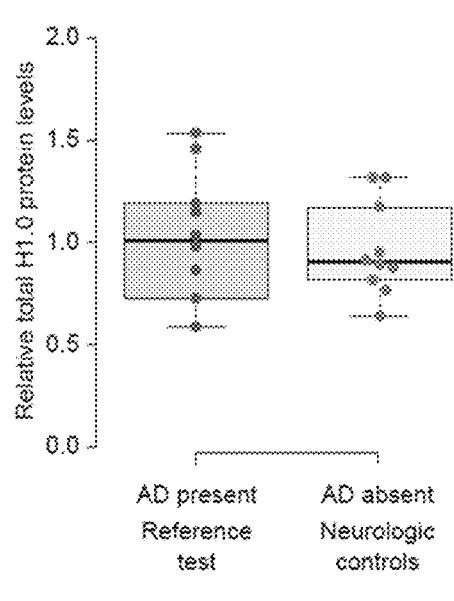
FIG. 6L demonstrates that total unmodified H1.0 protein levels (left graph) and total anti-H1.0 IgM levels (right graph) do not discriminate between individuals with and without Alzheimer's disease.
Figure 6L:
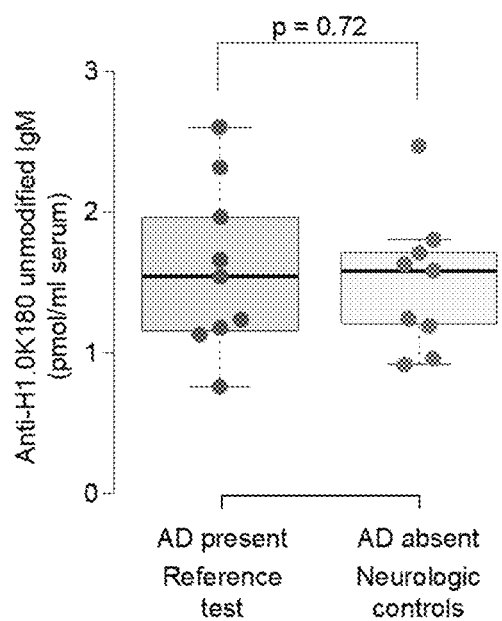

FIG. 6L demonstrates that total unmodified H1.0 protein levels (left graph) and total anti-H1.0 IgM levels do not discriminate between individuals with and without Alzheimer's disease. In the left panel, a custom chemiluminescent slot-blot immunoassay was used to measure total H1.0 (unmodified) levels in Alzheimer's disease and control patient serum samples. In the right panel, an indirect ELISA was used to measure IgM autoantibodies against H1.0 unmodified peptide in patient serum. There was no statistically significant difference in the levels of IgM autoantibodies against unmodified H1.0 peptide (p=0.72), indicating diagnostic utility for Alzheimer's is unique to anti-H1.0K180me2 IgM in patient serum. Relative measurement values for both panels, for all samples, are shown as dots, and box-plots are shown for each distribution. The box-plots show the median values along with the upper quartile, lower quartile, and distance of the upper and lower quartile to the largest and lowest non-outlying points.

Correlation of Anti-H1.0K180me2 IgG and IgM Levels

Figure 6M:
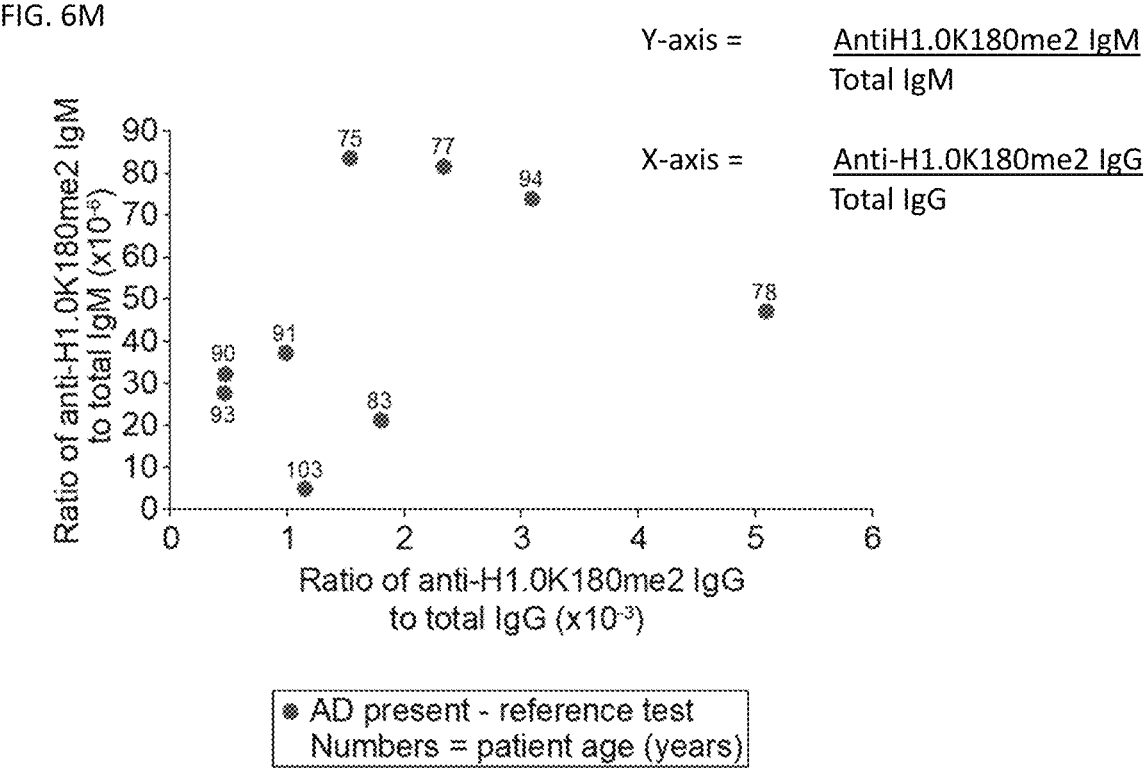
FIG. 6M demonstrates that measuring H1.0K180me2 IgG and H1.0K180me2 IgM autoantibodies, using H1.0K180me2 peptides, and correlating the two measurements, can stratify patients with Alzheimer's disease into distinct sub-populations.

FIG. 6M demonstrates that measuring H1.0K180me2 IgG and IgM autoantibodies can stratify patients with Alzheimer's disease into distinct populations. Anti-H1.0K180me2 IgG levels were measured in Alzheimer's disease patient samples, and these were normalized by total IgG levels. Normalized anti-H1.0K180me2 IgM levels in Alzheimer's disease patient samples were then correlated with these

TABLE 13

Measurement of total IgM levels in patient serum using an ELISA assay

| Patient Group | Patient ID | Patient Age | Repeat 1 O.D. | Repeat 1 Total IgM (nmol/ml) | Repeat 2 O.D. | Repeat 2 Total IgM (nmol/ml) | Repeat 3 O.D. | Repeat 3 Total IgM (nmol/ml) | Average Total IgM (nmol/ml) | Standard deviation | % CV |
|---|---|---|---|---|---|---|---|---|---|---|---|
| AD | NC17 | 75 | 0.11 | 5.9 | 0.11 | 5.3 | 0.11 | 5.9 | 5.7 | 0.3 | 6.0 |
| AD | NC14 | 77 | 0.22 | 13.2 | 0.31 | 18.7 | 0.27 | 16.3 | 16.1 | 2.7 | 17.1 |
| AD | NC15 | 78 | 0.21 | 12.5 | 0.22 | 12.8 | 0.20 | 11.3 | 12.2 | 0.8 | 6.3 |
| AD | NC11 | 83 | 0.26 | 15.7 | 0.25 | 15.3 | 0.25 | 15.2 | 15.4 | 0.3 | 1.9 |
| AD | NC20 | 90 | 0.51 | 32.6 | 0.52 | 32.7 | 0.52 | 32.8 | 32.7 | 0.1 | 0.3 |
| AD | NC18 | 91 | 0.51 | 32.1 | 0.52 | 33.1 | 0.54 | 34.3 | 33.2 | 1.1 | 3.2 |
| AD | NC19 | 93 | 0.27 | 16.4 | 0.26 | 15.7 | 0.26 | 15.5 | 15.9 | 0.5 | 2.9 |
| AD | NC13 | 94 | 0.12 | 6.4 | 0.15 | 8.1 | 0.12 | 6.5 | 7.0 | 0.9 | 13.6 |
| AD | NC12 | 103 | 0.65 | 41.4 | 0.53 | 33.7 | 0.55 | 35.1 | 36.7 | 4.1 | 11.2 |
| Control | WD-32339 | 63 | 0.17 | 9.8 | 0.17 | 9.4 | 0.16 | 9.2 | 9.5 | 0.3 | 3.2 |
| Control | WD-32347 | 66 | 0.27 | 16.6 | 0.29 | 17.3 | 0.29 | 17.5 | 17.2 | 0.5 | 2.9 |
| Control | WD-32398 | 70 | 0.38 | 23.3 | 0.37 | 23.1 | 0.38 | 23.6 | 23.3 | 0.3 | 1.1 |
| Control | WD-36002 | 70 | 0.25 | 15.1 | 0.25 | 15.2 | 0.25 | 15.1 | 15.2 | 0.0 | 0.3 |
| Control | WD-32351 | 70 | 0.29 | 17.9 | 0.31 | 18.8 | 0.30 | 18.2 | 18.3 | 0.4 | 2.4 |
| Control | WD-36008 | 73 | 0.46 | 29.1 | 0.48 | 30.4 | 0.46 | 28.7 | 29.4 | 0.9 | 3.1 |
| Control | WD-36010 | 74 | 0.27 | 16.5 | 0.26 | 15.9 | 0.27 | 16.1 | 16.2 | 0.3 | 1.9 |
| Control | WD-32346 | 76 | 0.25 | 14.7 | 0.27 | 16.1 | 0.26 | 15.4 | 15.4 | 0.7 | 4.8 |
| Control | WD-32350 | 66 | 0.29 | 17.4 | 0.31 | 18.8 | 0.33 | 20.3 | 18.8 | 1.5 | 7.8 |

FIG. 6E demonstrates that total IgM levels do not discriminate between individuals with and without Alzheimer's disease. Individual measurement values for all samples are shown as dots, and box-plots are shown for each distribution. The box-plots show the median values along with the upper quartile, lower quartile, and distance of the upper and lower quartile to the largest and lowest non-outlying points.

normalized anti-H1.0K180me2 IgG levels via scatter plot. This analysis allows for stratification of the Alzheimer's disease patients into distinct populations. Patients marked by 75, 77, 94, and 78 in FIG. 6M will likely respond to any Alzheimer's disease treatment. Patients marked by 90, 91, 93, 83, and 103 in FIG. 6M will likely respond to only specific Alzheimer's disease treatments, for example only non-immunomodulatory Alzheimer's disease treatments.

The invention claimed is:

1. An in vitro method for dimethylating n histone H1.0 peptide or a histone H1.0 protein comprising contacting the protein or peptide with a methyltransferase enzyme and a methyl donor under conditions that produce a specifically dimethylated protein or peptide, wherein greater than 50% of the produced protein or peptide is specifically dimethylated at a lysine residue corresponding to K180 of a human histone H1.0 protein, and wherein the methyltransferase enzyme is G9A methyltransferase or GLP methyltransferase.

2. The method of claim 1, wherein the peptide comprises a sequence selected from the group consisting of SEQ ID NOS:36-68.

3. The method of claim 1, wherein the protein comprises the sequence of SEQ ID NO:1.

4. The method of claim 1, wherein the protein or peptide is contacted with a G9A methyltransferase.

5. The method of claim 1, wherein the protein or peptide is contacted with a GLP methyltransferase.

6. The method of claim 1, wherein the methyl donor is S-Adenosyl-L-Methionine.

7. A histone H1.0 peptide or a histone H1.0 protein specifically dimethylated at a lysine residue corresponding to K180 of a human histone H1.0 protein produced by a method comprising contacting an H1.0 protein or an H1.0 peptide with a methyltransferase enzyme and methyl donor under conditions that allow for the specific dimethylation, wherein the methyltransferase enzyme is G9A methyltransferase or GLP methyltransferase, and wherein greater than 50% of the protein or peptide produced by the method is specifically dimethylated at a lysine residue corresponding to K180 of a human histone H1.0 protein.

8. The peptide of claim 7, wherein the H1.0 peptide comprises a sequence selected from the group consisting of SEQ ID NOs:36-68.

9. The protein of claim 7, wherein the H1.0 protein comprises the sequence of SEQ ID NO:1.

10. The protein of claim 7, wherein the specifically dimethylated H1.0 protein produced comprises the sequence of SEQ ID NO:2.

11. The peptide of claim 7, wherein the specifically dimethylated H1.0 peptide produced comprises the sequence of SEQ ID NOS:3-35.

* * * * *

UNITED STATES PATENT AND TRADEMARK OFFICE
CERTIFICATE OF CORRECTION

PATENT NO. : 10,921,324 B2  
APPLICATION NO. : 16/164701  
DATED : February 16, 2021  
INVENTOR(S) : Lunyak et al.

Page 1 of 1

It is certified that error appears in the above-identified patent and that said Letters Patent is hereby corrected as shown below:

In the Claims

At Claim 1, Column 93, Line 43, please replace "1. An in vitro method for dimethylating n histone H1.0" with --1. An in vitro method for dimethylating a histone H1.0--.

Signed and Sealed this
Twenty-fifth Day of April, 2023

Katherine Kelly Vidal
*Director of the United States Patent and Trademark Office*

SEQUENCE LISTING

<160> NUMBER OF SEQ ID NOS: 99

<210> SEQ ID NO 1
<211> LENGTH: 194
<212> TYPE: PRT
<213> ORGANISM: Homo sapiens

<400> SEQUENCE: 1

Met Thr Glu Asn Ser Thr Ser Ala Pro Ala Ala Lys Pro Lys Arg Ala
1               5                   10                  15

Lys Ala Ser Lys Lys Ser Thr Asp His Pro Lys Tyr Ser Asp Met Ile
            20                  25                  30

Val Ala Ala Ile Gln Ala Glu Lys Asn Arg Ala Gly Ser Ser Arg Gln
        35                  40                  45

Ser Ile Gln Lys Tyr Ile Lys Ser His Tyr Lys Val Gly Glu Asn Ala
    50                  55                  60

Asp Ser Gln Ile Lys Leu Ser Ile Lys Arg Leu Val Thr Thr Gly Val
65                  70                  75                  80

Leu Lys Gln Thr Lys Gly Val Gly Ala Ser Gly Ser Phe Arg Leu Ala
                85                  90                  95

Lys Ser Asp Glu Pro Lys Lys Ser Val Ala Phe Lys Lys Thr Lys Lys
            100                 105                 110

Glu Ile Lys Lys Val Ala Thr Pro Lys Lys Ala Ser Lys Pro Lys Lys
        115                 120                 125

Ala Ala Ser Lys Ala Pro Thr Lys Lys Pro Lys Ala Thr Pro Val Lys
    130                 135                 140

Lys Ala Lys Lys Lys Leu Ala Ala Thr Pro Lys Lys Ala Lys Lys Pro
145                 150                 155                 160

Lys Thr Val Lys Ala Lys Pro Val Lys Ala Ser Lys Pro Lys Lys Ala
                165                 170                 175

Lys Pro Val Lys Pro Lys Ala Lys Ser Ser Ala Lys Arg Ala Gly Lys
            180                 185                 190

Lys Lys

<210> SEQ ID NO 2
<211> LENGTH: 194
<212> TYPE: PRT
<213> ORGANISM: Artificial Sequence
<220> FEATURE:
<223> OTHER INFORMATION: Human H1.0 protein comprising a dimethylated
      K180
<220> FEATURE:
<221> NAME/KEY: misc_feature
<222> LOCATION: (180)..(180)
<223> OTHER INFORMATION: Lys is dimethylated

<400> SEQUENCE: 2

Met Thr Glu Asn Ser Thr Ser Ala Pro Ala Ala Lys Pro Lys Arg Ala
1               5                   10                  15

Lys Ala Ser Lys Lys Ser Thr Asp His Pro Lys Tyr Ser Asp Met Ile
            20                  25                  30

Val Ala Ala Ile Gln Ala Glu Lys Asn Arg Ala Gly Ser Ser Arg Gln
        35                  40                  45

Ser Ile Gln Lys Tyr Ile Lys Ser His Tyr Lys Val Gly Glu Asn Ala
    50                  55                  60

Asp Ser Gln Ile Lys Leu Ser Ile Lys Arg Leu Val Thr Thr Gly Val
65                  70                  75                  80

Leu Lys Gln Thr Lys Gly Val Gly Ala Ser Gly Ser Phe Arg Leu Ala

```
                85                  90                  95

Lys Ser Asp Glu Pro Lys Lys Ser Val Ala Phe Lys Lys Thr Lys Lys
            100                 105                 110

Glu Ile Lys Lys Val Ala Thr Pro Lys Lys Ala Ser Lys Pro Lys Lys
        115                 120                 125

Ala Ala Ser Lys Ala Pro Thr Lys Lys Pro Lys Ala Thr Pro Val Lys
    130                 135                 140

Lys Ala Lys Lys Lys Leu Ala Ala Thr Pro Lys Lys Ala Lys Lys Pro
145                 150                 155                 160

Lys Thr Val Lys Ala Lys Pro Val Lys Ala Ser Lys Pro Lys Lys Ala
                165                 170                 175

Lys Pro Val Lys Pro Lys Ala Lys Ser Ser Ala Lys Arg Ala Gly Lys
            180                 185                 190

Lys Lys

<210> SEQ ID NO 3
<211> LENGTH: 18
<212> TYPE: PRT
<213> ORGANISM: Artificial Sequence
<220> FEATURE:
<223> OTHER INFORMATION: H1.0K180me2 peptide
<220> FEATURE:
<221> NAME/KEY: misc_feature
<222> LOCATION: (16)..(16)
<223> OTHER INFORMATION: Lys is dimethylated

<400> SEQUENCE: 3

Ala Lys Pro Val Lys Ala Ser Lys Pro Lys Lys Ala Lys Pro Val Lys
1               5                   10                  15

Pro Lys

<210> SEQ ID NO 4
<211> LENGTH: 17
<212> TYPE: PRT
<213> ORGANISM: Artificial Sequence
<220> FEATURE:
<223> OTHER INFORMATION: H1.0K180me2 peptide
<220> FEATURE:
<221> NAME/KEY: misc_feature
<222> LOCATION: (15)..(15)
<223> OTHER INFORMATION: Lys is dimethylated

<400> SEQUENCE: 4

Lys Pro Val Lys Ala Ser Lys Pro Lys Lys Ala Lys Pro Val Lys Pro
1               5                   10                  15

Lys

<210> SEQ ID NO 5
<211> LENGTH: 16
<212> TYPE: PRT
<213> ORGANISM: Artificial Sequence
<220> FEATURE:
<223> OTHER INFORMATION: H1.0K180me2 peptide
<220> FEATURE:
<221> NAME/KEY: misc_feature
<222> LOCATION: (14)..(14)
<223> OTHER INFORMATION: Lys is dimethylated

<400> SEQUENCE: 5

Pro Val Lys Ala Ser Lys Pro Lys Lys Ala Lys Pro Val Lys Pro Lys
1               5                   10                  15

<210> SEQ ID NO 6
```

```
<211> LENGTH: 15
<212> TYPE: PRT
<213> ORGANISM: Artificial Sequence
<220> FEATURE:
<223> OTHER INFORMATION: H1.0K180me2 peptide
<220> FEATURE:
<221> NAME/KEY: misc_feature
<222> LOCATION: (13)..(13)
<223> OTHER INFORMATION: Lys is dimethylated

<400> SEQUENCE: 6

Val Lys Ala Ser Lys Pro Lys Lys Ala Lys Pro Val Lys Pro Lys
1               5                   10                  15

<210> SEQ ID NO 7
<211> LENGTH: 14
<212> TYPE: PRT
<213> ORGANISM: Artificial Sequence
<220> FEATURE:
<223> OTHER INFORMATION: H1.0K180me2 peptide
<220> FEATURE:
<221> NAME/KEY: misc_feature
<222> LOCATION: (12)..(12)
<223> OTHER INFORMATION: Lys is dimethylated

<400> SEQUENCE: 7

Lys Ala Ser Lys Pro Lys Lys Ala Lys Pro Val Lys Pro Lys
1               5                   10

<210> SEQ ID NO 8
<211> LENGTH: 13
<212> TYPE: PRT
<213> ORGANISM: Artificial Sequence
<220> FEATURE:
<223> OTHER INFORMATION: H1.0K180me2 peptide
<220> FEATURE:
<221> NAME/KEY: misc_feature
<222> LOCATION: (11)..(11)
<223> OTHER INFORMATION: Lys is dimethylated

<400> SEQUENCE: 8

Ala Ser Lys Pro Lys Lys Ala Lys Pro Val Lys Pro Lys
1               5                   10

<210> SEQ ID NO 9
<211> LENGTH: 12
<212> TYPE: PRT
<213> ORGANISM: Artificial Sequence
<220> FEATURE:
<223> OTHER INFORMATION: H1.0K180me2 peptide
<220> FEATURE:
<221> NAME/KEY: misc_feature
<222> LOCATION: (10)..(10)
<223> OTHER INFORMATION: Lys is dimethylated

<400> SEQUENCE: 9

Ser Lys Pro Lys Lys Ala Lys Pro Val Lys Pro Lys
1               5                   10

<210> SEQ ID NO 10
<211> LENGTH: 11
<212> TYPE: PRT
<213> ORGANISM: Artificial Sequence
<220> FEATURE:
<223> OTHER INFORMATION: H1.0K180me2 peptide
<220> FEATURE:
<221> NAME/KEY: misc_feature
<222> LOCATION: (9)..(9)
<223> OTHER INFORMATION: Lys is dimethylated

<400> SEQUENCE: 10
```

```
Lys Pro Lys Lys Ala Lys Pro Val Lys Pro Lys
1               5                   10

<210> SEQ ID NO 11
<211> LENGTH: 10
<212> TYPE: PRT
<213> ORGANISM: Artificial Sequence
<220> FEATURE:
<223> OTHER INFORMATION: H1.0K180me2 peptide
<220> FEATURE:
<221> NAME/KEY: misc_feature
<222> LOCATION: (8)..(8)
<223> OTHER INFORMATION: Lys is dimethylated

<400> SEQUENCE: 11

Pro Lys Lys Ala Lys Pro Val Lys Pro Lys
1               5                   10

<210> SEQ ID NO 12
<211> LENGTH: 9
<212> TYPE: PRT
<213> ORGANISM: Artificial Sequence
<220> FEATURE:
<223> OTHER INFORMATION: H1.0K180me2 peptide
<220> FEATURE:
<221> NAME/KEY: misc_feature
<222> LOCATION: (7)..(7)
<223> OTHER INFORMATION: Lys is dimethylated

<400> SEQUENCE: 12

Lys Lys Ala Lys Pro Val Lys Pro Lys
1               5

<210> SEQ ID NO 13
<211> LENGTH: 8
<212> TYPE: PRT
<213> ORGANISM: Artificial Sequence
<220> FEATURE:
<223> OTHER INFORMATION: H1.0K180me2 peptide
<220> FEATURE:
<221> NAME/KEY: misc_feature
<222> LOCATION: (6)..(6)
<223> OTHER INFORMATION: Lys is dimethylated

<400> SEQUENCE: 13

Lys Ala Lys Pro Val Lys Pro Lys
1               5

<210> SEQ ID NO 14
<211> LENGTH: 17
<212> TYPE: PRT
<213> ORGANISM: Artificial Sequence
<220> FEATURE:
<223> OTHER INFORMATION: H1.0K180me2 peptide
<220> FEATURE:
<221> NAME/KEY: misc_feature
<222> LOCATION: (16)..(16)
<223> OTHER INFORMATION: Lys is dimethylated

<400> SEQUENCE: 14

Ala Lys Pro Val Lys Ala Ser Lys Pro Lys Lys Ala Lys Pro Val Lys
1               5                   10                  15

Pro

<210> SEQ ID NO 15
<211> LENGTH: 16
<212> TYPE: PRT
<213> ORGANISM: Artificial Sequence
```

```
<220> FEATURE:
<223> OTHER INFORMATION: H1.0K180me2 peptide
<220> FEATURE:
<221> NAME/KEY: misc_feature
<222> LOCATION: (15)..(15)
<223> OTHER INFORMATION: Lys is dimethylated

<400> SEQUENCE: 15

Lys Pro Val Lys Ala Ser Lys Pro Lys Lys Ala Lys Pro Val Lys Pro
1               5                   10                  15

<210> SEQ ID NO 16
<211> LENGTH: 15
<212> TYPE: PRT
<213> ORGANISM: Artificial Sequence
<220> FEATURE:
<223> OTHER INFORMATION: H1.0K180me2 peptide
<220> FEATURE:
<221> NAME/KEY: misc_feature
<222> LOCATION: (14)..(14)
<223> OTHER INFORMATION: Lys is dimethylated

<400> SEQUENCE: 16

Pro Val Lys Ala Ser Lys Pro Lys Lys Ala Lys Pro Val Lys Pro
1               5                   10                  15

<210> SEQ ID NO 17
<211> LENGTH: 14
<212> TYPE: PRT
<213> ORGANISM: Artificial Sequence
<220> FEATURE:
<223> OTHER INFORMATION: H1.0K180me2 peptide
<220> FEATURE:
<221> NAME/KEY: misc_feature
<222> LOCATION: (13)..(13)
<223> OTHER INFORMATION: Lys is dimethylated

<400> SEQUENCE: 17

Val Lys Ala Ser Lys Pro Lys Lys Ala Lys Pro Val Lys Pro
1               5                   10

<210> SEQ ID NO 18
<211> LENGTH: 13
<212> TYPE: PRT
<213> ORGANISM: Artificial Sequence
<220> FEATURE:
<223> OTHER INFORMATION: H1.0K180me2 peptide
<220> FEATURE:
<221> NAME/KEY: misc_feature
<222> LOCATION: (12)..(12)
<223> OTHER INFORMATION: Lys is dimethylated

<400> SEQUENCE: 18

Lys Ala Ser Lys Pro Lys Lys Ala Lys Pro Val Lys Pro
1               5                   10

<210> SEQ ID NO 19
<211> LENGTH: 12
<212> TYPE: PRT
<213> ORGANISM: Artificial Sequence
<220> FEATURE:
<223> OTHER INFORMATION: H1.0K180me2 peptide
<220> FEATURE:
<221> NAME/KEY: misc_feature
<222> LOCATION: (11)..(11)
<223> OTHER INFORMATION: Lys is dimethylated

<400> SEQUENCE: 19

Ala Ser Lys Pro Lys Lys Ala Lys Pro Val Lys Pro
1               5                   10
```

```
<210> SEQ ID NO 20
<211> LENGTH: 11
<212> TYPE: PRT
<213> ORGANISM: Artificial Sequence
<220> FEATURE:
<223> OTHER INFORMATION: H1.0K180me2 peptide
<220> FEATURE:
<221> NAME/KEY: misc_feature
<222> LOCATION: (10)..(10)
<223> OTHER INFORMATION: Lys is dimethylated

<400> SEQUENCE: 20

Ser Lys Pro Lys Lys Ala Lys Pro Val Lys Pro
1               5                   10

<210> SEQ ID NO 21
<211> LENGTH: 10
<212> TYPE: PRT
<213> ORGANISM: Artificial Sequence
<220> FEATURE:
<223> OTHER INFORMATION: H1.0K180me2 peptide
<220> FEATURE:
<221> NAME/KEY: misc_feature
<222> LOCATION: (9)..(9)
<223> OTHER INFORMATION: Lys is dimethylated

<400> SEQUENCE: 21

Lys Pro Lys Lys Ala Lys Pro Val Lys Pro
1               5                   10

<210> SEQ ID NO 22
<211> LENGTH: 9
<212> TYPE: PRT
<213> ORGANISM: Artificial Sequence
<220> FEATURE:
<223> OTHER INFORMATION: H1.0K180me2 peptide
<220> FEATURE:
<221> NAME/KEY: misc_feature
<222> LOCATION: (8)..(8)
<223> OTHER INFORMATION: Lys is dimethylated

<400> SEQUENCE: 22

Pro Lys Lys Ala Lys Pro Val Lys Pro
1               5

<210> SEQ ID NO 23
<211> LENGTH: 8
<212> TYPE: PRT
<213> ORGANISM: Artificial Sequence
<220> FEATURE:
<223> OTHER INFORMATION: H1.0K180me2 peptide
<220> FEATURE:
<221> NAME/KEY: misc_feature
<222> LOCATION: (7)..(7)
<223> OTHER INFORMATION: Lys is dimethylated

<400> SEQUENCE: 23

Lys Lys Ala Lys Pro Val Lys Pro
1               5

<210> SEQ ID NO 24
<211> LENGTH: 7
<212> TYPE: PRT
<213> ORGANISM: Artificial Sequence
<220> FEATURE:
<223> OTHER INFORMATION: H1.0K180me2 peptide
<220> FEATURE:
<221> NAME/KEY: misc_feature
<222> LOCATION: (6)..(6)
```

<223> OTHER INFORMATION: Lys is dimethylated

<400> SEQUENCE: 24

Lys Ala Lys Pro Val Lys Pro
1               5

<210> SEQ ID NO 25
<211> LENGTH: 16
<212> TYPE: PRT
<213> ORGANISM: Artificial Sequence
<220> FEATURE:
<223> OTHER INFORMATION: H1.0K180me2 peptide
<220> FEATURE:
<221> NAME/KEY: misc_feature
<222> LOCATION: (16)..(16)
<223> OTHER INFORMATION: Lys is dimethylated

<400> SEQUENCE: 25

Ala Lys Pro Val Lys Ala Ser Lys Pro Lys Lys Ala Lys Pro Val Lys
1               5                   10                  15

<210> SEQ ID NO 26
<211> LENGTH: 15
<212> TYPE: PRT
<213> ORGANISM: Artificial Sequence
<220> FEATURE:
<223> OTHER INFORMATION: H1.0K180me2 peptide
<220> FEATURE:
<221> NAME/KEY: misc_feature
<222> LOCATION: (15)..(15)
<223> OTHER INFORMATION: Lys is dimethylated

<400> SEQUENCE: 26

Lys Pro Val Lys Ala Ser Lys Pro Lys Lys Ala Lys Pro Val Lys
1               5                   10                  15

<210> SEQ ID NO 27
<211> LENGTH: 14
<212> TYPE: PRT
<213> ORGANISM: Artificial Sequence
<220> FEATURE:
<223> OTHER INFORMATION: H1.0K180me2 peptide
<220> FEATURE:
<221> NAME/KEY: misc_feature
<222> LOCATION: (14)..(14)
<223> OTHER INFORMATION: Lys is dimethylated

<400> SEQUENCE: 27

Pro Val Lys Ala Ser Lys Pro Lys Lys Ala Lys Pro Val Lys
1               5                   10

<210> SEQ ID NO 28
<211> LENGTH: 13
<212> TYPE: PRT
<213> ORGANISM: Artificial Sequence
<220> FEATURE:
<223> OTHER INFORMATION: H1.0K180me2 peptide
<220> FEATURE:
<221> NAME/KEY: misc_feature
<222> LOCATION: (13)..(13)
<223> OTHER INFORMATION: Lys is dimethylated

<400> SEQUENCE: 28

Val Lys Ala Ser Lys Pro Lys Lys Ala Lys Pro Val Lys
1               5                   10

<210> SEQ ID NO 29
<211> LENGTH: 12
<212> TYPE: PRT

```
<213> ORGANISM: Artificial Sequence
<220> FEATURE:
<223> OTHER INFORMATION: H1.0K180me2 peptide
<220> FEATURE:
<221> NAME/KEY: misc_feature
<222> LOCATION: (12)..(12)
<223> OTHER INFORMATION: Lys is dimethylated

<400> SEQUENCE: 29

Lys Ala Ser Lys Pro Lys Lys Ala Lys Pro Val Lys
1               5                   10

<210> SEQ ID NO 30
<211> LENGTH: 11
<212> TYPE: PRT
<213> ORGANISM: Artificial Sequence
<220> FEATURE:
<223> OTHER INFORMATION: H1.0K180me2 peptide
<220> FEATURE:
<221> NAME/KEY: misc_feature
<222> LOCATION: (11)..(11)
<223> OTHER INFORMATION: Lys is dimethylated

<400> SEQUENCE: 30

Ala Ser Lys Pro Lys Lys Ala Lys Pro Val Lys
1               5                   10

<210> SEQ ID NO 31
<211> LENGTH: 10
<212> TYPE: PRT
<213> ORGANISM: Artificial Sequence
<220> FEATURE:
<223> OTHER INFORMATION: H1.0K180me2 peptide
<220> FEATURE:
<221> NAME/KEY: misc_feature
<222> LOCATION: (10)..(10)
<223> OTHER INFORMATION: Lys is dimethylated

<400> SEQUENCE: 31

Ser Lys Pro Lys Lys Ala Lys Pro Val Lys
1               5                   10

<210> SEQ ID NO 32
<211> LENGTH: 9
<212> TYPE: PRT
<213> ORGANISM: Artificial Sequence
<220> FEATURE:
<223> OTHER INFORMATION: H1.0K180me2 peptide
<220> FEATURE:
<221> NAME/KEY: misc_feature
<222> LOCATION: (9)..(9)
<223> OTHER INFORMATION: Lys is dimethylated

<400> SEQUENCE: 32

Lys Pro Lys Lys Ala Lys Pro Val Lys
1               5

<210> SEQ ID NO 33
<211> LENGTH: 8
<212> TYPE: PRT
<213> ORGANISM: Artificial Sequence
<220> FEATURE:
<223> OTHER INFORMATION: H1.0K180me2 peptide
<220> FEATURE:
<221> NAME/KEY: misc_feature
<222> LOCATION: (8)..(8)
<223> OTHER INFORMATION: Lys is dimethylated

<400> SEQUENCE: 33

Pro Lys Lys Ala Lys Pro Val Lys
```

```
<210> SEQ ID NO 34
<211> LENGTH: 7
<212> TYPE: PRT
<213> ORGANISM: Artificial Sequence
<220> FEATURE:
<223> OTHER INFORMATION: H1.0K180me2 peptide
<220> FEATURE:
<221> NAME/KEY: misc_feature
<222> LOCATION: (7)..(7)
<223> OTHER INFORMATION: Lys is dimethylated

<400> SEQUENCE: 34

Lys Lys Ala Lys Pro Val Lys
1               5

<210> SEQ ID NO 35
<211> LENGTH: 6
<212> TYPE: PRT
<213> ORGANISM: Artificial Sequence
<220> FEATURE:
<223> OTHER INFORMATION: H1.0K180me2 peptide
<220> FEATURE:
<221> NAME/KEY: misc_feature
<222> LOCATION: (6)..(6)
<223> OTHER INFORMATION: Lys is dimethylated

<400> SEQUENCE: 35

Lys Ala Lys Pro Val Lys
1               5

<210> SEQ ID NO 36
<211> LENGTH: 18
<212> TYPE: PRT
<213> ORGANISM: Homo sapiens

<400> SEQUENCE: 36

Ala Lys Pro Val Lys Ala Ser Lys Pro Lys Lys Ala Lys Pro Val
1               5                   10                  15

Pro Lys

<210> SEQ ID NO 37
<211> LENGTH: 17
<212> TYPE: PRT
<213> ORGANISM: Homo sapiens

<400> SEQUENCE: 37

Lys Pro Val Lys Ala Ser Lys Pro Lys Lys Ala Lys Pro Val Lys Pro
1               5                   10                  15

Lys

<210> SEQ ID NO 38
<211> LENGTH: 16
<212> TYPE: PRT
<213> ORGANISM: Homo sapiens

<400> SEQUENCE: 38

Pro Val Lys Ala Ser Lys Pro Lys Lys Ala Lys Pro Val Lys Pro Lys
1               5                   10                  15

<210> SEQ ID NO 39
<211> LENGTH: 15
<212> TYPE: PRT
<213> ORGANISM: Homo sapiens
```

-continued

```
<400> SEQUENCE: 39

Val Lys Ala Ser Lys Pro Lys Lys Ala Lys Pro Val Lys Pro Lys
1               5                   10                  15

<210> SEQ ID NO 40
<211> LENGTH: 14
<212> TYPE: PRT
<213> ORGANISM: Homo sapiens

<400> SEQUENCE: 40

Lys Ala Ser Lys Pro Lys Lys Ala Lys Pro Val Lys Pro Lys
1               5                   10

<210> SEQ ID NO 41
<211> LENGTH: 13
<212> TYPE: PRT
<213> ORGANISM: Homo sapiens

<400> SEQUENCE: 41

Ala Ser Lys Pro Lys Lys Ala Lys Pro Val Lys Pro Lys
1               5                   10

<210> SEQ ID NO 42
<211> LENGTH: 12
<212> TYPE: PRT
<213> ORGANISM: Homo sapiens

<400> SEQUENCE: 42

Ser Lys Pro Lys Lys Ala Lys Pro Val Lys Pro Lys
1               5                   10

<210> SEQ ID NO 43
<211> LENGTH: 11
<212> TYPE: PRT
<213> ORGANISM: Homo sapiens

<400> SEQUENCE: 43

Lys Pro Lys Lys Ala Lys Pro Val Lys Pro Lys
1               5                   10

<210> SEQ ID NO 44
<211> LENGTH: 10
<212> TYPE: PRT
<213> ORGANISM: Homo sapiens

<400> SEQUENCE: 44

Pro Lys Lys Ala Lys Pro Val Lys Pro Lys
1               5                   10

<210> SEQ ID NO 45
<211> LENGTH: 9
<212> TYPE: PRT
<213> ORGANISM: Homo sapiens

<400> SEQUENCE: 45

Lys Lys Ala Lys Pro Val Lys Pro Lys
1               5

<210> SEQ ID NO 46
<211> LENGTH: 8
<212> TYPE: PRT
<213> ORGANISM: Homo sapiens

<400> SEQUENCE: 46
```

```
Lys Ala Lys Pro Val Lys Pro Lys
1               5

<210> SEQ ID NO 47
<211> LENGTH: 17
<212> TYPE: PRT
<213> ORGANISM: Homo sapiens

<400> SEQUENCE: 47

Ala Lys Pro Val Lys Ala Ser Lys Pro Lys Lys Ala Lys Pro Val Lys
1               5                   10                  15

Pro

<210> SEQ ID NO 48
<211> LENGTH: 16
<212> TYPE: PRT
<213> ORGANISM: Homo sapiens

<400> SEQUENCE: 48

Lys Pro Val Lys Ala Ser Lys Pro Lys Lys Ala Lys Pro Val Lys Pro
1               5                   10                  15

<210> SEQ ID NO 49
<211> LENGTH: 15
<212> TYPE: PRT
<213> ORGANISM: Homo sapiens

<400> SEQUENCE: 49

Pro Val Lys Ala Ser Lys Pro Lys Lys Ala Lys Pro Val Lys Pro
1               5                   10                  15

<210> SEQ ID NO 50
<211> LENGTH: 14
<212> TYPE: PRT
<213> ORGANISM: Homo sapiens

<400> SEQUENCE: 50

Val Lys Ala Ser Lys Pro Lys Lys Ala Lys Pro Val Lys Pro
1               5                   10

<210> SEQ ID NO 51
<211> LENGTH: 13
<212> TYPE: PRT
<213> ORGANISM: Homo sapiens

<400> SEQUENCE: 51

Lys Ala Ser Lys Pro Lys Lys Ala Lys Pro Val Lys Pro
1               5                   10

<210> SEQ ID NO 52
<211> LENGTH: 12
<212> TYPE: PRT
<213> ORGANISM: Homo sapiens

<400> SEQUENCE: 52

Ala Ser Lys Pro Lys Lys Ala Lys Pro Val Lys Pro
1               5                   10

<210> SEQ ID NO 53
<211> LENGTH: 11
<212> TYPE: PRT
<213> ORGANISM: Homo sapiens

<400> SEQUENCE: 53
```

```
Ser Lys Pro Lys Lys Ala Lys Pro Val Lys Pro
1               5                   10
```

<210> SEQ ID NO 54
<211> LENGTH: 10
<212> TYPE: PRT
<213> ORGANISM: Homo sapiens

<400> SEQUENCE: 54

```
Lys Pro Lys Lys Ala Lys Pro Val Lys Pro
1               5                   10
```

<210> SEQ ID NO 55
<211> LENGTH: 9
<212> TYPE: PRT
<213> ORGANISM: Homo sapiens

<400> SEQUENCE: 55

```
Pro Lys Lys Ala Lys Pro Val Lys Pro
1               5
```

<210> SEQ ID NO 56
<211> LENGTH: 8
<212> TYPE: PRT
<213> ORGANISM: Homo sapiens

<400> SEQUENCE: 56

```
Lys Lys Ala Lys Pro Val Lys Pro
1               5
```

<210> SEQ ID NO 57
<211> LENGTH: 7
<212> TYPE: PRT
<213> ORGANISM: Homo sapiens

<400> SEQUENCE: 57

```
Lys Ala Lys Pro Val Lys Pro
1               5
```

<210> SEQ ID NO 58
<211> LENGTH: 16
<212> TYPE: PRT
<213> ORGANISM: Homo sapiens

<400> SEQUENCE: 58

```
Ala Lys Pro Val Lys Ala Ser Lys Pro Lys Lys Ala Lys Pro Val Lys
1               5                   10                  15
```

<210> SEQ ID NO 59
<211> LENGTH: 15
<212> TYPE: PRT
<213> ORGANISM: Homo sapiens

<400> SEQUENCE: 59

```
Lys Pro Val Lys Ala Ser Lys Pro Lys Lys Ala Lys Pro Val Lys
1               5                   10                  15
```

<210> SEQ ID NO 60
<211> LENGTH: 14
<212> TYPE: PRT
<213> ORGANISM: Homo sapiens

<400> SEQUENCE: 60

```
Pro Val Lys Ala Ser Lys Pro Lys Lys Ala Lys Pro Val Lys
1               5                   10
```

```
<210> SEQ ID NO 61
<211> LENGTH: 13
<212> TYPE: PRT
<213> ORGANISM: Homo sapiens

<400> SEQUENCE: 61

Val Lys Ala Ser Lys Pro Lys Lys Ala Lys Pro Val Lys
1               5                   10

<210> SEQ ID NO 62
<211> LENGTH: 12
<212> TYPE: PRT
<213> ORGANISM: Homo sapiens

<400> SEQUENCE: 62

Lys Ala Ser Lys Pro Lys Lys Ala Lys Pro Val Lys
1               5                   10

<210> SEQ ID NO 63
<211> LENGTH: 11
<212> TYPE: PRT
<213> ORGANISM: Homo sapiens

<400> SEQUENCE: 63

Ala Ser Lys Pro Lys Lys Ala Lys Pro Val Lys
1               5                   10

<210> SEQ ID NO 64
<211> LENGTH: 10
<212> TYPE: PRT
<213> ORGANISM: Homo sapiens

<400> SEQUENCE: 64

Ser Lys Pro Lys Lys Ala Lys Pro Val Lys
1               5                   10

<210> SEQ ID NO 65
<211> LENGTH: 9
<212> TYPE: PRT
<213> ORGANISM: Homo sapiens

<400> SEQUENCE: 65

Lys Pro Lys Lys Ala Lys Pro Val Lys
1               5

<210> SEQ ID NO 66
<211> LENGTH: 8
<212> TYPE: PRT
<213> ORGANISM: Homo sapiens

<400> SEQUENCE: 66

Pro Lys Lys Ala Lys Pro Val Lys
1               5

<210> SEQ ID NO 67
<211> LENGTH: 7
<212> TYPE: PRT
<213> ORGANISM: Homo sapiens

<400> SEQUENCE: 67

Lys Lys Ala Lys Pro Val Lys
1               5
```

```
<210> SEQ ID NO 68
<211> LENGTH: 6
<212> TYPE: PRT
<213> ORGANISM: Homo sapiens

<400> SEQUENCE: 68

Lys Ala Lys Pro Val Lys
1               5

<210> SEQ ID NO 69
<211> LENGTH: 18
<212> TYPE: PRT
<213> ORGANISM: Artificial Sequence
<220> FEATURE:
<223> OTHER INFORMATION: biotinylated H1.0 peptide
<220> FEATURE:
<221> NAME/KEY: misc_feature
<222> LOCATION: (1)..(1)
<223> OTHER INFORMATION: Ala is biotinylated

<400> SEQUENCE: 69

Ala Lys Pro Val Lys Ala Ser Lys Pro Lys Ala Lys Pro Val Lys
1               5                   10                  15

Pro Lys

<210> SEQ ID NO 70
<211> LENGTH: 18
<212> TYPE: PRT
<213> ORGANISM: Artificial Sequence
<220> FEATURE:
<223> OTHER INFORMATION: biotinylated H1.0 dimethylated peptide
<220> FEATURE:
<221> NAME/KEY: misc_feature
<222> LOCATION: (1)..(1)
<223> OTHER INFORMATION: Ala is biotinylated
<220> FEATURE:
<221> NAME/KEY: misc_feature
<222> LOCATION: (16)..(16)
<223> OTHER INFORMATION: Lys is dimethylated

<400> SEQUENCE: 70

Ala Lys Pro Val Lys Ala Ser Lys Pro Lys Ala Lys Pro Val Lys
1               5                   10                  15

Pro Lys

<210> SEQ ID NO 71
<211> LENGTH: 20
<212> TYPE: DNA
<213> ORGANISM: Artificial Sequence
<220> FEATURE:
<223> OTHER INFORMATION: GLP-Forward primer

<400> SEQUENCE: 71
aggggagtgc tgacacagag                                           20

<210> SEQ ID NO 72
<211> LENGTH: 20
<212> TYPE: DNA
<213> ORGANISM: Artificial Sequence
<220> FEATURE:
<223> OTHER INFORMATION: GLP-Reverse primer

<400> SEQUENCE: 72
gggatcttta ctggctgcat                                           20

<210> SEQ ID NO 73
<211> LENGTH: 20
```

<212> TYPE: DNA
<213> ORGANISM: Artificial Sequence
<220> FEATURE:
<223> OTHER INFORMATION: Beta-actin-Forward primer

<400> SEQUENCE: 73
ctcttccagc cttccttcct                                               20

<210> SEQ ID NO 74
<211> LENGTH: 20
<212> TYPE: DNA
<213> ORGANISM: Artificial Sequence
<220> FEATURE:
<223> OTHER INFORMATION: Beta-actin-Reverse primer

<400> SEQUENCE: 74
agcactgtgt tggcgtacag                                               20

<210> SEQ ID NO 75
<211> LENGTH: 20
<212> TYPE: DNA
<213> ORGANISM: Artificial Sequence
<220> FEATURE:
<223> OTHER INFORMATION: H1.0-Forward primer

<400> SEQUENCE: 75
ctcaagcaga ccaaaggggt                                               20

<210> SEQ ID NO 76
<211> LENGTH: 20
<212> TYPE: DNA
<213> ORGANISM: Artificial Sequence
<220> FEATURE:
<223> OTHER INFORMATION: H1.0-Reverse primer

<400> SEQUENCE: 76
ggcgtggcta ccttcttgat                                               20

<210> SEQ ID NO 77
<211> LENGTH: 20
<212> TYPE: DNA
<213> ORGANISM: Artificial Sequence
<220> FEATURE:
<223> OTHER INFORMATION: H1.1-Forward primer

<400> SEQUENCE: 77
aggcaacggg tgcatctaaa                                               20

<210> SEQ ID NO 78
<211> LENGTH: 20
<212> TYPE: DNA
<213> ORGANISM: Artificial Sequence
<220> FEATURE:
<223> OTHER INFORMATION: H1.1-Reverse primer

<400> SEQUENCE: 78
gatttccttg ttgccgcagg                                               20

<210> SEQ ID NO 79
<211> LENGTH: 20
<212> TYPE: DNA
<213> ORGANISM: Artificial Sequence
<220> FEATURE:
<223> OTHER INFORMATION: H1.2-Forward primer

<400> SEQUENCE: 79

-continued caaagaaggc caaggttgcg                                              20

<210> SEQ ID NO 80
<211> LENGTH: 21
<212> TYPE: DNA
<213> ORGANISM: Artificial Sequence
<220> FEATURE:
<223> OTHER INFORMATION: H1.2-Reverse primer

<400> SEQUENCE: 80
cgccttctta ggcttgacaa c                                            21

<210> SEQ ID NO 81
<211> LENGTH: 20
<212> TYPE: DNA
<213> ORGANISM: Artificial Sequence
<220> FEATURE:
<223> OTHER INFORMATION: H1.3-Forward primer

<400> SEQUENCE: 81
agtggccaag agtgcgaaaa                                              20

<210> SEQ ID NO 82
<211> LENGTH: 20
<212> TYPE: DNA
<213> ORGANISM: Artificial Sequence
<220> FEATURE:
<223> OTHER INFORMATION: H1.3-Reverse primer

<400> SEQUENCE: 82
cttcggcttc cccgacttag                                              20

<210> SEQ ID NO 83
<211> LENGTH: 21
<212> TYPE: DNA
<213> ORGANISM: Artificial Sequence
<220> FEATURE:
<223> OTHER INFORMATION: H1.4-Forward primer

<400> SEQUENCE: 83
acgcttgcct tcaacatgtc c                                            21

<210> SEQ ID NO 84
<211> LENGTH: 20
<212> TYPE: DNA
<213> ORGANISM: Artificial Sequence
<220> FEATURE:
<223> OTHER INFORMATION: H1.4-Reverse primer

<400> SEQUENCE: 84
agtaatgagc tcggacaccg                                              20

<210> SEQ ID NO 85
<211> LENGTH: 20
<212> TYPE: DNA
<213> ORGANISM: Artificial Sequence
<220> FEATURE:
<223> OTHER INFORMATION: H1.5-Forward primer

<400> SEQUENCE: 85
ccggctaaga agaaggcaac                                              20

<210> SEQ ID NO 86
<211> LENGTH: 20
<212> TYPE: DNA
<213> ORGANISM: Artificial Sequence
<220> FEATURE:
<223> OTHER INFORMATION: H1.5-Reverse primer

<400> SEQUENCE: 86
gctccttaga agcagccaca                                               20

<210> SEQ ID NO 87
<211> LENGTH: 20
<212> TYPE: DNA
<213> ORGANISM: Artificial Sequence
<220> FEATURE:
<223> OTHER INFORMATION: G9A-Forward primer

<400> SEQUENCE: 87
tgctgaggct gatgtgagag                                               20

<210> SEQ ID NO 88
<211> LENGTH: 20
<212> TYPE: DNA
<213> ORGANISM: Artificial Sequence
<220> FEATURE:
<223> OTHER INFORMATION: G9A-Reverse primer

<400> SEQUENCE: 88
ggtcacacag gtggttgatg                                               20

<210> SEQ ID NO 89
<211> LENGTH: 20
<212> TYPE: PRT
<213> ORGANISM: Artificial Sequence
<220> FEATURE:
<223> OTHER INFORMATION: H1.0K180me2 peptide
<220> FEATURE:
<221> NAME/KEY: misc_feature
<222> LOCATION: (18)..(18)
<223> OTHER INFORMATION: Lys is dimethylated

<400> SEQUENCE: 89

Cys Ala Lys Pro Val Lys Ala Ser Lys Pro Lys Lys Ala Lys Pro Val
1               5                   10                  15

Lys Lys Pro Lys
            20

<210> SEQ ID NO 90
<211> LENGTH: 19
<212> TYPE: PRT
<213> ORGANISM: Artificial Sequence
<220> FEATURE:
<223> OTHER INFORMATION: Keyhole Limpet Hemocyanin (KLH) conjugated to a
      H1.0K180me2 peptide
<220> FEATURE:
<221> NAME/KEY: misc_feature
<222> LOCATION: (1)..(1)
<223> OTHER INFORMATION: Cys is conjugated to Keyhole Limpet Hemocyanin
<220> FEATURE:
<221> NAME/KEY: misc_feature
<222> LOCATION: (17)..(17)
<223> OTHER INFORMATION: Lys is dimethylated

<400> SEQUENCE: 90

Cys Ala Lys Pro Val Lys Ala Ser Lys Pro Lys Lys Ala Lys Pro Val
1               5                   10                  15

Lys Pro Lys

<210> SEQ ID NO 91
<211> LENGTH: 19
<212> TYPE: PRT

<213> ORGANISM: Artificial Sequence
<220> FEATURE:
<223> OTHER INFORMATION: biotinylated H1.0K180me2 peptide
<220> FEATURE:
<221> NAME/KEY: misc_feature
<222> LOCATION: (1)..(1)
<223> OTHER INFORMATION: Cys is biotinylated
<220> FEATURE:
<221> NAME/KEY: misc_feature
<222> LOCATION: (17)..(17)
<223> OTHER INFORMATION: Lys is dimethylated

<400> SEQUENCE: 91

Cys Ala Lys Pro Val Lys Ala Ser Lys Pro Lys Lys Ala Lys Pro Val
1               5                   10                  15

Lys Pro Lys

<210> SEQ ID NO 92
<211> LENGTH: 19
<212> TYPE: PRT
<213> ORGANISM: Artificial Sequence
<220> FEATURE:
<223> OTHER INFORMATION: bovine serum albumin (BSA)-conjugated
      H1.0K180me2 peptide
<220> FEATURE:
<221> NAME/KEY: misc_feature
<222> LOCATION: (1)..(1)
<223> OTHER INFORMATION: Cys is conjugated to bovine serum albumin (BSA)
<220> FEATURE:
<221> NAME/KEY: misc_feature
<222> LOCATION: (17)..(17)
<223> OTHER INFORMATION: Lys is dimethylated

<400> SEQUENCE: 92

Cys Ala Lys Pro Val Lys Ala Ser Lys Pro Lys Lys Ala Lys Pro Val
1               5                   10                  15

Lys Pro Lys

<210> SEQ ID NO 93
<211> LENGTH: 18
<212> TYPE: PRT
<213> ORGANISM: Artificial Sequence
<220> FEATURE:
<223> OTHER INFORMATION: dimethylated K180me2 peptide
<220> FEATURE:
<221> NAME/KEY: misc_feature
<222> LOCATION: (2)..(2)
<223> OTHER INFORMATION: Lys is methylated
<220> FEATURE:
<221> NAME/KEY: misc_feature
<222> LOCATION: (16)..(16)
<223> OTHER INFORMATION: Lys is dimethylated

<400> SEQUENCE: 93

Ala Lys Pro Val Lys Ala Ser Lys Pro Lys Lys Ala Lys Pro Val Lys
1               5                   10                  15

Pro Lys

<210> SEQ ID NO 94
<211> LENGTH: 18
<212> TYPE: PRT
<213> ORGANISM: Artificial Sequence
<220> FEATURE:
<223> OTHER INFORMATION: dimethylated K180me2 peptide
<220> FEATURE:
<221> NAME/KEY: misc_feature
<222> LOCATION: (10)..(11)
<223> OTHER INFORMATION: Lys is trimethylated
<220> FEATURE:
<221> NAME/KEY: misc_feature

```
<222> LOCATION: (13)..(13)
<223> OTHER INFORMATION: Lys is methylated
<220> FEATURE:
<221> NAME/KEY: misc_feature
<222> LOCATION: (16)..(16)
<223> OTHER INFORMATION: Lys is dimethylated

<400> SEQUENCE: 94

Ala Lys Pro Val Lys Ala Ser Lys Pro Lys Lys Ala Lys Pro Val Lys
1               5                   10                  15

Pro Lys

<210> SEQ ID NO 95
<211> LENGTH: 18
<212> TYPE: PRT
<213> ORGANISM: Artificial Sequence
<220> FEATURE:
<223> OTHER INFORMATION: dimethylated K180me2 peptide
<220> FEATURE:
<221> NAME/KEY: misc_feature
<222> LOCATION: (10)..(10)
<223> OTHER INFORMATION: Lys is methylated
<220> FEATURE:
<221> NAME/KEY: misc_feature
<222> LOCATION: (16)..(16)
<223> OTHER INFORMATION: Lys is trimethylated

<400> SEQUENCE: 95

Ala Lys Pro Val Lys Ala Ser Lys Pro Lys Lys Ala Lys Pro Val Lys
1               5                   10                  15

Pro Lys

<210> SEQ ID NO 96
<211> LENGTH: 194
<212> TYPE: PRT
<213> ORGANISM: Artificial Sequence
<220> FEATURE:
<223> OTHER INFORMATION: methylated H1.0 protein
<220> FEATURE:
<221> NAME/KEY: misc_feature
<222> LOCATION: (121)..(121)
<223> OTHER INFORMATION: Lys is dimethylated
<220> FEATURE:
<221> NAME/KEY: misc_feature
<222> LOCATION: (169)..(169)
<223> OTHER INFORMATION: Lys is dimethylated
<220> FEATURE:
<221> NAME/KEY: misc_feature
<222> LOCATION: (172)..(172)
<223> OTHER INFORMATION: Lys is methylated
<220> FEATURE:
<221> NAME/KEY: misc_feature
<222> LOCATION: (175)..(175)
<223> OTHER INFORMATION: Lys is dimethylated
<220> FEATURE:
<221> NAME/KEY: misc_feature
<222> LOCATION: (180)..(180)
<223> OTHER INFORMATION: Lys is dimethylated

<400> SEQUENCE: 96

Met Thr Glu Asn Ser Thr Ser Ala Pro Ala Ala Lys Pro Lys Arg Ala
1               5                   10                  15

Lys Ala Ser Lys Lys Ser Thr Asp His Pro Lys Tyr Ser Asp Met Ile
            20                  25                  30

Val Ala Ala Ile Gln Ala Glu Lys Asn Arg Ala Gly Ser Ser Arg Gln
        35                  40                  45

Ser Ile Gln Lys Tyr Ile Lys Ser His Tyr Lys Val Gly Glu Asn Ala
    50                  55                  60
```

```
Asp Ser Gln Ile Lys Leu Ser Ile Lys Arg Leu Val Thr Thr Gly Val
 65                  70                  75                  80

Leu Lys Gln Thr Lys Gly Val Gly Ala Ser Gly Ser Phe Arg Leu Ala
                 85                  90                  95

Lys Ser Asp Glu Pro Lys Lys Ser Val Ala Phe Lys Lys Thr Lys Lys
            100                 105                 110

Glu Ile Lys Lys Val Ala Thr Pro Lys Lys Ala Ser Lys Pro Lys Lys
        115                 120                 125

Ala Ala Ser Lys Ala Pro Thr Lys Lys Pro Lys Ala Thr Pro Val Lys
    130                 135                 140

Lys Ala Lys Lys Lys Leu Ala Ala Thr Pro Lys Lys Ala Lys Lys Pro
145                 150                 155                 160

Lys Thr Val Lys Ala Lys Pro Val Lys Ala Ser Lys Pro Lys Lys Ala
                165                 170                 175

Lys Pro Val Lys Pro Lys Ala Lys Ser Ser Ala Lys Arg Ala Gly Lys
            180                 185                 190

Lys Lys
```

<210> SEQ ID NO 97
<211> LENGTH: 194
<212> TYPE: PRT
<213> ORGANISM: Artificial Sequence
<220> FEATURE:
<223> OTHER INFORMATION: methylated H1.0 protein
<220> FEATURE:
<221> NAME/KEY: misc_feature
<222> LOCATION: (111)..(111)
<223> OTHER INFORMATION: Lys is dimethylated
<220> FEATURE:
<221> NAME/KEY: misc_feature
<222> LOCATION: (112)..(112)
<223> OTHER INFORMATION: Lys is trimethylated
<220> FEATURE:
<221> NAME/KEY: misc_feature
<222> LOCATION: (115)..(115)
<223> OTHER INFORMATION: Lys is dimethylated
<220> FEATURE:
<221> NAME/KEY: misc_feature
<222> LOCATION: (116)..(116)
<223> OTHER INFORMATION: Lys is trimethylated
<220> FEATURE:
<221> NAME/KEY: misc_feature
<222> LOCATION: (121)..(121)
<223> OTHER INFORMATION: Lys is trimethylated
<220> FEATURE:
<221> NAME/KEY: misc_feature
<222> LOCATION: (122)..(122)
<223> OTHER INFORMATION: Lys is dimethylated
<220> FEATURE:
<221> NAME/KEY: misc_feature
<222> LOCATION: (125)..(125)
<223> OTHER INFORMATION: Lys is methylated
<220> FEATURE:
<221> NAME/KEY: misc_feature
<222> LOCATION: (127)..(127)
<223> OTHER INFORMATION: Lys is dimethylated
<220> FEATURE:
<221> NAME/KEY: misc_feature
<222> LOCATION: (128)..(128)
<223> OTHER INFORMATION: Lys is trimethylated
<220> FEATURE:
<221> NAME/KEY: misc_feature
<222> LOCATION: (137)..(137)
<223> OTHER INFORMATION: Lys is trimethylated
<220> FEATURE:
<221> NAME/KEY: misc_feature
<222> LOCATION: (139)..(139)
<223> OTHER INFORMATION: Lys is dimethylated
<220> FEATURE:
<221> NAME/KEY: misc_feature

```
<222> LOCATION: (144)..(144)
<223> OTHER INFORMATION: Lys is methylated
<220> FEATURE:
<221> NAME/KEY: misc_feature
<222> LOCATION: (145)..(145)
<223> OTHER INFORMATION: Lys is trimethylated
<220> FEATURE:
<221> NAME/KEY: misc_feature
<222> LOCATION: (147)..(147)
<223> OTHER INFORMATION: Lys is dimethylated
<220> FEATURE:
<221> NAME/KEY: misc_feature
<222> LOCATION: (148)..(148)
<223> OTHER INFORMATION: Lys is trimethylated
<220> FEATURE:
<221> NAME/KEY: misc_feature
<222> LOCATION: (149)..(149)
<223> OTHER INFORMATION: Lys is methylated
<220> FEATURE:
<221> NAME/KEY: misc_feature
<222> LOCATION: (155)..(156)
<223> OTHER INFORMATION: Lys is trimethylated
<220> FEATURE:
<221> NAME/KEY: misc_feature
<222> LOCATION: (158)..(158)
<223> OTHER INFORMATION: Lys is dimethylated
<220> FEATURE:
<221> NAME/KEY: misc_feature
<222> LOCATION: (159)..(159)
<223> OTHER INFORMATION: Lys is methylated
<220> FEATURE:
<221> NAME/KEY: misc_feature
<222> LOCATION: (161)..(161)
<223> OTHER INFORMATION: Lys is trimethylated
<220> FEATURE:
<221> NAME/KEY: misc_feature
<222> LOCATION: (164)..(164)
<223> OTHER INFORMATION: Lys is trimethylated
<220> FEATURE:
<221> NAME/KEY: misc_feature
<222> LOCATION: (166)..(166)
<223> OTHER INFORMATION: Lys is dimethylated
<220> FEATURE:
<221> NAME/KEY: misc_feature
<222> LOCATION: (169)..(169)
<223> OTHER INFORMATION: Lys is trimethylated
<220> FEATURE:
<221> NAME/KEY: misc_feature
<222> LOCATION: (172)..(172)
<223> OTHER INFORMATION: Lys is methylated
<220> FEATURE:
<221> NAME/KEY: misc_feature
<222> LOCATION: (174)..(175)
<223> OTHER INFORMATION: Lys is trimethylated
<220> FEATURE:
<221> NAME/KEY: misc_feature
<222> LOCATION: (177)..(177)
<223> OTHER INFORMATION: Lys is dimethylated
<220> FEATURE:
<221> NAME/KEY: misc_feature
<222> LOCATION: (180)..(180)
<223> OTHER INFORMATION: Lys is methylated
<220> FEATURE:
<221> NAME/KEY: misc_feature
<222> LOCATION: (182)..(182)
<223> OTHER INFORMATION: Lys is methylated
<220> FEATURE:
<221> NAME/KEY: misc_feature
<222> LOCATION: (184)..(184)
<223> OTHER INFORMATION: Lys is trimethylated
<220> FEATURE:
<221> NAME/KEY: misc_feature
<222> LOCATION: (188)..(188)
<223> OTHER INFORMATION: Lys is dimethylated
<220> FEATURE:
<221> NAME/KEY: misc_feature
<222> LOCATION: (192)..(192)
<223> OTHER INFORMATION: Lys is dimethylated
```

<400> SEQUENCE: 97

Met Thr Glu Asn Ser Thr Ser Ala Pro Ala Ala Lys Pro Lys Arg Ala
1               5                   10                  15

Lys Ala Ser Lys Lys Ser Thr Asp His Pro Lys Tyr Ser Asp Met Ile
            20                  25                  30

Val Ala Ala Ile Gln Ala Glu Lys Asn Arg Ala Gly Ser Ser Arg Gln
        35                  40                  45

Ser Ile Gln Lys Tyr Ile Lys Ser His Tyr Lys Val Gly Glu Asn Ala
    50                  55                  60

Asp Ser Gln Ile Lys Leu Ser Ile Lys Arg Leu Val Thr Thr Gly Val
65                  70                  75                  80

Leu Lys Gln Thr Lys Gly Val Gly Ala Ser Gly Ser Phe Arg Leu Ala
                85                  90                  95

Lys Ser Asp Glu Pro Lys Lys Ser Val Ala Phe Lys Lys Thr Lys Lys
            100                 105                 110

Glu Ile Lys Lys Val Ala Thr Pro Lys Lys Ala Ser Lys Pro Lys Lys
            115                 120                 125

Ala Ala Ser Lys Ala Pro Thr Lys Lys Pro Lys Ala Thr Pro Val Lys
        130                 135                 140

Lys Ala Lys Lys Lys Leu Ala Ala Thr Pro Lys Lys Ala Lys Lys Pro
145                 150                 155                 160

Lys Thr Val Lys Ala Lys Pro Val Lys Ala Ser Lys Pro Lys Lys Ala
                165                 170                 175

Lys Pro Val Lys Pro Lys Ala Lys Ser Ser Ala Lys Arg Ala Gly Lys
            180                 185                 190

Lys Lys

<210> SEQ ID NO 98
<211> LENGTH: 194
<212> TYPE: PRT
<213> ORGANISM: Homo sapiens
<220> FEATURE:
<221> NAME/KEY: misc_feature
<222> LOCATION: (121)..(121)
<223> OTHER INFORMATION: Lys is dimethylated
<220> FEATURE:
<221> NAME/KEY: misc_feature
<222> LOCATION: (169)..(169)
<223> OTHER INFORMATION: Lys is dimethylated
<220> FEATURE:
<221> NAME/KEY: misc_feature
<222> LOCATION: (172)..(172)
<223> OTHER INFORMATION: Lys is methylated
<220> FEATURE:
<221> NAME/KEY: misc_feature
<222> LOCATION: (175)..(175)
<223> OTHER INFORMATION: Lys is dimethylated
<220> FEATURE:
<221> NAME/KEY: misc_feature
<222> LOCATION: (180)..(180)
<223> OTHER INFORMATION: Lys is dimethylated

<400> SEQUENCE: 98

Met Thr Glu Asn Ser Thr Ser Ala Pro Ala Ala Lys Pro Lys Arg Ala
1               5                   10                  15

Lys Ala Ser Lys Lys Ser Thr Asp His Pro Lys Tyr Ser Asp Met Ile
            20                  25                  30

Val Ala Ala Ile Gln Ala Glu Lys Asn Arg Ala Gly Ser Ser Arg Gln
        35                  40                  45

Ser Ile Gln Lys Tyr Ile Lys Ser His Tyr Lys Val Gly Glu Asn Ala
    50                  55                  60

Asp Ser Gln Ile Lys Leu Ser Ile Lys Arg Leu Val Thr Thr Gly Val
65                  70                  75                  80

Leu Lys Gln Thr Lys Gly Val Gly Ala Ser Gly Ser Phe Arg Leu Ala
            85                  90                  95

Lys Ser Asp Glu Pro Lys Lys Ser Val Ala Phe Lys Thr Lys Lys
        100                 105                 110

Glu Ile Lys Lys Val Ala Thr Pro Lys Ala Ser Lys Pro Lys Lys
        115                 120                 125

Ala Ala Ser Lys Ala Pro Thr Lys Lys Pro Lys Ala Thr Pro Val Lys
130                 135                 140

Lys Ala Lys Lys Lys Leu Ala Ala Thr Pro Lys Lys Ala Lys Lys Pro
145                 150                 155                 160

Lys Thr Val Lys Ala Lys Pro Val Lys Ala Ser Lys Pro Lys Lys Ala
                165                 170                 175

Lys Pro Val Lys Pro Lys Ala Lys Ser Ser Ala Lys Arg Ala Gly Lys
            180                 185                 190

Lys Lys

<210> SEQ ID NO 99
<211> LENGTH: 194
<212> TYPE: PRT
<213> ORGANISM: Homo sapiens
<220> FEATURE:
<221> NAME/KEY: misc_feature
<222> LOCATION: (111)..(111)
<223> OTHER INFORMATION: Lys is dimethylated
<220> FEATURE:
<221> NAME/KEY: misc_feature
<222> LOCATION: (112)..(112)
<223> OTHER INFORMATION: Lys is trimethylated
<220> FEATURE:
<221> NAME/KEY: misc_feature
<222> LOCATION: (115)..(115)
<223> OTHER INFORMATION: Lys is dimethylated
<220> FEATURE:
<221> NAME/KEY: misc_feature
<222> LOCATION: (116)..(116)
<223> OTHER INFORMATION: Lys is trimethylated
<220> FEATURE:
<221> NAME/KEY: misc_feature
<222> LOCATION: (121)..(121)
<223> OTHER INFORMATION: Lys is trimethylated
<220> FEATURE:
<221> NAME/KEY: misc_feature
<222> LOCATION: (122)..(122)
<223> OTHER INFORMATION: Lys is dimethylated
<220> FEATURE:
<221> NAME/KEY: misc_feature
<222> LOCATION: (125)..(125)
<223> OTHER INFORMATION: Lys is methylated
<220> FEATURE:
<221> NAME/KEY: misc_feature
<222> LOCATION: (127)..(127)
<223> OTHER INFORMATION: Lys is dimethylated
<220> FEATURE:
<221> NAME/KEY: misc_feature
<222> LOCATION: (128)..(128)
<223> OTHER INFORMATION: Lys is trimethylated
<220> FEATURE:
<221> NAME/KEY: misc_feature
<222> LOCATION: (137)..(137)
<223> OTHER INFORMATION: Lys is trimethylated
<220> FEATURE:
<221> NAME/KEY: misc_feature
<222> LOCATION: (139)..(139)
<223> OTHER INFORMATION: Lys is dimethylated
<220> FEATURE:
<221> NAME/KEY: misc_feature
<222> LOCATION: (144)..(144)

```
<223> OTHER INFORMATION: Lys is methylated
<220> FEATURE:
<221> NAME/KEY: misc_feature
<222> LOCATION: (145)..(145)
<223> OTHER INFORMATION: Lys is dimethylated
<220> FEATURE:
<221> NAME/KEY: misc_feature
<222> LOCATION: (147)..(147)
<223> OTHER INFORMATION: Lys is dimethylated
<220> FEATURE:
<221> NAME/KEY: misc_feature
<222> LOCATION: (148)..(148)
<223> OTHER INFORMATION: Lys is trimethylated
<220> FEATURE:
<221> NAME/KEY: misc_feature
<222> LOCATION: (149)..(149)
<223> OTHER INFORMATION: Lys is methylated
<220> FEATURE:
<221> NAME/KEY: misc_feature
<222> LOCATION: (155)..(155)
<223> OTHER INFORMATION: Lys is trimethylated
<220> FEATURE:
<221> NAME/KEY: misc_feature
<222> LOCATION: (156)..(156)
<223> OTHER INFORMATION: Lys is trimethylated
<220> FEATURE:
<221> NAME/KEY: misc_feature
<222> LOCATION: (158)..(158)
<223> OTHER INFORMATION: Lys is dimethylated
<220> FEATURE:
<221> NAME/KEY: misc_feature
<222> LOCATION: (159)..(159)
<223> OTHER INFORMATION: Lys is methylated
<220> FEATURE:
<221> NAME/KEY: misc_feature
<222> LOCATION: (161)..(161)
<223> OTHER INFORMATION: Lys is trimethylated
<220> FEATURE:
<221> NAME/KEY: misc_feature
<222> LOCATION: (164)..(164)
<223> OTHER INFORMATION: Lys is trimethylated
<220> FEATURE:
<221> NAME/KEY: misc_feature
<222> LOCATION: (166)..(166)
<223> OTHER INFORMATION: Lys is dimethylated
<220> FEATURE:
<221> NAME/KEY: misc_feature
<222> LOCATION: (169)..(169)
<223> OTHER INFORMATION: Lys is trimethylated
<220> FEATURE:
<221> NAME/KEY: misc_feature
<222> LOCATION: (172)..(172)
<223> OTHER INFORMATION: Lys is methylated
<220> FEATURE:
<221> NAME/KEY: misc_feature
<222> LOCATION: (174)..(174)
<223> OTHER INFORMATION: Lys is trimethylated
<220> FEATURE:
<221> NAME/KEY: misc_feature
<222> LOCATION: (175)..(175)
<223> OTHER INFORMATION: Lys is trimethylated
<220> FEATURE:
<221> NAME/KEY: misc_feature
<222> LOCATION: (177)..(177)
<223> OTHER INFORMATION: Lys is dimethylated
<220> FEATURE:
<221> NAME/KEY: misc_feature
<222> LOCATION: (180)..(180)
<223> OTHER INFORMATION: Lys is methylated
<220> FEATURE:
<221> NAME/KEY: misc_feature
<222> LOCATION: (182)..(182)
<223> OTHER INFORMATION: Lys is methylated
<220> FEATURE:
<221> NAME/KEY: misc_feature
<222> LOCATION: (184)..(184)
<223> OTHER INFORMATION: Lys is trimethylated
<220> FEATURE:
<221> NAME/KEY: misc_feature
```

```
<222> LOCATION: (188)..(188)
<223> OTHER INFORMATION: Lys is dimethylated
<220> FEATURE:
<221> NAME/KEY: misc_feature
<222> LOCATION: (192)..(192)
<223> OTHER INFORMATION: Lys is dimethylated

<400> SEQUENCE: 99

Met Thr Glu Asn Ser Thr Ser Ala Pro Ala Ala Lys Pro Lys Arg Ala
1               5                   10                  15

Lys Ala Ser Lys Lys Ser Thr Asp His Pro Lys Tyr Ser Asp Met Ile
            20                  25                  30

Val Ala Ala Ile Gln Ala Glu Lys Asn Arg Ala Gly Ser Ser Arg Gln
        35                  40                  45

Ser Ile Gln Lys Tyr Ile Lys Ser His Tyr Lys Val Gly Glu Asn Ala
    50                  55                  60

Asp Ser Gln Ile Lys Leu Ser Ile Lys Arg Leu Val Thr Thr Gly Val
65                  70                  75                  80

Leu Lys Gln Thr Lys Gly Val Gly Ala Ser Gly Ser Phe Arg Leu Ala
                85                  90                  95

Lys Ser Asp Glu Pro Lys Lys Ser Val Ala Phe Lys Lys Thr Lys Lys
                100                 105                 110

Glu Ile Lys Lys Val Ala Thr Pro Lys Lys Ala Ser Lys Pro Lys Lys
            115                 120                 125

Ala Ala Ser Lys Ala Pro Thr Lys Lys Pro Lys Ala Thr Pro Val Lys
        130                 135                 140

Lys Ala Lys Lys Lys Leu Ala Ala Thr Pro Lys Lys Ala Lys Lys Pro
145                 150                 155                 160

Lys Thr Val Lys Ala Lys Pro Val Lys Ala Ser Lys Pro Lys Lys Ala
                165                 170                 175

Lys Pro Val Lys Pro Lys Ala Lys Ser Ser Ala Lys Arg Ala Gly Lys
            180                 185                 190

Lys Lys
```